(12) United States Patent
Rothberg et al.

(10) Patent No.: US 6,355,423 B1
(45) Date of Patent: Mar. 12, 2002

(54) METHODS AND DEVICES FOR MEASURING DIFFERENTIAL GENE EXPRESSION

(75) Inventors: Jonathan Marc Rothberg; Girish N. Nallur, both of Guilford; Xinghua Hu, New Haven, all of CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/203,231

(22) Filed: Dec. 2, 1998

Related U.S. Application Data

(60) Provisional application No. 60/105,305, filed on Dec. 3, 1997.

(51) Int. Cl.[7] ............... C12Q 1/68; C12P 19/34; C07H 21/02; C07H 21/04
(52) U.S. Cl. ............. 435/6; 435/91.2; 536/23.1; 536/24.3
(58) Field of Search ............... 435/6, 91.2; 536/23.1, 536/24.3

(56) References Cited

U.S. PATENT DOCUMENTS

| 5,468,613 A | 11/1995 | Erlich et al. | |
|---|---|---|---|
| 5,624,711 A | 4/1997 | Sundberg et al. | |
| 5,741,644 A | 4/1998 | Kambara et al. | |
| 5,760,130 A | 6/1998 | Johnston et al. | |
| 5,770,722 A | 6/1998 | Lockhart et al. | |
| 5,780,232 A | * 7/1998 | Arlinghaus et al. | 435/6 |
| 5,871,697 A | * 2/1999 | Rothberg et al. | 422/68.1 |
| 5,972,693 A | * 10/1999 | Rothberg et al. | 435/287.2 |
| 6,141,657 A | 10/2000 | Rothberg et al. | |

FOREIGN PATENT DOCUMENTS

| WO | WO 97/15690 | * 5/1997 |
|---|---|---|
| WO | WO 97/27317 | 7/1997 |

* cited by examiner

*Primary Examiner*—Jeffrey Fredman
(74) *Attorney, Agent, or Firm*—Pennie & Edmonds LLP

(57) ABSTRACT

This invention includes methods for identifying nucleic acids in a sample of nucleic acids by observing sequence sets present in the nucleic acids of the sample and then identifying those sequences in a nucleic acid sequence database having the sequence sets observed. In a preferred embodiment, a sequence set consists of two primary subsequences and an additional subsequence having determined mutual relationships. The methods include those for observing the sequence sets and those for performing sequence database searches. This invention also includes devices for recognizing in parallel the additional subsequences in a sample of as well as methods for the use of these devices. In a preferred embodiment, the devices include probes bound to a planar surface that recognize additional subsequence by hybridization, and the methods of use include features to improve the specificity and reproducibility of this hybridization.

45 Claims, 14 Drawing Sheets

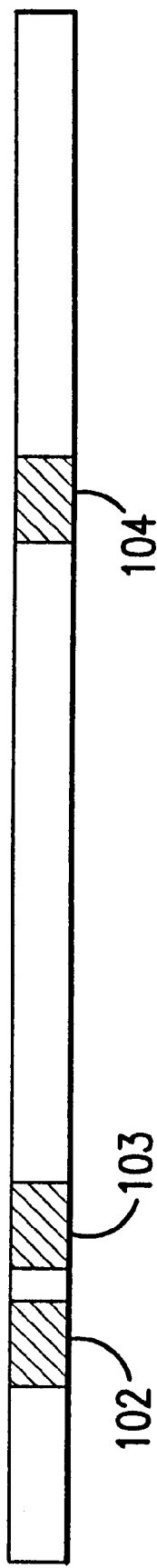
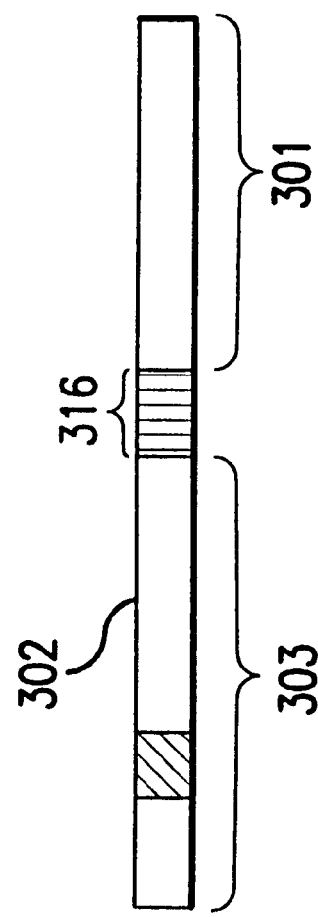
FIG.1
FIG.3

| QUADRANT A | QUADRANT G |
| (256 GRID) | (256 GRID) |
| 5'-NNNNA | 5'-NNNNG |

| QUADRANT T | QUADRANT C |
| (256 GRID) | (256 GRID) |
| 5'-NNNNT | 5'-NNNNC |

FIG.5B

→ = SITES OF LIGATION

METHODS AND DEVICES FOR MEASURING DIFFERENTIAL GENE EXPRESSION

CROSS REFERENCE TO RELATED APPLICATION

This application claims the benefit of provisional application Serial No. 60/105,305, filed Dec. 3, 1997, which is hereby incorporated by reference in its entirety.

This invention was made with Government support under Grant number 70NANB5H1036 awarded by the National Institute of Standards and Technology. The Government has certain rights in the invention.

1 FIELD OF THE INVENTION

The field of the invention relates to methods and devices for qualitatively and quantitatively observing nucleic acids in a sample of nucleic acids, and more particularly to methods and devices that recognize the presence of a set of subsequences in each nucleic acid in the sample and identify the nucleic acid from a set of subsequences by reference to a database of sequences likely to be present in the sample.

2 BACKGROUND

Modern biology teaches the importance of genes and gene expression to processes of health and disease. New individual genes causing or predisposing to conditions or diseases are now reported almost daily. Additionally, it is commonly understood that observing and measuring the spatial and temporal patterns of gene expression in health and disease will contribute immensely to further understanding of these states. Therefore, any observational method that can rapidly, accurately, and economically observe and measure the presence or expression of selected individual genes or of whole genomes will be of great value. Of even more value will be methods that can directly and quantitatively be applied to the complex mixtures of genomic DNA ("gDNA") samples or expressed DNA ("cDNA") samples (synthesized from selected RNA pools) that are typically derived directly from biological samples.

Current observation and measurement methods suffer from one or more disadvantages that render them unnecessarily inaccurate, time consuming, labor intensive, or expensive. Such disadvantages flow from requirements for, e.g., prior knowledge of gene sequences, cloning of complex mixtures of sequences into many individual samples each of a single sequence, repetitive sequencing of sample nucleic acids, electrophoretic separations of nucleic acid fragments, and so forth.

For example, observation techniques for individual mRNA or cDNA molecules, such as Northern blot analysis, RNase protection, or selective hybridization to arrayed cDNA libraries (see Sambrook et al., *Molecular Cloning—A Laboratory Manual,* Cold Spring Harbor Press, New York (1989)) depend on specific hybridization of a single oligonucleotide probe complementary to the known sequence of an individual molecule. Since a single human cell is estimated to express 10,000–30,000 genes (Liang et al., Science, 257:967–971 (1992)), most of which remain unknown, single probe methods to identify all sequences in a complex sample are prohibitively cumbersome and time consuming.

Similarly, traditional nucleic acid sequencing (Sanger et al., Proc. Natl. Acad. Sci. USA, 74:5463–5467 (1977)), sequencing by hybridization ("SBH") using combinatorial probe libraries (Drmanac et al., Science 260:1649–1652 (1993); U.S. Pat. No. 5,202,231, Apr. 13, 1993 to Drmanac et al.), or classification by oligomer sequence signatures (Lennon et al., Trends Genetics 7:314–317 (1991)), and positional SBH (Broude et al., Proc. Natl. Acad. Sci. USA 91:3072–3076 (1994)) also require that samples be arrayed into purified clones, making the methods inappropriate for complex mixtures.

Several approaches have been described that attempt to characterize complex mixtures of nucleic acids without cloning, all of which at least require electrophoretic separation and/or traditional sequencing. A basic approach is that of differential display (Liang et al., Science 257:967–71 (1992); Liang et al., Curr. Op. Immunol. 7:274–280 (1995)), which uses the polymerase chain reaction ("PCR") with an oligo (dT) primer and a degenerate primer designed to hybridize within a few hundred bases of the cDNA 3'-end. The resulting DNA subsequences of varying length are electrophoretically separated to yield a pattern of, preferably, 100–250 bands. This approach, at best providing only qualitative "fingerprints" of gene expression, suffers from well-known problems, including a high false positive rate, migration of multiple nucleic acid species within a single observed band, and non-quantitative results. Further, putative gene identification depends on purification and traditional sequencing of the components in electrophoretic bands.

Additionally, approaches have been described which attempt to improve differential display, but without obviating the need for traditional sequencing and/or electrophoretic separation. For example, a method described in European Patent Application 0 534 858 A1 (published Mar. 31, 1993), is directed to applying differential display to gDNA samples by using restriction endonuclease ("RE") digestion together with PCR employing phasing primers in order to reduce the complexity of such samples to levels electrophoretically observable. The multiple phasing primers divide the gDNA samples in multiple pools of lower complexity, which are electrophoretically separated to yield qualitative "fingerprints."

Other methods improving on differential display include the following, all of which are similarly limited to generating electrophoretic "fingerprints." One such improvement is described in U.S. Pat. No. 5,459,937 (Oct. 17, 1995). This method generates multiple pools of lower complexity by using sequential rounds of PCR applied to 3'-end fragments of cDNAs. The 3'-end fragments lie between a recognition site for a frequently-cutting RE and the poly(A) tail of the cDNA. Fragments in the multiple pools are finally putatively identified by electrophoretic separation and individual sequencing. Another example of such an improvement is described by Prashar et al., Proc. Natl. Acad. Sci. USA 93:659–663 (1996). Primarily, this reference describes an alternative method for generating similar 3'-end fragments, which lie between a recognition site for a frequently-cutting RE and the poly(A) tail of the cDNA.

Differing from differential display is another class of methods, which observe gene expression by sampling, that is, these methods repetitively sequence nucleic acids in a sample and count the sequence occurrences in order to statistically observe gene expression. Such methods require sequencing and are statistically limited in their ability to discover rare transcripts. An early example of such a method determined and counted expressed sequence tags ("ESTs"), and is described in Adams et al., Science, 252:1651–1656 (1991). Another example is named "serial analysis of gene expression" (Velculescu et al., Science, 270:484–487 (1995)). According to this method, cDNA molecules are converted into representative "tags," which are short oligonucleotides generated from Type IIS RE single-stranded overhangs located at determined distances from the 3'-end of source cDNA. (Type IIS REs cleave a defined distance (up to 20 bp) away from their asymmetric recognition sites (Szybalski, Gene 40:169 (1985)). Approximate, putative identification of the source of a tag requires sequencing the tag and using the sequence and location information to look up possible source sequences in a nucleic acid sequence database.

Other methods for gene and gene-expression measurement, although unrelated to differential display, still have certain disadvantages, such as, e.g., requiring electrophoretic separation. Such a method is described in PCT Publication WO 97/15690, which is herein incorporated by reference in its entirety. According to this method "signals" are generated that represent the length of a nucleotide sequence between defined subsequences in a target nucleic acid. The defined subsequences are preferably restriction endonuclease sites or oligomer binding sites. These signals can then be compared to results of computer simulated signal generation experiments using computer databases of nucleic acid sequences. By this comparison, particular DNA sequences in the database can be identified as present in sample, since they are predicted to generate signals which are also observed. The length information of the signals of this method is, disadvantageously, observed electrophoretically.

All methods previously described for the analysis of complex mixtures of nucleic acids require electrophoretic separation, possibly together with nucleic acid cloning and sequencing. These procedures can be unnecessarily labor intensive, slow, and uneconomical. Recently new approaches have been reported that can, in some implementations, obviate the need for, at least, electrophoretic separation. Such methods depend on hybridization of probe oligonucleotides to recognize short subsequences of from 4 to 20 base pairs on target nucleic acids. The oligonucleotides can be either present in solution or arrayed on a planar surface, such as a glass chip ("chip").

Subsequence recognition by hybridization performed in solution, however, often requires electrophoretic separation. Methods reported in Smith, PCR Methods and Applications 2:21–27(1992) and in Unrau et al., Gene, 145:163–169 (1994) use type IIS or interrupted palindromic ("IP") REs to create single-stranded overhangs of unknown sequence from a sample of cDNAs. These overhangs are recognized by hybridization to a plurality of degenerate adapters (called "indexers" in the latter reference), each possible overhang being recognizable by the one adapter having a complementary single-stranded terminus. The adapters also include primer sequences, and successful hybridization of an adapter is detected by electrophoretic separation of PCR amplification products.

Hybridization specificity can be improved by using a ligase, which requires exact base-pairing for ligation. See, e.g., Landegren et al., Science 241, 1077–1080 (1988), in which hybridization is only recognized if two probe oligonucleotides hybridize to adjacent position on a target DNA sequence and are ligated by T4 DNA ligase. "Strand-invasion" (Guilfoyle et al., Nucleic Acids Res. 25:1854–1858 (1997)) is an extension of the indexing approach designed to further improve hybridization specificity. In strand-invasion, the duplex adapter, or indexer, has a longer single-stranded terminus which has a few determined nucleotides terminal to the previously described degenerate subsequence. The extra, determined nucleotides "invade" into and base pair with a known terminal subsequence of the RE recognition sites, which is adjacent to the unknown single-stranded overhangs that the indexers recognize, thereby improving hybridization stringency. Again, successfully hybridized adapters are recognized by PCR amplification and electrophoretic separation.

Electrophoretic separations can be obviated by arraying the probe oligonucleotides on a chip. Such chips can be prepared by depositing already synthesized oligonucleotide on a derivatized glass surface, or by synthesizing the oligonucleotide directly on the glass surface using a combination of photolithography and oligonucleotide chemistry (McCall et al., Proc. Nat. Acad. Sci. USA 93:13555–13560 (1996)). These probe oligonucleotides are typically designed to hybridize to 10, 15, or 20 bases of a target DNA. Chips capable of recognizing in principle up to 6500 genes have been prepared. The chips are hybridized to samples of fluorescently tagged target DNAs, and are then imaged to determine to which oligonucleotides hybridization has occurred. Although some success has been reported with such chips, well-known problems remain, including those of obtaining unambiguous and reliable hybridization signals. Current methods for solving such signal to noise problems call for the use of significantly redundant sets of probe oligonucleotides. For example, to observe one subsequence of one gene currently requires the synthesis of multiple (greater than 20 per gene) overlapping and mismatched oligonucleotide probes in order to obtain statistically significant data, including data necessary to apply corrections for mismatched hybridizations or non-specific binding. The need for such redundancy of immobilized probes poses serious throughput and cost limitations, especially in view of the 130,000 or so genes possibly expressed in human tissues.

Various hybridization alternatives include the use of arrays of peptide nucleic acids ("PNA") (Weiler et al., Nucleic Acids Res. 25, 2792–2799 (1997)). PNAs, having the bases linked via N-(2-aminomethyl)-glycine moiety, obey Watson-Crick base-pairing rules with DNA but with greater stability than corresponding DNA:DNA hybrids. In another alternative, PCR amplified target DNAs, prepared perhaps from ESTs or cDNA libraries, are physically tethered onto planar surface instead of arrays of probe oligonucleotide.

Therefore, these described observational methods for gene-expression are not capable of rapidly, accurately, and economically observing and measuring the presence or expression of selected individual genes or of whole genomes. These methods typically require, for example, prior knowledge of gene sequences, or cloning of complex mixtures of sequences into many individual samples of a single sequence, or repetitive sequencing of sample components, or electrophoretic separations, and so forth. Importantly, they have not been able to accurately and economically utilize the potential of arrayed oligonucleotides.

Accordingly, an observational method that overcomes these disadvantages will be of great value.

Citation of a reference herein shall not be construed as an admission that such is prior art to the present invention.

3 SUMMARY OF THE INVENTION

It is a broad object of this invention to provide methods and devices for observing and measuring the presence and expression of individual genes or entire genomes that overcome the previously described problems. In particular, the methods and devices of the instant invention make accurate and efficient use of arrayed oligonucleotides (called herein a universal detection array or "UDA") to avoid any requirements for cloning of complex mixtures of sequences into many individual samples of a single sequence, repetitive sequencing of sample components, electrophoretic separations, and so forth.

The methods of this invention identify and quantify nucleic acids in a sample by observing the presence of sequence sets in nucleic acids in a sample. A sequence set, in a preferred but non-limiting embodiment, includes three subsequences, a first and second primary subsequence and an additional subsequence. The subsequences have certain preferred positional constants, including (i) that the additional subsequence is spaced apart from the first primary subsequence by a fixed number of nucleotides in all sequence sets, and (ii) that the second primary subsequence is spaced apart from both the first primary and the additional subsequence by a variable number of nucleotides. Where the first primary and the additional subsequence are positioned adjacently, the sequence set can be considered to include only two independent subsequences.

Once having observed sequence sets from a nucleic acid sample, they can be interpreted with reference to a database of nucleic acid sequences. A sequence set defines a search query which can be used to scan a database of nucleic acid sequences for those sequences having the particular sequence set. Any sequences found are sequences of nucleic acids likely to be present in the original sample of nucleic acids. If no such sequences are found, then a novel nucleic acid, which generates such sequence sets, likely exists in the sample. Preferably, the database includes sequences of nucleic acids likely to be present in the sample, perhaps produced by a pre-selection step from a more general nucleic acid sequence database.

In a preferred embodiment, the search query defined by the sequence set is represented as a regular expression, which is used by regular expression search tools to search nucleic acid sequences represented as symbol strings. In an alternate embodiment, an index of subsequences present in the database of nucleotide sequences is first constructed. Second, using this index, sequences are searched for the regular expression representing a sequence set. This alternative embodiment is preferred in the case of repetitive searches of the same sequence database because it increases search efficiency.

The lengths of the subsequences in a sequence set are chosen in order to obtain adequate resolution and separation of the gene-calling methods. Resolution, defining how precisely a sequence set identifies a nucleic acid, is therefore related to how many sequences in the sequence database have a particular sequence set. Separation defines how accurately and uniquely the observation methods observe a sequence set. In the preferred embodiment, where a UDA of this invention observes the additional sequences in a subsample in parallel, separation improves with decreasing complexity of subsamples. Both these measures are improved by longer subsequences. However, longer subsequences result in increased numbers of subsamples (see below) necessary for adequate coverage. Generally, for nucleic acids derived from expressed human genes, preferred lengths for the subsequences are between 4 and 8.

Preferred methods for observing sequence sets in a sample of nucleic acids generally proceed in two steps. In a first step, a subsample of nucleic acid fragments is formed having those nucleic acids that have selected sequences for the first and second primary subsequences. In a second step, the sequence of the additional subsequence in nucleic acid fragments of the subsample is determined. By forming a plurality of subsamples, each subsample having different selected primary subsequences, there can be a high likelihood that each nucleic acid in the sample will be represented in at least one subsample (that is, the "coverage" of the original sample is adequate). Preferably, the length and sequence of the primary subsequences are chosen to minimize the number of subsamples for adequate coverage in view of the previously described considerations of resolution and separation.

In more detail, preferred methods for the first step produce a subsample by digesting the original sample with restriction endonuclease ("RE") enzymes that digest nucleic acids within their recognition sequence and produce single-stranded terminal overhangs. The primary subsequences recognized are therefore the recognition sequences of such REs. Complementary adapters are ligated to these terminal overhangs, either simultaneously with or sequentially to RE digestion. One such adapter preferably has a conjugated biotin (or other capture moiety) to aid in removing improperly digested or undigested fragments from the reaction products. The other adapter preferably has a subsequence which is the recognition site of a restriction endonuclease that digests nucleic acids outside of its recognition site (a Type IIS RE).

Preferred methods for the second step determine the additional subsequences of all the nucleic acids in a subsample simultaneously and in parallel by hybridization of the additional subsequences to an array of probes. To facilitate such a hybridization, a further digestion of the nucleic acid fragments leaves remaining fragments having the additional subsequences as partially single-stranded terminal subsequences. In one embodiment, the additional subsequences are the single-stranded terminal subsequence; and in an alternative embodiment, the additional subsequences include both the single-stranded terminal subsequence and adjacent double-stranded portions of the remaining fragments. This second digestion is preferably with a Type IIS RE, whose recognition site is positioned on one of the previous complementary adapters in view of the length and placement of the additional sequence.

The probes of the probe array have terminal subsequences for hybridizing with and recognizing the terminal additional subsequences. Where all nucleic acids in a sample are to be identified, the probe array includes probes with all possible terminal subsequences for recognizing all possible additional subsequences. In this case, for improved separation, the number of fragments in the subsample of fragments is advantageously less than the number of probes in the array, and the length of the additional subsequence can be chosen accordingly.

In preferred embodiments, techniques are employed to improve the specificity and strength of probe and fragment hybridization, especially in view of the length of the additional subsequences, which can be as short as 4 nucleotides. One technique employs stacking oligomers that hybridize to the probe adjacent to the hybridized fragments. Energetic base stacking interactions between the hybridized stacking oligomer and fragment improve overall hybridized duplex stability. Another technique employs a ligase enzyme to ligate nicks only in those hybridization structures that are fully and correctly hybridized, followed by a wash step to remove mis-hybridized, and, therefore, un-ligated fragments and stacking oligomers.

Where the additional subsequence is only single-stranded, a correctly hybridized structure of the fragment, the probe, and the stacking oligomer is a duplex with no nucleotide gaps. Where the additional subsequence includes also an adjacent double-stranded subsequence which hybridizes with the probe, the hybridized structure has one strand of the fragment partially "displaced" by the "invading" strand of the probe, forming what is called a "displacement structure."

The nucleotide sequence of the additional sequence is determined by detecting to which probes fragments have hybridized. In various embodiments, either the fragment, the stacking oligomer, or both can be labeled, for example by fluorescent dyes, and the hybridization can be detected by optical or laser stimulation of the dyes.

Advantageously, hybridization and ligation conditions are selected so that the amount of hybridized fragment reflects the concentration of the original fragment in the subsample, and thus that of the original nucleic acid in the sample. To achieve such responsiveness, the concentration of the fragment is made less that the concentration of the probe in order to avoid probe saturation, and the time of hybridization is made less than the time for complete hybridization in order to avoid fragment depletion. Fragments are taken to be not depleted when, preferably, more than ¼ of their initial concentration remains, and more preferably, when more than ½ remains.

In preferred embodiments of the UDA, the probes are attached to solid supports, which are preferably planar glass surfaces or glass beads. Therefore, probes have a linker region of sufficient length in order to reduce stearic hindrance to hybridization due to the surface attachment, and a functional group in order to bind to corresponding groups on the solid supports. Preferably, an amino functional group binds to isothiocyanate groups on derivitized glass surfaces.

This invention is also directed to observing specific and known nucleic acids in the original sample. In this case, the sequence sets to be observed are chosen to be those present in the specific nucleic acids. Subsamples are generated only for the primary subsequences present in the chosen sequence sets, and probe arrays need only include probes for the additional subsequences present in the chosen sequence sets.

Applications of the general gene-calling methods of the invention include observing differential gene expression between pairs of tissues in defined biological states. In this case, the original sample of nucleic acids can be cDNA synthesized from mRNA harvested from the tissues according to methods known in the art. Such differential expression information has many known and developing uses. Applications of these methods directed only to specific genes include, for example, diagnostic or therapeutic tests of the presence and expression of disease-related genes.

This Summary is not limiting. Other embodiments and applications will be apparent to one of average skill in view of the following figures and description.

According to a first embodiment, the instant invention includes a method for identifying and quantifying nucleic acids in a sample of nucleic acids comprising observing subsequence sets present in said sample of nucleic acids, wherein a subsequence set comprises at least two nucleotide subsequences in a non-adjacent arrangement and said subsequence set is observed in said sample if a nucleic acid in said sample includes said two nucleotide subsequences in a non-adjacent arrangement; and searching a database of nucleic acid sequences in order to locate database sequences having said observed subsequence sets or to determine that no such database sequences exist, said database of nucleic acid sequences comprising nucleic acid sequences that might be present in said sample; thereby identifying said located database sequences as sequences of nucleic acids present in said sample.

In an aspect of the first embodiment, the step of observing includes the steps of: providing at least one subsample of first nucleic acid fragments, said first nucleic acid fragments in said subsample being derived from those nucleic acids in said sample in which said first and said second primary nucleotide subsequences have selected sequences; and determining the sequence of said additional nucleotide subsequence in each said first nucleic acid fragment of said subsample.

In another aspect of the first embodiment, the determining step includes: producing second nucleic acid fragments from said first nucleic acid fragments of said subsample, wherein said second nucleic acid fragments have a single-stranded terminal nucleotide subsequence, and wherein said additional nucleotide subsequence comprises said single-stranded terminal nucleotide subsequence; hybridizing a plurality of species of probe molecules with said second nucleic acid fragments, probe molecules of each of said species of probe molecules capable of hybridizing with said second nucleic acid fragments having a particular sequence for said additional nucleotide subsequence; and detecting which of said species of probe molecules has hybridized with said second nucleic acid fragments; whereby the sequences of said additional nucleotide sequences are determined.

In another aspect of the first embodiment, the searching step further includes examining individually and sequentially each sequence in the sequence database for the presence of a sequence set; or representing a sequence set as a regular expression in order to search sequences in the sequence database. In a further aspect, the first embodiment includes, prior to said searching step, a step of constructing an index of subsequences present in the sequences of said sequence database, and wherein said searching step consults said index of subsequences; or after said searching step, a step of storing said located sequences in a permanent computer-readable storage. In further aspects, the step of storing stores along with said located sequences additional information describing said sample of nucleic acids; or the step of observing further observes the amount of nucleic acids in said sample having said observed subsequence sets, and wherein said step of storing stores along with said located sequences said observed amount.

According to a second embodiment, the instant invention includes a computer readable storage medium produced according to the previous methods.

According to a third embodiment, the instant invention includes a method for identifying and quantifying nucleic acids in a sample of nucleic acids comprising: providing at least one subsample of first nucleic acid fragments, said first nucleic acid fragments in said subsample being derived from those nucleic acids in said sample in which a first primary nucleotide subsequence and a second primary nucleotide subsequence have selected sequences, wherein said first and said second primary nucleotide subsequences are not contiguous in said nucleic acids; producing second nucleic acid fragments having a single-stranded terminal nucleotide subsequence from said subsample of first nucleic acid fragments; determining a sequence for an additional nucleotide subsequence of said second nucleic acid fragments, said additional nucleotide subsequence comprising said single-stranded terminal nucleotide subsequence, and wherein said single-stranded nucleotide subsequence is spaced apart from said first primary nucleotide subsequence by a distance of zero or more nucleotides which is the same in all second nucleic acid fragments, said determining by: hybridizing a plurality of species of probe molecules with said second nucleic acid fragments, each of said species of probe molecules capable of hybridizing with said second nucleic acid fragments having a particular sequence for said additional nucleotide subsequence, and detecting which of said species of probe molecules has hybridized with said second nucleic acid fragments, and the amount of said second nucleic acid fragments hybridized with said species of probe molecule; searching a database of nucleic acid sequences in order to locate database sequences having said selected first primary subsequence, said selected second primary subsequence, and said determined additional subsequence or to determine that no such database sequences exist, said database of nucleic acid sequences comprising nucleic acid sequences that might be present in said sample; thereby identifying said located database sequences as sequences of nucleic acids present in said sample.

In an aspect of the third embodiment, the probe molecules comprise a nucleotide sequence, which in turn comprises a hybridization region nucleotide subsequence and a core nucleotide subsequence, the sequence of said hybridization region nucleotide subsequence being complementary to the sequence of said additional subsequence hybridizable to said species of probe molecules, said core nucleotide subsequence being adjacent to said hybridization region nucleotide subsequence, and wherein said step of hybridizing comprises: hybridizing a plurality of species of probe molecules with said second nucleic acid fragments and with stacking oligomers to form a hybridization structure, the sequence of said stacking oligomers being complementary to a hybridizable portion of the sequence of said core nucleotide subsequence of said probe molecules, said hybridizable portion being adjacent to said hybridization region nucleotide subsequence; and ligating nicks in said hybridization structure.

According to a fourth embodiment, the instant invention includes a detection array for recognizing terminal subsequences of target nucleic acids, said array comprising: one or more surfaces; a plurality of discrete observational cells arranged on said surfaces in which are bound probe molecules, each probe molecule being a member of one of a plurality of species of probe molecules, wherein each discrete observational cell has bound probe molecules of at most one species, and wherein said probe molecules comprise: a hybridization region, wherein said hybridization region of said probe molecules of one species of probe molecule are capable of hybridizing with said terminal subsequences of said target nucleic acids having a single nucleotide sequence, a core region adjacent to and conjugated with said hybridization region, and an attachment means for binding said hybridization region and said core region to said surfaces; and a plurality of discrete error-checking cells to which are bound probe molecules, wherein to each discrete error-checking cell are bound probe molecules of a plurality of species, such that each species of probe molecule is bound to one discrete observational cell and to at least one discrete error-checking cell.

According to a fifth embodiment, the instant invention includes a method for detecting a terminal subsequence in a target nucleic acid, comprising: hybridizing said target nucleic acid and a stacking oligonucleotide to probe molecules of a universal array of the fourth embodiment, wherein said target nucleic acid hybridizes to a hybridization region of said probe molecules, wherein said stacking oligonucleotide hybridizes to at least a portion of a core region of said probes, said portion being adjacent to said hybridization region of said probe molecules, and wherein said hybridizing occurs in the presence of a nucleic acid ligase under ligating conditions; washing the hybridized detection array in denaturing conditions; and detecting which probe molecules have hybridized with said target nucleic acid.

In an aspect, in the fifth embodiment the terminal subsequence of said target nucleic acid is single-stranded, and wherein said hybridization region of said probe molecules hybridizes to said single-stranded end subsequence. In an aspect, in the fifth embodiment the terminal subsequence of said target nucleic acid comprises a single-stranded end subsequence and an adjacent double-stranded subsequence, and wherein said hybridization region of said probe molecules hybridizes to said single-stranded end subsequence and to a strand of said adjacent double-stranded subsequence, whereby a stand of said target nucleic acid is displaced from said double-stranded region.

According to a sixth embodiment, the instant invention includes a method for binding probe molecules on a glass surface comprising: preparation of said glass surface comprising washing with an acid of a pH of no more than 1; amino-reactive-derivitizing said prepared surface with amino-reactive groups; contacting said derivitized surface with a solution of probe molecules in order to deposit said probe molecules, wherein said solution has a concentration of probe molecules of less than 200 micro-moles per liter, and wherein said probe molecules comprise an amino functional group and a subsequence of at least 16 oligonucleotides; and passivating amino-reactive groups on said contacted surface.

In an aspect, in the sixth embodiment the acid comprises nitric acid of a concentration of at least 65%. In another aspect, the step of amino-reactive-derivitization comprises: amino-derivitizing said prepared surface with amino groups by immersion in an amino containing silane; and conjugating amino-reactive groups to said amino groups on said surface by immersion in phenylene diisothiocyanate.

According to a seventh embodiment, the instant invention includes a method for differential gene expression analysis comprising: applying the method of first embodiment to a nucleic acid sample derived from a first tissue; applying the method of the first embodiment to a nucleic acid sample derived from a second tissue; and comparing the nucleic acids identified in these two steps. In an aspect, in the seventh embodiment, the first tissue comprises a particular tissue in a first state, and wherein said second tissue comprises said particular tissue in a second state.

According to a eighth embodiment, the instant invention includes a detection array according to the fourth embodiment wherein probe molecules are bound to a surface according to the method of the sixth embodiment.

According to a ninth embodiment, the instant invention includes a kit comprising in separate containers: first reagents for providing a subsample of first nucleic acid fragments from an original sample of nucleic acids, said first nucleic acid fragments in said subsample being derived from those nucleic acids in said original sample having selected sequences for a first and a second primary nucleotide subsequence; second reagents for providing second nucleic acid fragments from said subsample of first nucleic acid fragments, wherein said second nucleic acid fragments have an additional subsequence comprising a terminal single-stranded subsequence of said second nucleic acid fragments, and wherein said additional subsequence is at a fixed distance from said first primary subsequence; and a detection array according to the fourth embodiment for recognizing said additional subsequences of said second nucleic acid fragments.

In an aspect, the ninth embodiment includes a computer readable medium containing instructions for causing a computer to search a database of nucleic acid sequences for those sequences having said first primary nucleotide subsequence, second primary nucleotide subsequence, and said additional nucleotide subsequence.

According to a tenth embodiment, the instant invention includes a computer-based system for processing gene-expression information comprising: input/output means for input of user requests and output of processing responses; storage means for storing nucleic acid sequences identified in samples of nucleic acids according to the method of first embodiment; and processing means for, according to said user requests, either searching a database of nucleic acid sequences in order to locate database sequences having said observed subsequence sets or to determine that no such database sequences exist, said database of nucleic acid sequences comprising nucleic acid sequences that might be present in said sample, and storing said located database sequences in said storage means, or for comparing two or more sequences retrieved from said storage means, said sequences having been identified in two or more samples of nucleic acids, in order to determine differential presence of said identified database sequences in said samples, and generating processing responses of said searching or of said comparing.

The practice of the present invention employs, unless otherwise indicated, conventional techniques of cell biology, cell culture, molecular biology, microbiology, recombinant DNA, immunology, transgenic animal technology, and pharmacology. See, e.g., Sambrook et al., *Molecular Cloning A Laboratory Manual,* Cold Spring Harbor Press, (2nd. ed., 1989); Glover ed., *DNA Cloning,* Vol 1 and 2 (1985); Gait ed., *Oligonucleotide Synthesis* (1984); Hames et al. eds., *Transcription and Translation* (1984); Freshney, *Culture of Animal Cells,* Alan N. Liss, Inc. (1997); *Immobilized Cells and Enzymes,* IRL Press (1986); Perbal, *A Practical Guide to Molecular Cloning Methods in Enzymology,* Academic Press (1984); Miller et al. eds., *Gene Transfer Vectors for Mammalian Cells,* Cold Spring Harbor Laboratory (1987); Wu et al. eds., *Methods in Enzymology,* Vols 154 and 155; Mayer et al. eds., *Immunochemical Methods in Cell and Molecular Biology,* Academic Press (1987); Weir et al. eds., *Handbook of Experimental Immunology,* Vols 1–4 (1986). All of these references are incorporated herein by reference in their entirety.

4 BRIEF DESCRIPTION OF THE DRAWINGS

These and other features, aspects, and advantages of the present invention will become better understood by reference to the accompanying drawings, following description, and appended claims, where:

FIG. 1 illustrates a preferred subsequence set;

FIG. 3 illustrates a preferred phasing PCR primer;

Figure 5A:
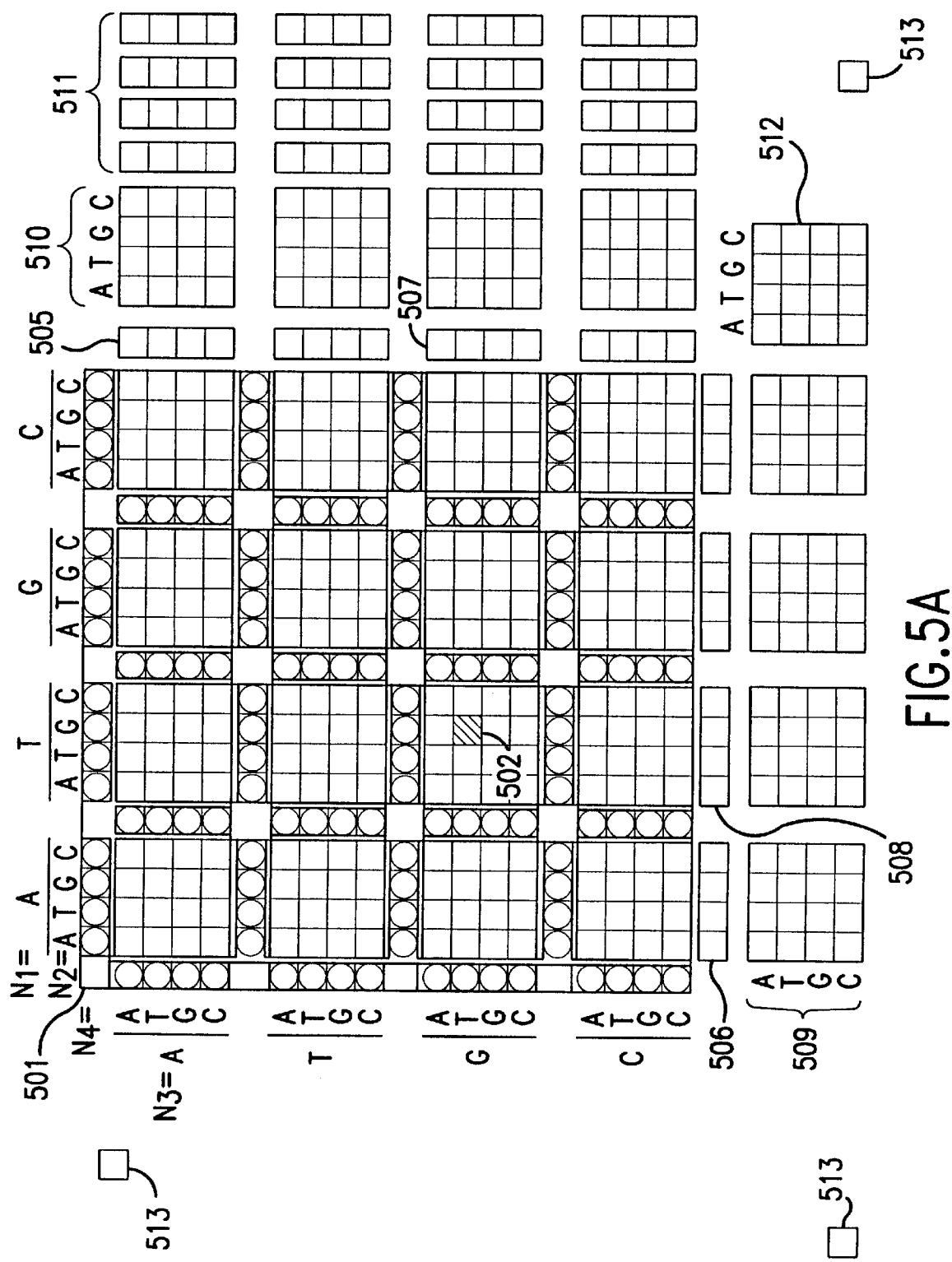
Figure 6A:
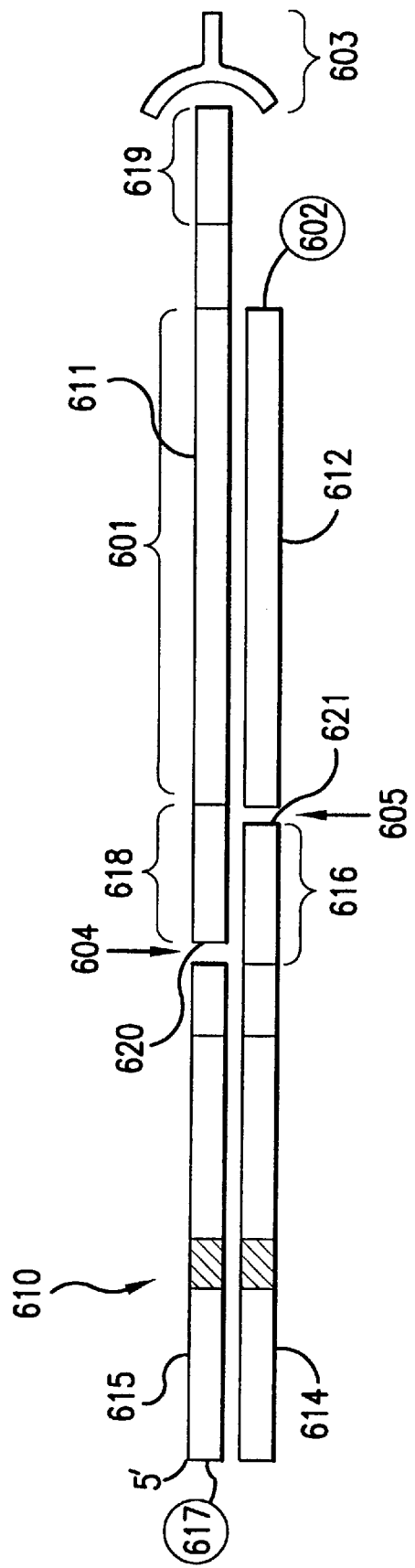
Figure 6B:
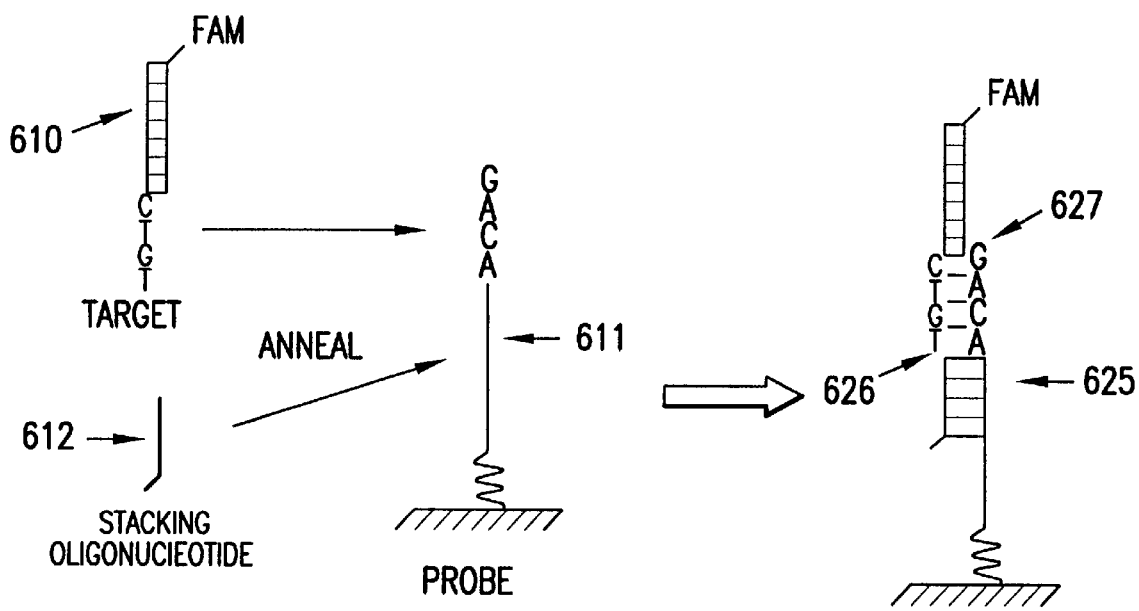
Figure 6B:
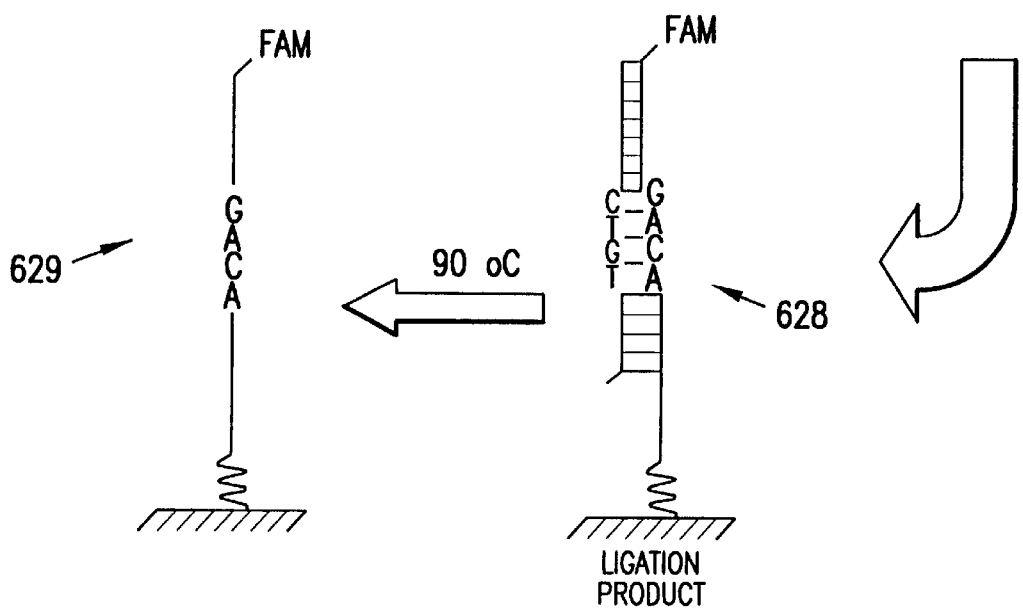
Figure 7A:
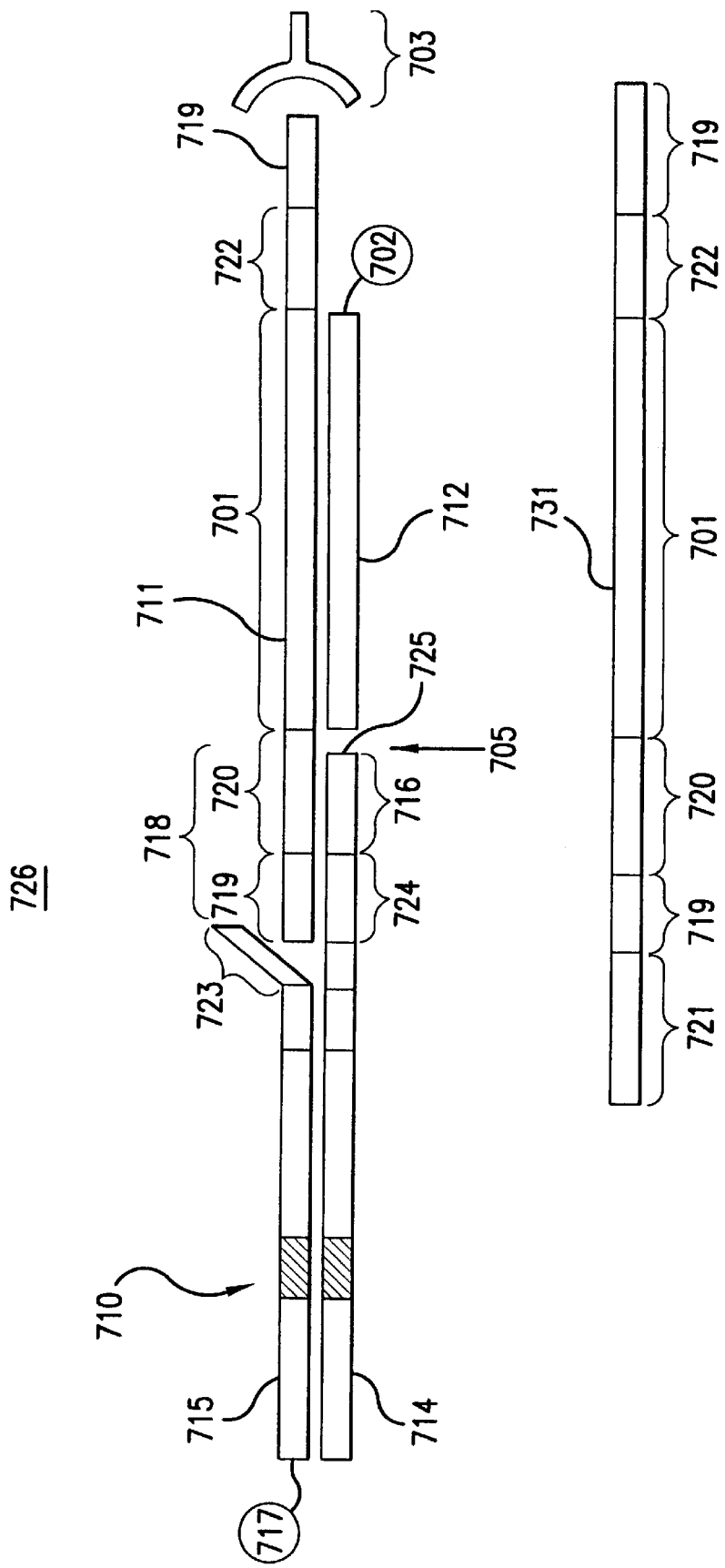
Figure 7B:
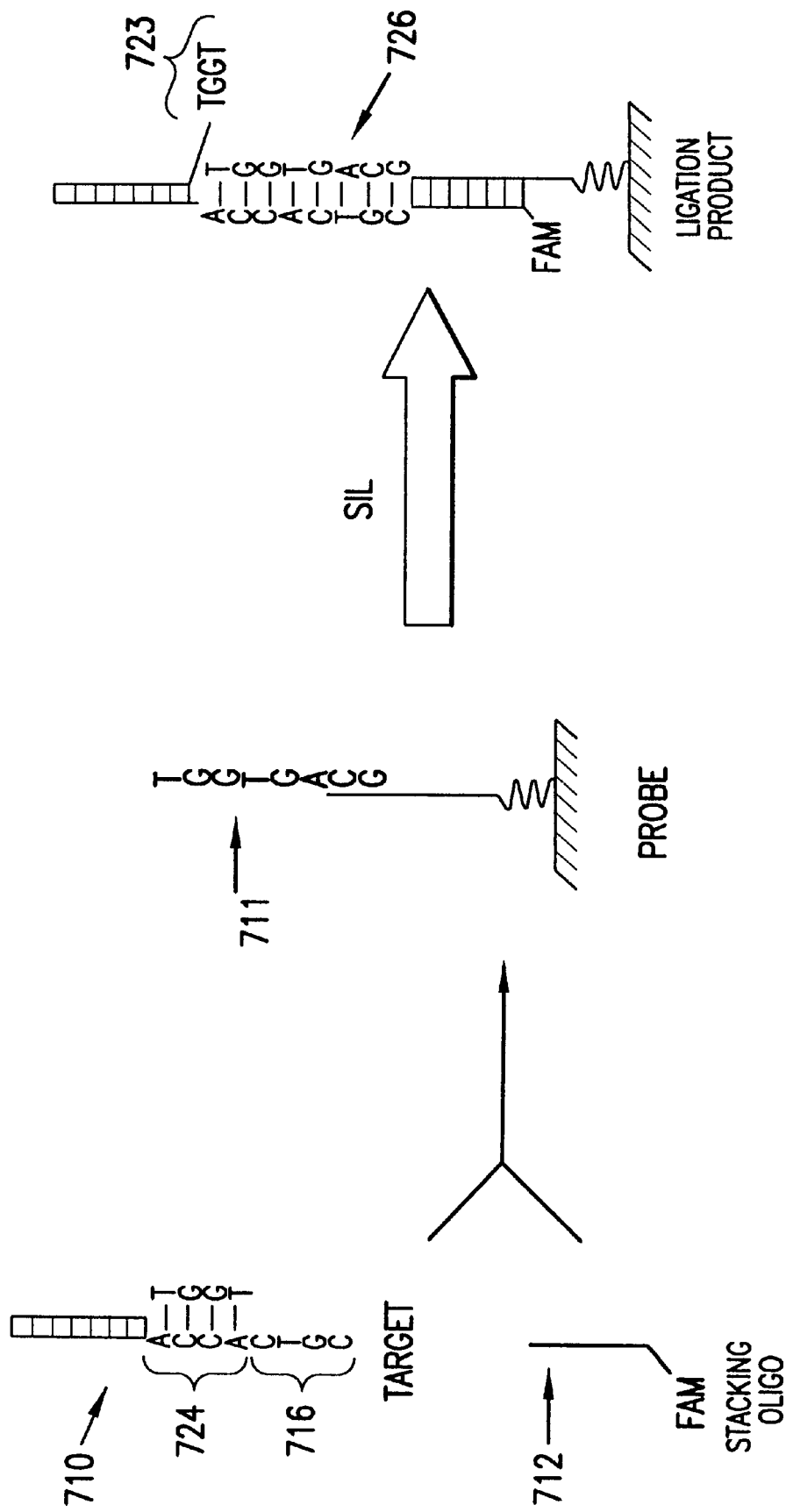
Figure 8:
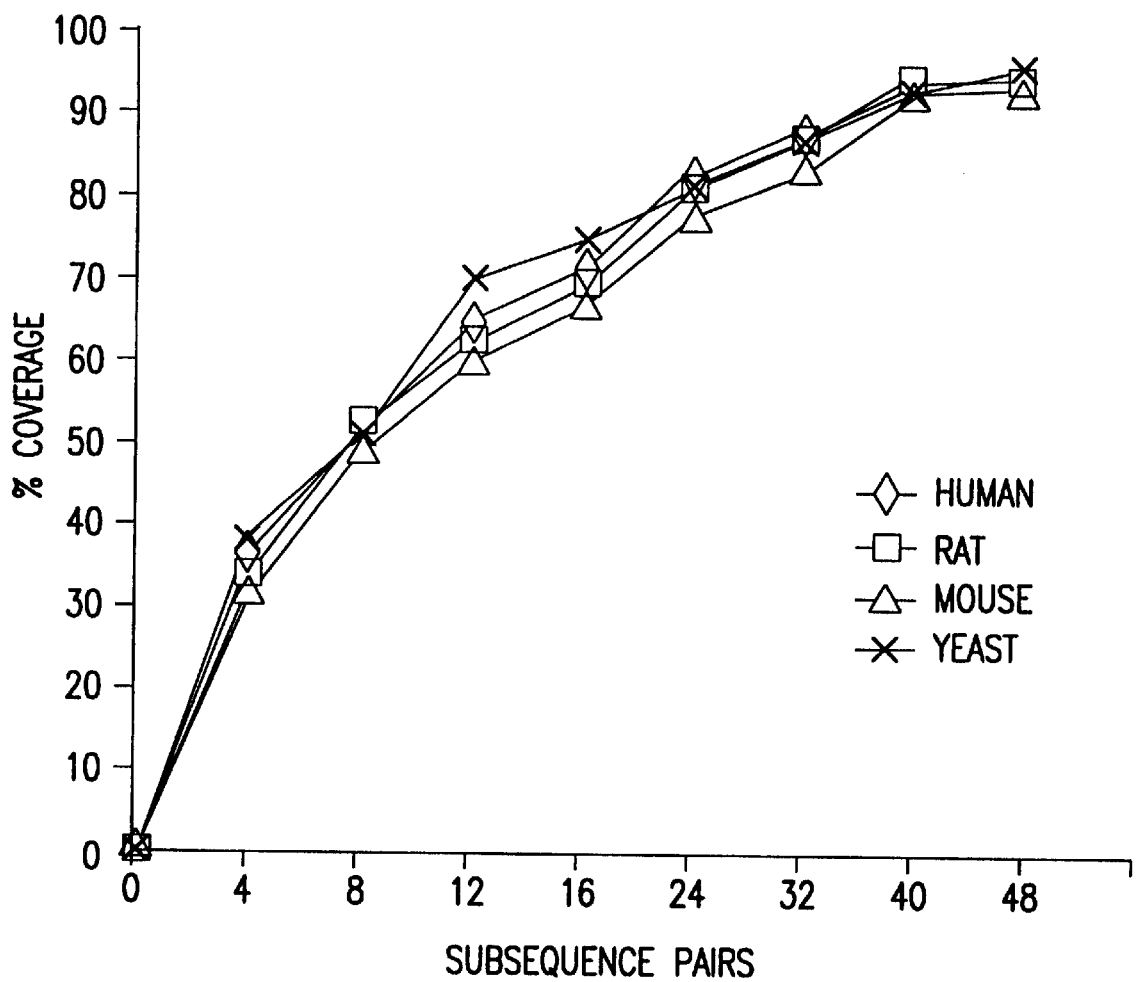
Figure 9A:
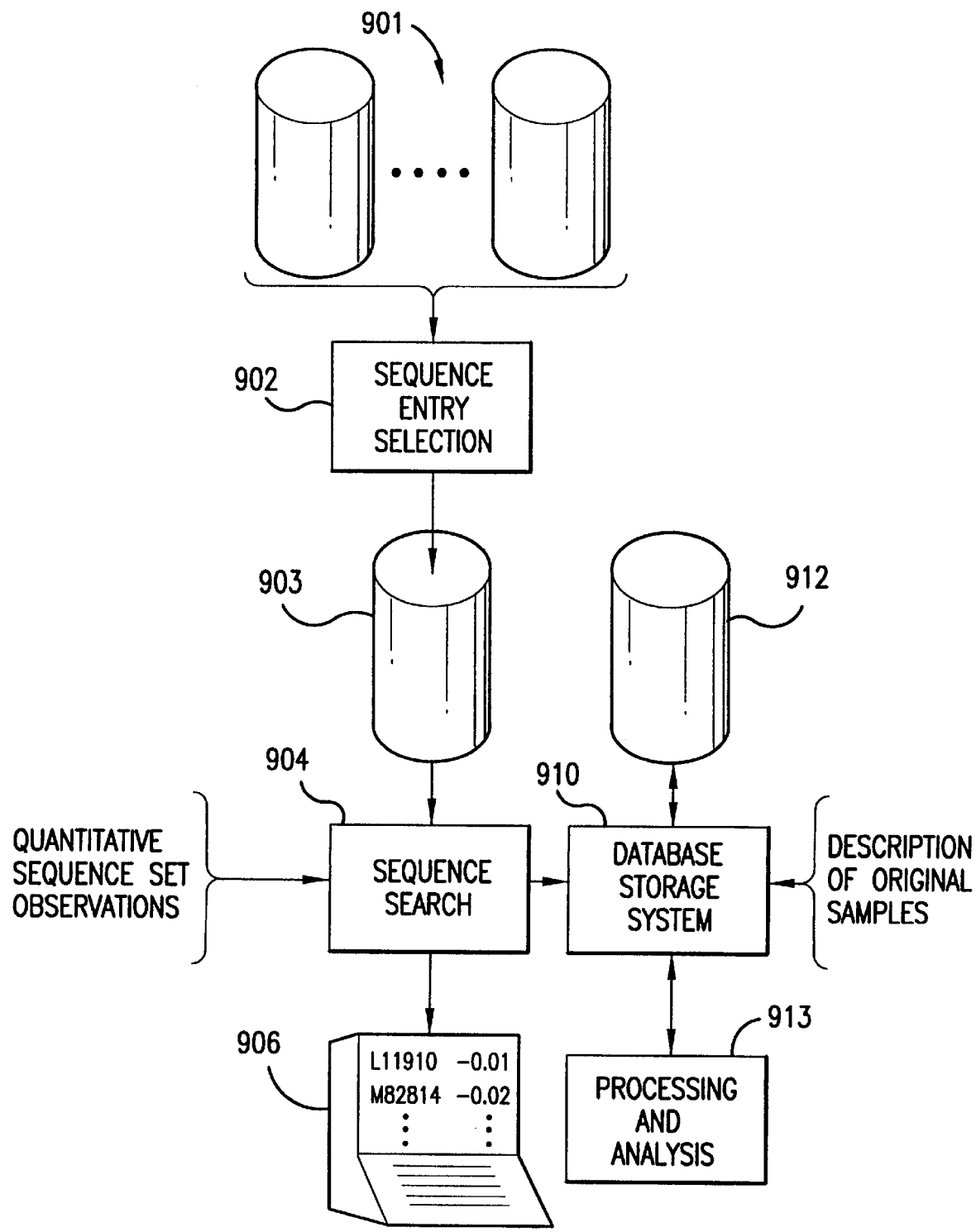
Figure 9B:
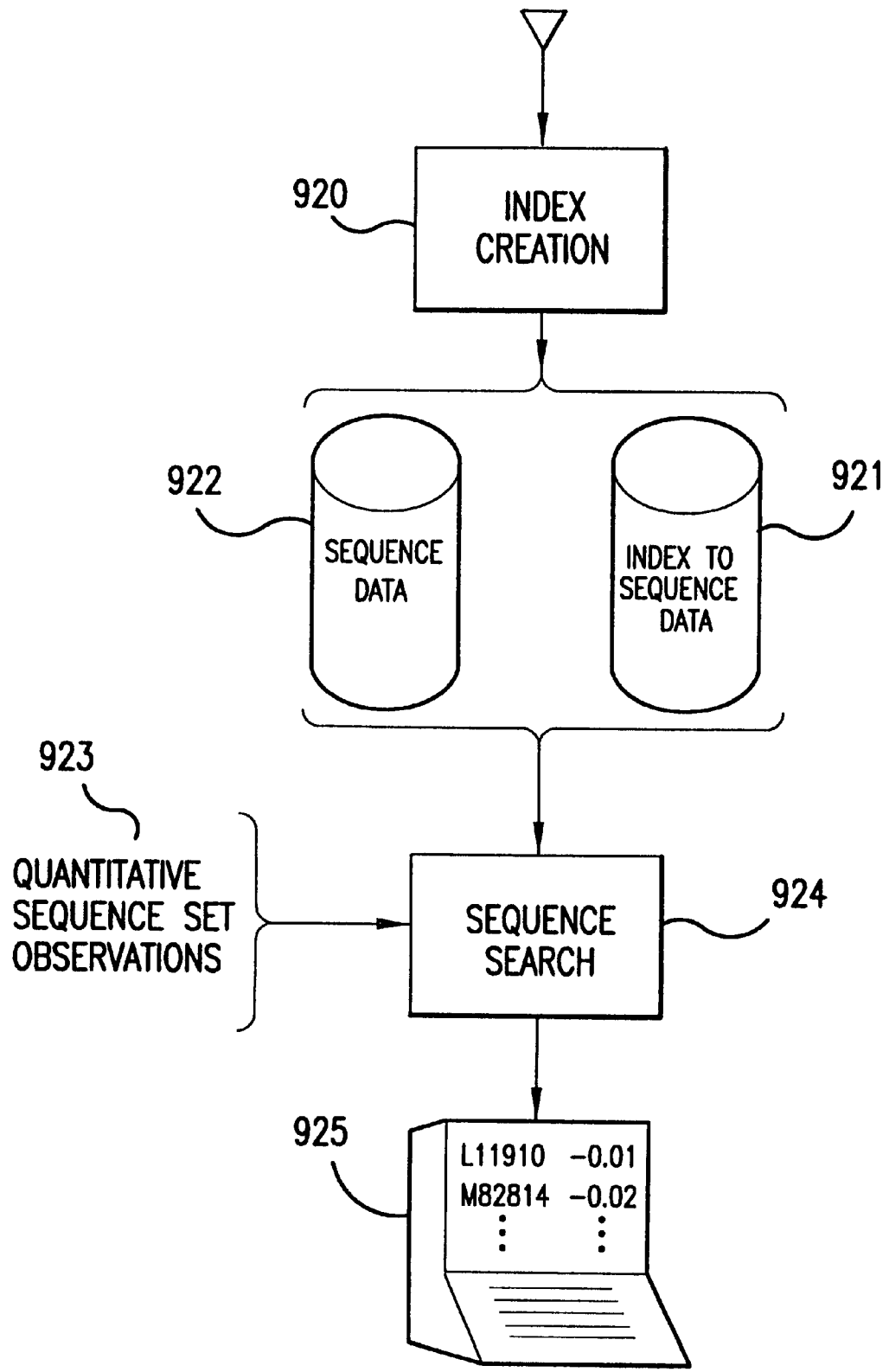
Figure 10:
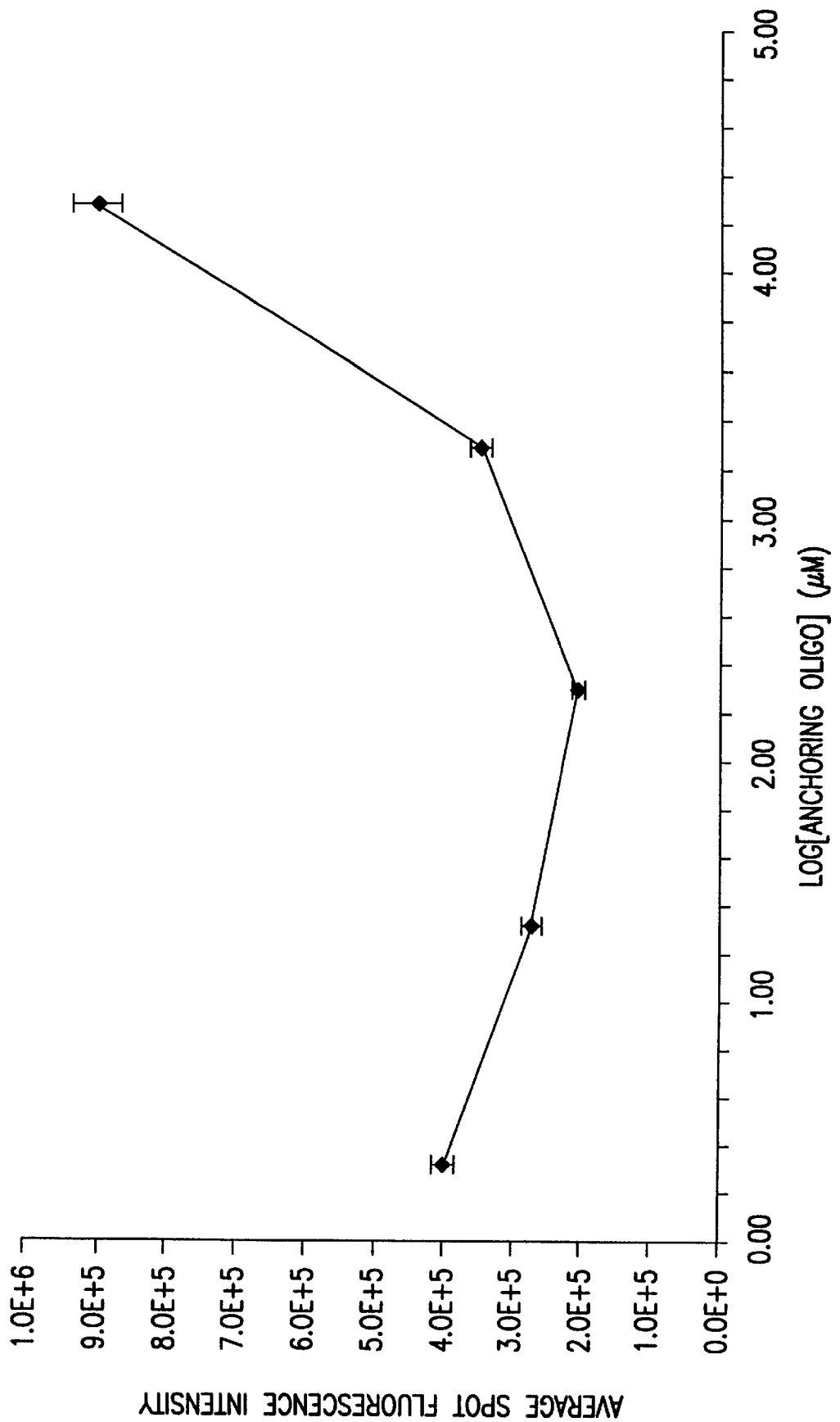
Figure 11:
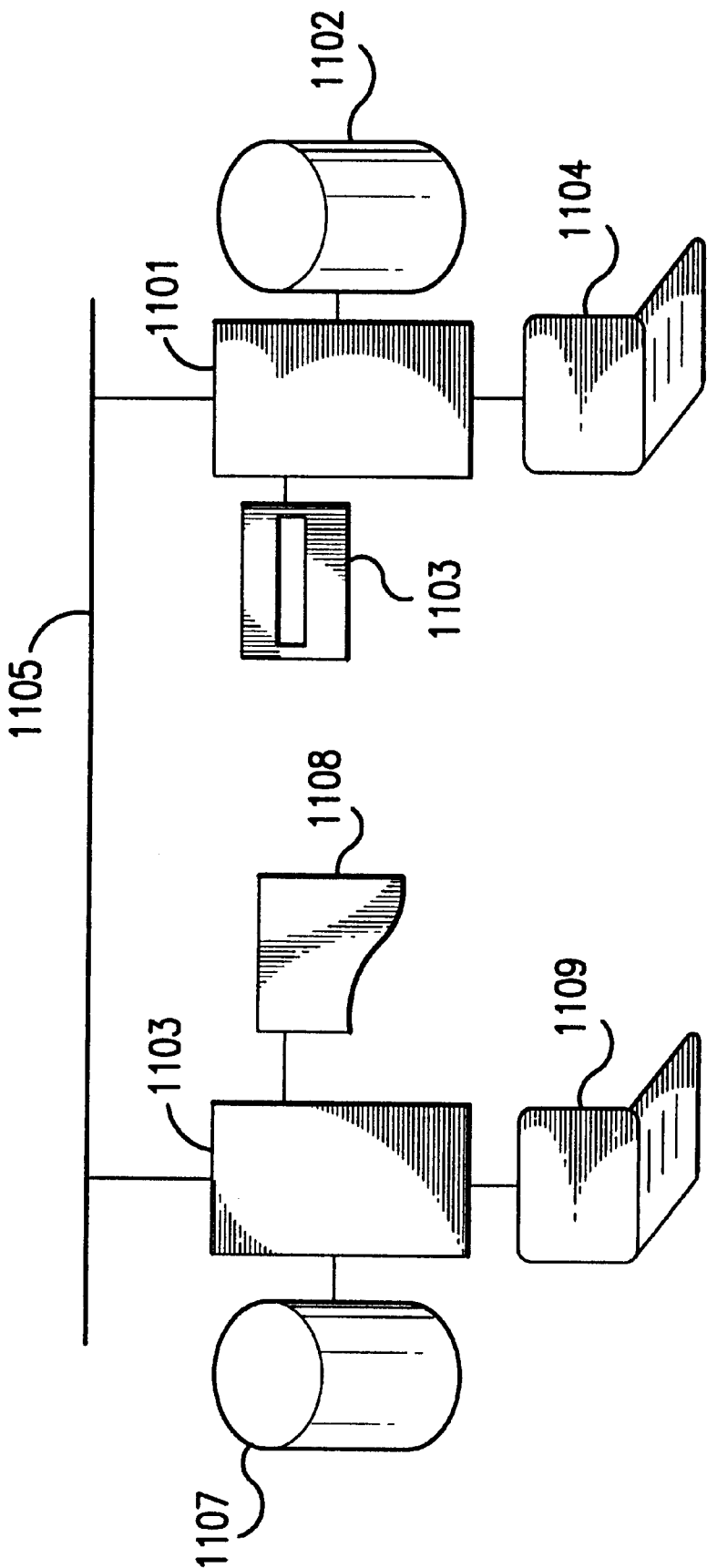

FIGS. 5A–B illustrate a preferred physical structure for a universal detection array of this invention;

FIGS. 6A–B illustrate a use of a universal detection array according to direct ligation;

FIGS. 7A–B illustrate another use of a universal detection array according to strand-invasion;

FIG. 8 illustrates the results of an experiment relating to coverage of a preferred observational method of this invention;

FIGS. 9A–B illustrate a preferred embodiment of the database search methods of this invention;

FIG. 10 illustrates results from a test of the preferred observational method of this invention; and FIG. 11 illustrates an exemplary computer system for performing methods of this invention.

5 DETAILED DESCRIPTION

The instant invention relates to methods and devices for identifying and quantifying nucleic acids in a sample of nucleic acids (also referred to herein as "gene-calling"), and in particular to methods and devices for genomic analysis. Accordingly, this invention can be applied to analysis of gene expression by identifying and quantifying complementary DNA ("cDNA") and to genetic analysis by identifying and quantifying genomic DNA ("gDNA").

The gene-calling methods of this invention start, in general, with a possibly complex sample of nucleic acids, preferably DNAs, and observe the presence of sets of nucleotide subsequences ("subsequence sets") in the nucleic acids of the sample. Then with reference to a database of nucleotide sequences of nucleic acids that may be in the original sample, the methods determine which sequences have the observed subsequence sets, and which observed subsequence sets are not present in any sequence in the database. Accordingly, nucleic acids in the original sample are either identified or marked as possibly novel. In preferred embodiments, methods quantitatively identify the presence of subsequence sets in order that nucleic acids can in turn be quantitatively identified.

A subsequence set includes at least two, non-adjacent nucleotide subsequences in a nucleic acid. Preferred embodiments observe a subsequence set by observing two "primary" subsequences and an "additional" subsequence. In case the additional subsequence and one of the primary subsequences are adjacent, these subsequences can be considered a single subsequence, and the subsequence set includes only two subsequences. Equivalently, in this case the subsequence set can be considered as including three subsequences, which are the two primary subsequences and the additional subsequence. In case the additional subsequence is not adjacent to either of the primary subsequences, the subsequence set includes these three subsequences.

In a preferred embodiment, the methods of this invention observe the primary and the additional subsequences sequentially in at least two steps. The preferred methods first produce one or more less complex subsamples of nucleic acid fragments, each nucleic acid in a subsample being derived from those nucleic acids in the original sample which include the two initially specified, primary subsequences in the original nucleic acid. These subsamples are produced from the original sample in a manner which is repeatable and results in predictable fragments. Several such limited-complexity subsamples (defined by different primary subsequences) can be produced, all of which together adequately sample all the nucleic acids in the original sample. Next, the preferred embodiment observes (or recognizes) the additional subsequence in each fragment of the subsample. This subsequence can be from 4, to 8, to 10 or more base pairs ("bp"), and is preferably 5, 6, or 7 bps.

Finally, the methods of this invention comprise computer-implemented nucleic acid database searches, which determine less than 5–10, and preferably only one, candidate sequences that could produce a fragment in the particular predictable manner and that also includes the particular additional subsequence. In other words, the computer-implemented methods determine which database sequences have the observed sequence sets. Thereby, nucleic acids in the original sample are determined. Preferably, at least the determination of the additional subsequence returns quantitative information of the relative abundance of the particular fragments in order that the abundance of the nucleic acids in the sample can be quantitated. In a preferred embodiment, the initially specified subsequences are recognition sites for Type II restriction endonucleases ("RE") (an RE cutting a double stranded nucleic acid within its recognition site), and the additional subsequence is determined as the sequence of an overhang produced by digestion by a Type IIS restriction endonuclease (an RE cutting a double stranded nucleic acid outside of its recognition site).

This invention also relates to devices which allow the rapid and high-throughput determination of this additional subsequence without requiring conventional cloning and/or sequencing and the attendant cumbersome electrophoretic separations required, and to methods for the use of such devices. These devices are based on novel implementations and uses of arrays of oligonucleotides preferably attached to a planar surface, such as a glass chip (also referred to herein as "universal detection arrays"). These arrays are adapted to the specific and reliable determination of short single strand overhangs and include error checking structures to minimize false positives. Reliability is enhanced by the use of enzymatic recognition of correct hybridization, such as by a ligase, as well as by the use of energetic hybridization assists, such as by base stacking and strand-invasion. These arrays are used in the general gene-calling methods of this invention according to implementations which include ligation alone as well as strand-invasion with ligation. Advantageously, these arrays permit the parallel and quantitative determination of additional subsequences in all the fragments of a subsample without the need to separate the individual fragments.

In the following, the methods for gene calling are first generally described in Section 5.1 followed in Section 5.2 by a description of the universal detection arrays and their methods of use.

5.1 Methods for Gene-Calling

Generally, the methods for gene-calling, and also for identifying particular nucleic acids, in a sample of a plurality of nucleic acids, proceed, first, by determining, or recognizing, the presence of a set of nucleotide subsequences ("subsequence set") in a nucleic acid of the sample, and second, by using such a determination to actually identify that nucleic acid with reference to a database of sequences of nucleic acids that might be present in the sample. The subsequence set preferably consists of two primary subsequences and an additional subsequence. Additionally and importantly, where one or more of the physical signals by which a subsequence set is identified provide also a quantitative indication of the amount of the containing nucleic acid, these methods can be applied to the valuable task of determining the relative levels of gene expression, as well as simply identifying the presence of a particular nucleic acid.

This section describes, first, general requirements on the subsequence set, in particular on the preferable lengths of the subsequences, and second, various applications of the general method of gene-calling. Next, this section describes in separate subsections the principal steps of a preferred method of gene-calling. The principal steps includes: generation of subsamples of nucleic acid fragments from original nucleic acids having specified primary subsequences; determination of an additional subsequence in generated fragments; search of a database of nucleotide sequences; and optionally, confirmation steps.

Gene-Calling Methods in General

Turning now to a preferred structure for subsequence sets, FIG. 1 generally illustrates a subsequence set in nucleic acid 101 present in the original sample. A subsequence set is described herein without limitation as being a set of three nucleotide subsequences with particular positional constraints. It will become apparent to one of average skill in the art upon study of this description and accompanying examples that the general methods of this invention can be applied to subsequences sets having different numbers of subsequences with different positional constraints between the elements.

Turning to the described embodiment, a subsequence set comprises three subsequences: primary subsequences 102 and 104, also called herein subsequences S1 and S2, together with additional subsequence 103, also called herein subsequence A1. The positional constraints include the following. Primary subsequence 102, S1, and additional subsequence 103, A1, are constrained to be a fixed number of nucleotides, or distance, apart. Preferably S1 and A1 are adjacent. On the other hand primary subsequence 102, S1, and primary subsequence 104, S2, are not constrained to be a fixed distance apart. Finally, additional subsequence 103, A1, is constrained to lie between primary subsequences 102, S1, and 104, S2. Although these three subsequences are illustrated in FIG. 1 as if they are internally contiguous, this invention is not so limited. For example, in the case where these subsequences are recognized as being the binding sites of REs (or of other DNA binding proteins) (also known herein as a "recognition site"), these subsequences may be interrupted by one or more undetermined nucleotides. REs possessing interrupted recognition sites (for example, interrupted palindromic REs) are well known in the art.

The lengths of the subsequences are chosen, in general, to insure adequate resolution and separation of the gene-calling methods of this invention. Resolution of gene-calling methods is herein taken to mean how uniquely a nucleic acid in the original sample can be identified with respect to a database of nucleic acid sequences likely to be present in the sample. It is preferable that each nucleic acid in the sample be identified as originating from no more than approximately ten candidate nucleic acid sequences in such a database, more preferably from no more than approximately five candidate nucleic acid sequences, and most preferably from no more than approximately one candidate nucleic acid sequence. Resolution depends on how many sequences on average in the database share a particular subsequence set with the same particular subsequences. Separation of gene-calling methods is herein taken to mean how uniquely a particular subsequence set can be recognized by the particular observational methods. It is preferable that each observation is produced by no more than two nucleic acids with a particular subsequence set. Most preferably each observation uniquely identifies a nucleic acid with a particular subsequence set. Separation depends on the particular observational methods and is discussed below with respect to particular embodiments of these methods.

In the following paragraphs, subsequence length preferences in view of adequate resolution are first discussed followed by the subsequence length preferences in view of adequate separation. Finally, overall length preferences in view of both goals are discussed.

Concerning resolution, the longer the subsequences—S1, S2, and A1—the better the resolution with respect to a sequence database of a certain complexity. Complexity of a sequence database or of a sample of nucleic acids is taken herein to mean the total length in nucleotides of the sequences in the database or in the sample. Resolution improves with longer subsequences, because fewer database sequences share any particular longer subsequence. In the case application of the instant method to expressed DNA sequences, that is of cDNA samples, an analysis similar to the following leads to preferable subsequence lengths. One of skill in the art will be able to adapt the following analysis to nucleic acid samples of differing complexity, such as genomic or expressed nucleic acids from various organisms.

Table 1 is an exemplary approximate analysis of resolution requirements for subsequence lengths for the case of the expressed human genome. For constructing this table, the human genome is taken to consist of approximately 100,000 sequences of approximately 3,000 nucleotides length. See, e.g., U.S. Pat. No. 5,459,037. This invention is not limited to the exemplary values illustrated in Table 1. Upon reading the following description, one of ordinary skill will understand how to adapt this invention to other values for Table 1.

TABLE 1

| Sum of the lengths of S1 and A1 | Probability ($\times 10^{-4}$) | Resolution (if length S2 is 6) | Resolution (if length of S2 is 7) |
| --- | --- | --- | --- |
| 10 | 28.4 | 28 | 7 |
| 11 | 7.1 | 7 | 2 |
| 12 | 1.8 | 2 | 0.5 |
| 13 | 0.44 | 0.5 | 0.1 |

In this table, the first column sets out possible exemplary values for the sum of the lengths of S1 and A1. The second column sets out the approximate probability of finding S1 and A1 in a fixed relative position in a typical expressed sequence of length 3,000 nucleotides. The third column sets out the approximate number out of the 100,000 genes that contain S1, S2, and A1 in case the length of S2 is 6 nucleotides. The fourth column has the same values in case the length of S2 is 7 nucleotides.

This table is constructed in the following manner. Since primary sequence S1 and additional sequence A1 are constrained to be in a fixed relative position, the probability of their occurrence in a 3000 base length of nucleic acid is approximately 3000 divided by 4 raised to the power which is the sum of the length of S1 and the length of A1, as is well known to those of ordinary skill. This probability and subsequent probabilities are estimated by assuming subsequences are randomly occurring. This and subsequent tables and analyses can be refined by using exact probabilities obtained from scanning nucleotide sequence databases for observed probabilities. For example, if the length of S1 is 6 and the length of A1 is 5, then the probability is $3000/4^{-(6+5)}$, or $3000/4^{-11}$, which is $7.1 \times 10^{-4}$. In case, the length of S2 is 6, the probability of finding S2 at any distance from S1 and A1 is a complex function depending in the exact sequence of S2. Herein, this probability is conservatively taken to be approximately $\frac{1}{8}$ (ignoring positional constraints), which results from assuming that S2 can have approximately 500 independent positions with respect to S1 and A1 in a sample nucleic acid ($\frac{1}{8} = 500/4^6$). Therefore, the resolution, or the number of database sequences containing this sequence set, is the probability in column 2, multiplied by 100,000, and further multiplied by $\frac{1}{8}$. In case the length of S2 is 7, the probability of S2 is taken to be $\frac{1}{32}$.

Accordingly, for this exemplary analysis, it is preferred for the sum of the lengths of S1 and A1 to be at least 11 and for the length of S2 to be at least 6. Alternately, it is preferred for the sum of the lengths of S1 and A1 to be at least 10 and for the length of S2 to be at least 7. It is more preferred for the sum of the lengths of S1 and A1 to be at least 12 and for the length of S2 to be at least 6. Alternately, it is preferred for the sum of the lengths of S1 and A1 to be at least 11 and for the length of S2 to be at least 7. The length of additional subsequence A1 is not limited to be the length of the single-stranded overhang of a Type IIS RE. For example, a UDA used according to strand-invasion ligation recognizes terminal subsequences including short double-stranded portions.

More particularly, where the subsequences are recognized by restriction endonucleases ("REs"), S1 and S2 can be preferably recognized by Type II REs with six base pair recognition sites, and A1 can be the sequence of the overhang generated by a Type IIS RE that produces a five base overhang. HgaI is such a Type IIS RE (New England Biolabs, Beverly, Mass.). More preferably, the Type IIS RE produces a six base overhang. Cje1 and CjePI are similar REs which cut outside their recognition region, however on both sides of this region. (Vitor et al., Gene 157:109–110 (1995)).

Next, criteria related to separation are discussed with respect to a particular observational method. For the sake of illustration only, and without limitation, these criteria are discussed with respect to a preferred observational method, which generally proceeds according to two steps. From study of the subsequent description, one of ordinary skill will know how to adapt these criteria and this invention to other observational methods. Such alternative methods might simultaneously recognize all subsequences of a subsequence set, for example by including a step of simultaneous hybridization of three distinguishably labeled probes to the sample of nucleic acids.

According to the preferred two step method, first, a subsample of nucleic acids, or of nucleic acid fragments, is produced from an original sample by selecting only those nucleic acids that have two selected primary sequences, S1 and S2. By varying the selected S1 and S2, a sufficient plurality of subsamples can be produced which adequately sample the nucleic acids in the original sample (see below for a description of "coverage"). Second, additional subsequence A1, in a fixed relation to S1, is determined on the fragments in the subsample. A preferred embodiment of this two step observational method is discussed below in Sections 5.1.1 and 5.1.2. The ease of unambiguously determining additional sequence A1, and hence the quality of separation, depend on the number of fragments in the subsample. The fewer the number of fragments in a subsample, the fewer possible additional subsequence A1 that need to be unambiguously determined. Further, the number of fragments in the subsample depends primarily on the lengths of primary subsequences S1 and S2, which are used to select the subsample.

Table 2 is an exemplary analysis of the number of fragments in a subsample versus primary subsequence lengths. For constructing this table, approximately 10,000 sequences of approximately 3,000 nucleotides length are taken to be expressed in a typical human tissue. This invention is not limited to the exemplary values illustrated in Table 2. Upon reading the following description, one of ordinary skill will understand how to adapt this invention to other values for Table 2.

TABLE 2

| Length of S1 | Length of S2 | Probability (×10⁻⁴) | Number of fragments in subsample |
|---|---|---|---|
| 6 | 6 | 0.091 | 910 |
| 6 | 7 | 0.011 | 110 |
| 7 | 6 | 0.011 | 110 |
| 7 | 7 | 0.0014 | 14 |

In this table, the first two columns set out possible values for the lengths of S1 and S2. The third column sets out the approximate probability of finding S1 and S2 in any relative position in a typical expressed sequence of length 3,000 nucleotides. The fourth column sets out the approximate number of fragments that contain S1 and S2 in a subsample arising from an original expressed sample of 10,000 expressed sequences.

This table is constructed quite similarly to Table 1. The probability of any nucleic acid of length 3000 nucleotides from the original sample containing primary sequences S1 and S2 in any relation is the probability of finding S1 anywhere in a 3000 base length of nucleic acid multiplied by the probability of finding S2 in any relation to S1 in such a nucleic acid. As previously, this first probability factor is approximately 3000 divided by 4 raised to the power which is the length of S1. Also as previously, this second probability factor is a complex function which is taken (again ignoring positional constraints) to be $1/8$ in case the length of S2 is 6, and to be $1/32$ in case the length of S2 is 7. For example, if the lengths of S1 and S2 are 6 then this probability is $(3000/4^{-6}) \times (1/8)$, which is 0.091. Finally, the number of fragments in a subsample is the probability of column three multiplied by 10,000.

Table 2 is useful in assessing methods to determine additional subsequence A1. A preferred method for this determination has certain important properties. One important property necessary for high-throughput of the overall gene-calling method is that a subsequence determination method be able to determine all the sequences in a subsample simultaneously and in parallel. Any method that requires cloning, separation, separate handling, or separate sequencing of the fragments of a subsample is less preferable. Also, electrophoretic separation steps are also less preferable since they typically require manual preparation steps. Clearly the ability to determine subsequences in a subsample in parallel is dependent on the number of possible subsequences, as reflected in the total number of fragments in a sample. The fewer the fragments the easier the parallel subsequence determination. On the other hand, fewer fragments in a subsample require production of more subsamples in order to adequately sample the nucleic acids in the original sample. Consequently, it is preferable to have subsamples which are at the parallel detection limit of a subsequence determination method.

A second important property is that a subsequence determination method be able to determine both the nucleotide sequence and also the quantitative presence of additional subsequence A1. When coupled with methods of producing subsamples that result in amounts of subsample fragments being quantitatively determined by original nucleic acid amounts, such determination method permit quantitative gene expression analysis. Quantitative gene expression is one important application of this invention.

This invention is adaptable to any method for determining additional subsequences, which preferably has the previous important parallel and quantitative characteristics. However, for the sake of illustration only, and without limitation, this invention is discussed in the following primarily with respect to a preferred observational method, which generally proceeds by hybridizing the fragments of the subsample to a set of probes, such as degenerate oligonucleotides, capable of hybridizing with all additional subsequences that might be present in the subsample. In addition, peptido-nucleic acids ("PNAs") can be used as probes. From study of the subsequent description, one of ordinary skill will know how to adapt these criteria and this invention to other observational methods. Such alternative methods might simultaneously recognize all subsequences of a subsequence set, such as by including a step of simultaneous hybridization of three distinguishably labeled probes to the sample of nucleic acids.

A set of oligonucleotides capable of hybridizing with all additional subsequences that might be present in the subsample, especially when such a set is arrayed on a planar surface, is called herein a "universal detection array" ("UDA"). A UDA achieves parallel determination of additional subsequences because all fragments in the subsample hybridize simultaneously to the probes of the array.

To achieve preferred separation characteristics, that is to determine subsequences as uniquely as possible, the number of different oligonucleotides in a UDA is important. The number of different oligonucleotides in a UDA necessary to determine an additional subsequence of length "L" is, of course, $4^L$, the size of such a UDA. Clearly, such a UDA is capable of recognizing no more than $4^L$ fragments in a subsample. Accordingly, for the preferred separation characteristics previously recited, it is preferred that number of fragments in a subsample be no more than twice the size of the UDA being used. It is more preferable that the number of fragments be less than the size of the UDA, and most preferable that this number be substantially less than the size of the UDA.

Table 3 combines the results of Table 1 and Table 2 in order to select appropriate UDA sizes and subsequence lengths having preferable resolution and separation for analysis of the expressed human genome, according to the previously assumed complexities. It is assumed that length of S1 is 6 in Table 3. This invention is not limited to the exemplary values and assumptions illustrated in Table 3. Upon reading the following description, one of ordinary skill will understand how to adapt this invention to other values for Table 3 by combining suitably modified Tables 1 and 2, or by other means.

TABLE 3

| # | A1 length | S2 length (S1 length is 6) | Resolution | Number of fragments in subsample | UDA size (min) | Separation ratio |
|---|---|---|---|---|---|---|
| 1 | 4 | 6 | 28 | 910 | 256 | 3.6 |
| 2 | 4 | 7 | 7 | 110 | 256 | 0.4 |
| 3 | 5 | 6 | 7 | 910 | 1024 | 0.9 |
| 3' | 5 | 6 | 7 | 901 | 4096 | 0.2 |
| 4 | 5 | 7 | 2 | 110 | 1024 | 0.1 |
| 5 | 6 | 6 | 2 | 910 | 4096 | 0.2 |
| 6 | 6 | 7 | 0.5 | 110 | 4096 | 0.1 |

The first column is the row number. The fourth column is the resolution found for the particular subsequence length combination from Table 1. The fifth column is the number of subsample fragments from Table 2. The sixth column is the minimum UDA size appropriate to the length of A1 (that is 4 raised to the power which is the length of A1). Line 3'is discussed separately below. The seventh column is the ratio of the number of fragments in a subsample, from column four, to the appropriate UDA size, from column five. This seventh column reflects separation characteristics. It is preferably less than 2, more preferably less than 1, and most preferably substantially less than 1.

Combinations of subsequence lengths and UDA characteristics can be selected according to Table 3. Only the first row is not suitable to this invention because of the inadequate separation characteristics. The third row is preferred because of adequate resolution, adequate separation, and a relatively larger number of fragments expected in each subsample. The fifth row is more preferred because of improved resolution and separation compared to the third row. Accordingly, in the following, this invention is described for embodiments where the lengths of primary subsequences, S1 and S2, are six, the length of the additional subsequence, A1, is five or six, and the UDA size is 1024 or 4096 as appropriate. These embodiments are then adapted to analysis of expressed human nucleic acid samples.

This invention is not limited to the minimum UDA sizes of Table 3. A UDA used according to strand-invasion ligation can recognize not only a single-stranded terminal but also a short double-stranded subsequence adjacent to a single-stranded terminal subsequence. Thus, a UDA may be chosen larger than indicated in Table 3. For example, with respect to line 3, primary subsequence S1 can be positioned at least one base pair from additional subsequence A1, and a UDA can be used that recognizes 6 bases, 1 base pair of a double-stranded subsequence and 5 bases of a single-stranded terminal subsequence. Line 3' illustrates such a configuration with a UDA has a size of 4096 and a separation ratio of 0.2.

In view of the previous descriptions, one of ordinary skill in the art will understand how to adapt the parameters of these methods, that is how to chose appropriate subsequence lengths and UDA sizes, for nucleic acid samples of differing complexities. For example, different parameters may be appropriate for the analysis of nucleic acid samples from different species and for genomic nucleic acid samples.

Exemplary Applications of Gene-Calling Methods

The following paragraphs describe exemplary, general applications of the methods and devices of the instant invention. Further applications will be apparent to one of ordinary skill in the art in view of the description and examples in the instant disclosure.

Because this invention achieves rapid and economical determination of the quantitative presence of nucleic acids in a complex sample of nucleic acids, it has immediate application to problems relating to the genetic aspects of health and disease in human and other living species. In this application, the sample of nucleic acids is derived from biological sources according to protocols known in the art. For example, nucleic acids samples can include DNA derived from genomic DNA, mitochondrial or other organelle DNA, plasmid DNA, infectious agent DNA, and so forth. Nucleic acid samples can further include RNA derived from total cellular RNA, total cellular mRNA, fractions of mRNA separated from subcellular compartments, infectious agent RNA, and so forth. RNA samples can be advantageously converted into DNA, for example cDNA, by known methods. See. e.g., Ausubel et al., eds., 1997, *Current Protocols in Molecular Biology,* John Wiley & Sons, Inc., New York.

These naturally occurring nucleic acid samples can be derived from living sources of all types. The sources may be in vitro cell lines or cell populations, in vivo tissue samples, such as purified cell populations drawn or derived form wild-type occurrences or to tissue samples containing mixed cell populations, and so forth. The cells and tissues can be derived from all taxonomic classes, including viruses, bacteria and eukaryotes, prokaryotes, protista, plants, fungi, and animals of all phyla and classes. The animals can be vertebrates, mammals, primates, and especially humans. In particular, the animals can be laboratory animals used in research, such as mice or rats engineering or bread to have certain genomes or disease conditions or tendencies. The non-human sources can be subject to various exogenous factors, such as agents, stresses, treatments, and so forth, to determine the effect of such factors. Humans sources can derive from clinical trials, pathological specimens, etc.

These applications can be generally divided into medical applications and research applications. Medical application generally involve examination of known genes of known functions as part of diagnosis or treatment of a patient. Research applications generally involve expression analysis to detect novel genes, novel associations of genes, novel patterns of expression, and so forth.

In more detail, medical applications are of increasing importance as more and more diseases are recognized to have important genetic components to their etiology and development. Therefore, it is becoming increasingly useful to be able to assay the genetic makeup and expression of a tissue sample. For example, the presence and expression of certain genes or their particular alleles can be prognostic or risk factors for disease (including disorders). Several examples of such diseases are found among the neurodegenerative diseases, such as Parkinson's disease, Huntington's disease and ataxia-telangiectasia. The origin or progression of several cancers, such as neuroblastoma, chronic lymphocytic leukemia and other B-cell malignancies, breast and ovarian cancer, and melanoma can now be linked to specific genetic defects (oncogenes and tumor suppressors being now widely known in the art). Finally, gene expression can also determine the presence and classification of foreign pathogens, especially those that might be difficult or impossible to culture in vitro but which nevertheless express their own unique genes.

To observe one or a few expressed, known genomic sequences of interest, primary subsequences are chosen, as described hereinbelow, to generate fragments from the sequences of interest in one of more subsamples, while minimizing fragments generated from sequence not of interest. Then, the additional subsequences distinguishing the sequences of interest are observed. When a UDA is used, hybridization of fragments to oligomers recognizing these additional subsequences is indicative of the presence of the expressed sequence of interest.

Disease progression is reflected in changes in genetic expression of an affected tissue. For example, expression of particular tumor promoter genes and lack of expression of particular tumor suppressor genes is now known to correlate with the progression of certain tumors from normal tissue, to hyperplasia, to cancer in situ, and to metastatic cancer. Return of a cell population to a normal pattern of gene expression, such as by using anti-sense technology, can correlate with tumor regression. Therefore, knowledge of gene expression in a cancerous tissue can assist in staging and classifying this disease.

In this application, this invention is used to compare broadly the expression of genomic sequences in two tissue sources at e.g., two different stages of disease progression or before and after a treatment. Therefore, primary subsequences are chosen, as described hereinbelow, to have the greatest coverage, i.e., that a substantial fraction of all nucleic acids that can be expressed will produce at least one fragment in at least one subsample. Additional subsequences are then determined in the subsamples by quantitative observations. Sequence sets having statistically different presence (as described below) in the two tissue sources are of interest as indicating possible differential gene expression in the two states or stages. When a UDA is used with a planar array of nucleotides producing visual hybridization signals, direct comparison of the optical patterns produced by hybridization with the two sources can identify oligomers with significantly different hybridization signals. Such oligomers recognize additional subsequences for sequence sets with different expression. Further, where the fragments from the tissue sources are distinguishable, differential comparison can be done by simultaneous hybridization of samples from both sources on one UDA.

Expression information can also be used to choose and guide therapy ("pharmacogenomics"). Accurate disease classification and staging or grading using gene expression information can assist in choosing initial therapies that are increasingly more tailored to the precise disease process occurring in the particular patient. Gene expression information can then track disease progression or regression, and such information can assist in monitoring the success or changing the course of an initial therapy. A therapy is favored that results in a regression towards normal or an abnormal pattern of gene expression in an individual, while therapy which has little effect on gene expression or its progression can need modification. Such monitoring is now useful for cancers and will become useful for an increasing number of other diseases, such as diabetes and obesity. Finally, in the case of direct gene therapy, expression analysis directly monitors the success of treatment. Expression differences in samples from tissue sources at different times, subject to different treatments, and so forth are assayed according to this invention as just described.

This invention is also applicable to samples of genomic DNA in a manner similar to its application to cDNA. Medical information of interest in genomic DNA samples includes occurrence and identity of translocations, gene amplifications, loss of heterozygosity for an allele, etc. This information is of interest in, for example, cancer diagnosis and staging or molecular genotyping to predict disease susceptibility and predisposition. In cancer patients, amplified sequences might reflect an oncogene, while loss of heterozygosity might reflect a tumor suppressor gene. Such sequences of interest can be used to select subsequence sets for recognizing the particular genomic changes. Even without prior knowledge of the sequences of interest, detection and classification of patterns of nucleic acid expression is useful for the comparison of normal and diseased states or for observing the progression of a disease state. Gene expression information concerning the progression of a disease state is useful in order to elucidate the genetic mechanisms behind disease, to find useful diagnostic markers, to guide the selection and observe the results of therapies, etc. Differences in the sequence sets observed identify the gene or genes involved, whether known or novel.

In biological research, rapid and economical assay for gene expression in tissue or other samples has numerous applications. Such applications include, but are not limited to, for example, in pathology examining tissue specific genetic response to disease, in embryology determining developmental changes in gene expression, in pharmacology assessing direct and indirect effects of drugs on gene expression. Further, since an unknown sequence set pattern is indicative of an as yet unknown gene, this invention has important use for the discovery of new genes. Additionally, comparative gene-expression information can simplify discovery of detailed disease mechanisms. In medical research, by way of further example, use of the methods of this invention allow correlating gene expression with the presence and progress of a disease and thereby provide new methods of diagnosis and new avenues of therapy which seek to directly alter gene expression.

In more detail, in these applications gene-expression differences between tissue sources from carefully controlled and similar states are assayed as previously described. Importantly, the controlled states are chosen to reduce the complexity of observed changes, preferably such that only a small percentage of the observed sequence sets have changed expression. This small percentage is preferably less than 5% or 1%, and more preferably less than 0.5%. These assays identify sequence sets with different quantitative expression by, perhaps, direct observation of visual hybridization signals from a UDA. The carefully controlled tissue sources can arise from many comparisons. For example, certain cardiovascular tissues can be from a normal laboratory animal and from a similar animal challenged by induced hypertension. Certain immune system tissues can be from a normal animal and from a similar animal challenged with, e.g., bacterial endotoxins. Hepatic tissues can be from a normal laboratory animal and one challenged with a drug or toxin. Tissues can be drawn from embryos at various stages and locations. Cell cultures and cell lines can also be sample sources. For example, samples can be derived from a "normal" cell culture and from the same cell culture subject to such factors as growth factors, signaling moieties, and so forth.

Classification of observed subsequence set patterns, in an exemplary embodiment, can involve statistical analysis to determine significant differences between patterns of interest. This can involve first grouping samples that are similar in one or more characteristics, such characteristics including, for example, epidemiological history, histopathological state, treatment history, etc. Quantitative sequence set observations from similar samples are then compared, e.g., by finding the average and standard deviation of each individual observations. Individual sequence set observations which are of limited variability, e.g., for which the standard deviation is less than the average, then represent genetic constants of samples of this particular characteristic. Such limited variability observations from one set of tissue samples can then be compared to limited variability observations from another set of tissue samples. Sequence set observations which differ in this comparison then represent differences in the genetic expression between the tissue samples and are of interest in reflecting the biological differences between the samples, such as the differences caused by the progression of a disease. Differences in expression are detected, e.g., when the difference in the genetic expression between two tissues exceed the sum of the standard deviation of the expressions in the tissues. Other standard statistical comparisons as are known in the art can also be used to establish levels of expression and the significance of differences in levels of expressions.

5.1.1 Generation of Subsamples

The preferred observational method for determining or recognizing a subsequence set in a sample nucleic acid is comprised of two principal steps. In a first step, one or more subsamples are created from the original sample such that the nucleic acids or nucleic acid fragments in each subsample have particular, selected primary subsequences, S1 and S2. In a second step, an additional subsequence, A1, is determined in each fragment of a subsample, such that A1 is between S1 and S2 and in a fixed relation to S1. Preferably, A1 is adjacent to S1. This subsection describes methods for the first of the two steps of the preferred observational method, and the following subsection describes methods for the second step. For illustrative purposes and without limitation, this description is directed to the preferred implementation where the lengths of S1 and S2 are 6 bps and the length of A1 is 5 to 9 bps, and where the nucleic acids being analyzed are dsDNA. Alternative implementations for recognizing the preferred or alternative sequence set structures are discussed at the end of each section.

Preliminary to description of the first step of the preferred observational method, the important property of coverage of an observational method is next described. Coverage of a particular observational method is taken herein to mean how adequately nucleic acids of interest in the original sample are sampled, or observed, by the observational method. In the case of the preferred method, coverage is determined by the selection of the particular nucleotide subsequences of the primary subsequences which define the plurality of subsamples. Various criteria can be used to guide this selection. For example, in the case where the expression of certain nucleic acids, or known genes, is of interest and is to be measured, a set of particular nucleotide sequences can be selected with respect to such known sequences in order that each nucleic acid of interest will produce at least one fragment in at least one subsample. Preferably, also, the set of subsequences can be selected to minimize fragments produced from nucleic acids in the sample that are not of interest.

Alternately, in the case where the expression of a substantial fraction of nucleic acids, or expressed genes, in a sample are to be measured, a sufficient number of particular nucleotide sequences can be selected so that a substantial fraction of nucleic acids in the original sample produce at least one fragment in at least one subsample. For example, it is preferable that the fraction of nucleic acids sampled should exceed 50%, more preferably 75%, and even more preferably 90%. The fraction sampled can be estimated for a particular selected set of nucleotide subsequences by computer means. For example, such means can scan nucleotide sequences stored in a database of nucleic acid sequences likely to be present in the sample for the presence of pairs of subsequences from the selected set of nucleotide sequences, and then can count the percentage of nucleic acids in the database that have pairs of selected nucleotide sequences. Such nucleic acids generate at least one fragment in at least one subsample.

FIG. 8 presents exemplary output from such computer means for estimating coverage. Here, the particular nucleotide sequences for the primary subsequences were selected from the recognition sequences of Type II REs with 6 bp recognition sites. The vertical axis in FIG. 8 indicates the percent of the database sequences generating at least one fragment in at least one subsample, which is defined here by a pair of Type II REs. The horizontal axis indicates number of RE pair, or particular primary subsequence pairs, each pair representing one subsample. The results graphed in FIG. 8 illustrate that it is possible to achieve 50%, 75%, 90%, or more coverage by recognizing primary subsequences using restriction endonucleases.

The original nucleic acid sample to which the first step of the observational method is applied may derive from any natural or artificial source of nucleic acids. For example, the sample may derive from chromosomal or extra-chromosomal DNA. Chromosomal DNA may be structural genes, regulatory regions, coding regions, non-coding regions, repeated regions, and so forth. In the case of chromosomal DNA an optional fragmentation step can be by, e.g., shearing or sonication (Favello, et al., Methods Cell Biol. 48:551–569 (1995)). Extra-chromosomal DNA may derive from mitochondria, viruses, other parasites or pathogens, plasmids, synthetic constructs, and so forth. RNA samples may include rRNA, tRNA, total cellular mRNA, poly(A) mRNA, specific cellular mRNA fractions, viral RNA, and so forth. As is well known in the art, RNA, in particular mRNA, is advantageously converted for analysis into double-stranded cDNA by methods which are now routine (see, e.g., PCT Publication No. 97/15690, Gubler et al., Gene 25:263–269 (1983), or commercially available kits such as SUPERSCRIPT (Life Technologies, Gaithersburg, Md.)).

Figure 2:
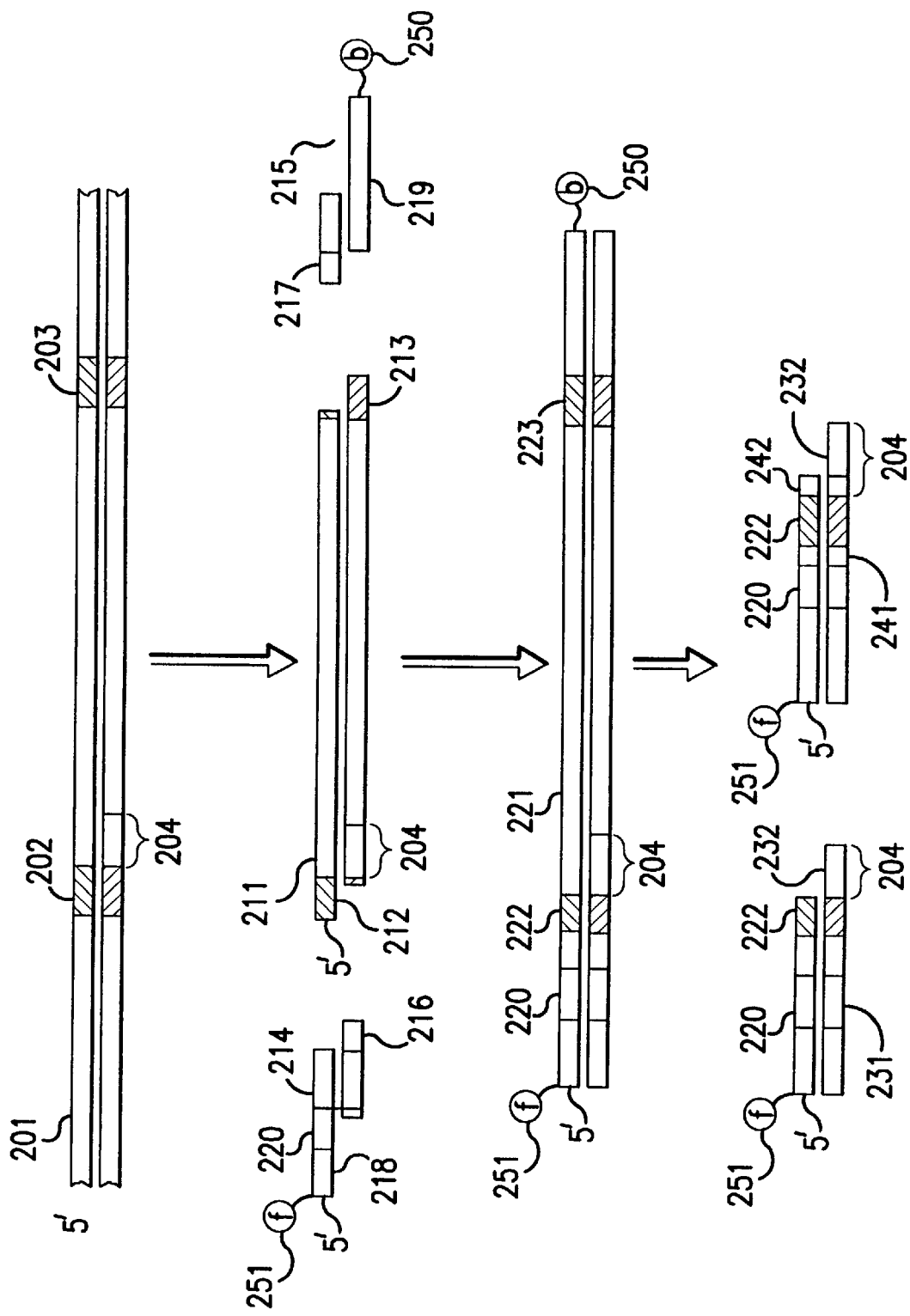
FIG. 2 illustrates preferred steps of a preferred observational method of this invention as applied to an exemplary nucleic acid.

Turning now to the preferred observational method, FIG. 2 illustrates methods for the first step, which are described in this subsection as applied to an exemplary nucleic acid. Here, dsDNA 201, a nucleic acid in an original sample of double stranded nucleic acids, is input to the first step. Certain aspects of the structure of dsDNA 201 are to be determined by the observational methods, namely, in this step, selection of nucleic acids having primary subsequence 202 and 203 with particular and predetermined nucleotide sequences, and in the next step determination of additional subsequence 204 in the selected nucleic acids. As is preferred, additional subsequence 204 is illustrated adjacent to primary subsequence 202. Alternatively, additional subsequence can be spaced from primary subsequence 202 by a number of nucleotides which is fixed in a subsample (but can vary between subsamples). The first step produces a subsample of nucleic acid fragments, such as nucleic acid 221, derived from nucleic acid 201, and having a structure adapted for determination of additional subsequence 204.

This first step may employ any method by which nucleic acid 221, having determined primary subsequences and adapted to determination of the additional subsequence, can be derived from nucleic acid 201. For example, primary subsequence 202 and 203 can be recognized by DNA binding proteins of all types, by hybridization with oligo-deoxynucleotides or oligo-deoxynucleotide mimics, and so forth. In a preferred embodiment, this first step utilizes Type II REs to recognize primary subsequences 202 and 203, and generates various intermediates, including intermediate nucleic acid 211. In the following, this preferred embodiment, including certain variations, is described, followed by a summary of certain alternative embodiments. In FIG. 2, the RE recognition sites or subsequences thereof are identified by diagonal indicia.

The preferred embodiment proceeds by a series of conventional processing steps the details of whose protocols are well-known to one of ordinary skill in the art. See, e.g., PCT Publication No. WO 97/15690 (in particular Sections 5.2, 6.3, 6.4, 6.5, 6.10, 6.11); U.S. Pat. Nos. 5,093,245; 5,366,877; Ausubel et al., eds., 1997, *Current Protocols in Molecular Biology*, John Wiley & Sons, Inc., New York; Sambrook et al., *Molecular Cloning A Laboratory Manual*, Cold Spring Harbor Press, (2nd. ed., 1989); *New England Biolabs 96/97 Catalog,* New England Biolabs, Beverly, Mass. (1996), all of which are incorporated by reference herein in their entirety.

Preliminary to the steps illustrated in FIG. 2, an input sample of dsDNA nucleic acids is dephosphorylated by an alkaline phosphatase such as, e.g., Barents Sea shrimp alkaline phosphatase. Next, the dephosphorylated sample is divided into separate batches, one batch for each pair of selected nucleotide sequences from the set of selected nucleotide sequences, and each batch is separately processed into subsamples according to the following further steps that are illustrated in FIG. 2.

First, each batch is processed in a combined RE-digestion/adapter-ligation reaction. Reaction conditions include sufficient amounts of the Type II REs, recognizing the pair of selected nucleotide sequences, and appropriate buffers such that sample nucleic acids 201 are substantially completely digested into fragments 211. Digested fragment 211 has single-stranded overhang 212, comprising a portion of the RE recognition site 202 remaining after digestion, and single-stranded overhang 213, similarly derived from recognition site 203.

Also present in the RE digestion/ligation reaction are molar excesses of adapters 214 and 215, which are hybridizable with single-stranded overhangs 212 and 213, respectively, resulting from RE digestion, and a ligase, such as T4 DNA ligase. The adapters comprise linker strands 216 and 217 having 5'-ends complementary to overhangs 212 and 213, respectively, and primer strands 218 and 219 hybridizable with the 3'-ends of linkers 216 and 217, respectively. The primers typically have of length of 18 to 30 nucleotides, most preferably a length of approximately 24 bases, and have a sequence which does not recreate an RE recognition site upon ligation, in order that their ligation terminates further RE digestion. In addition, primer strand 218 of the adapter hybridizable with the end of fragment 211, which is in a fixed relation to additional subsequence 204, is labeled with, e.g., radioactive, enzymatic, or preferably fluorescent means 251, such as the fluorophore FAM (Catalog # C-1311, Molecular Probes, Eugene, Oreg.). Primer strand 219 of the adapter hybridizable with the other end of fragment 211 (not in a fixed relation to the additional subsequence) is linked to binding moiety 250 such as, e.g., a hapten, preferably biotin. Preferably, linkers 216 and 217 have a length of 8 to 16 nucleotides, and most preferably 12 nucleotides, and have no terminal phosphates, in order to prevent self-ligation. Activity of the ligase on fragment 211 with hybridized adapters ligates primer strains 218 and 219 to the respective ends of fragment 211, and creates fragment 221. Alternately the RE digestion and ligation steps can be done sequentially. Detailed conditions for carrying out such digestion/ligation reactions, including necessary buffer conditions as well as precise prescriptions for designing the adapters, in order that substantially all input nucleic acids 201 are converted into fragments 221 are well known in the art (see, e.g., PCT Publication No. 97/15690) or available from manufacturer's specifications (*New England Biolabs 96/97 Catalog*, New England Biolabs, Beverly, Mass. (1996)).

In a preferred second processing step, the results of the RE digestion/ligation reactions are processed by PCR amplification in a standard manner (or by other amplification means), thereby creating an amplified subsample with nucleic acid fragments having the structure of fragment 221. Sufficient cycles of PCR amplification are performed so that final fragments 231 and 241 have sufficient concentrations to be detected by whatever detection means are utilized. Alternatively, where subsequent detection means are sufficiently sensitive, this amplification step can be omitted.

In detail, fragment 221 includes subsequences 222 and 223, which are the remaining portions of the RE recognition sites 202 and 203, respectively, and additional subsequence 204 adjacent to subsequence 222. Terminal to subsequences 222 and 223, are subsequences having the sequence of primer strands 218 and 219, respectively. Therefore, either primer sequences 218 and 219, or a similarly labeled, hybridizable portion of sequences 218 and 219, can be used as PCR primers. Prior to PCR amplification, the ligated products are blunt-ended by contacting them with a DNA polymerase and dNTPs in appropriate polymerization conditions.

PCR amplification protocols used in this invention are preferably optimized for specificity and reproducibility according to methods known in the art. See, e.g., Innis et al. eds., *PCR Protocols A Guide to Methods and Applications*, Academic Press, San Diego, Calif. (1990). For example, to achieve increased amplification specificity, amplification primers are preferably designed by to have a high Tm, preferably above 55° C. and more preferably above approximately 68° C. Primers are further designed not to hybridize with any native fragment species in the subsamples to be analyzed. Primer mis-hybridizations, and consequent spurious amplification products, are minimized by performing all amplification steps at a temperature near, at, or above the Tm of the primer. In particular, high annealing temperatures (no more that 1–5° C. less than the primer Tm) minimize primer mis-hybridizations. (In the following, the temperature Tm, or the "melting temperature," is the temperature at which half of a species of double-stranded nucleic acid molecules are denatured into single-stranded nucleic acid molecules.) Finally, longer extension and melting times reduce PCR bias related to smaller fragments and high G+C content.

PCR amplification amplifies only those fragments that have been doubly digested by the REs. Only such fragments have sequences complementary to primers on both ends, and only such fragments will therefore exponentially amplify. Alternately, one primer (not having the Type IIS site) can have a conjugated biotin to aid in removal of correctly digested reaction products from the other reaction products.

The adapters 214 and 215 have additional structure, in particular Type IIS RE recognition subsequence 220 which is adapted to the determination of additional subsequence A1. Also, the adapter without the Type IIS site preferably has a conjugated capture moiety, such as biotin, so that fragments cut by a Type IIS RE can be cleanly separated. This structure is described in the next section.

According to an alternative embodiment, the length of the primary subsequences 202 and 203 can be one, two, or more nucleotides longer than RE recognition sites (with a corresponding displacement of additional subsequence 204) by the use of phasing primers in the optional PCR amplification step. Phasing PCR primers for a fragment with a known terminal subsequence and an unknown central subsequence are herein taken to mean primers hybridizable with both the known terminal subsequence and with one, two, or more nucleotides (referred to herein as "phasing nucleotides") of the unknown central subsequence adjacent to the known terminal subsequence. Such primers are well known in the art. See, e.g., European Patent Application 534,858 A1. By the separate use of four phasing primers with a specified additional, overlapping nucleotide, pre-determined primary subsequences of length seven (where the RE recognition site was of length six) can be recognized in four sub-subsamples. Primary subsequences of length eight, nine, and more can be similarly recognized in 16, 64, or more sub-samples.

This invention is adaptable to other methods of generating subsamples having the structure of fragment 221. Several such methods are known to those of ordinary skill. According to one such exemplary method (Prashar et al., Proc. Nat. Acad. Sci. USA 93:659–663), cDNA is synthesized using a first-strand phasing primer with an oligo(dT) core, a number, e.g., two, of phasing nucleotides at the 3'-end, and a special "heel" subsequence at the 5'-end. After digestion of the cDNA with a Type II RE, a partially double stranded Y-adapter is hybridized and ligated onto the single-stranded overhangs of digested fragments. This Y-adaptor has a non-complementary region including a 5'-primer sequence. Finally, a pool of final fragments is produced by a PCR amplification of the ligated-digested fragments using a first primer, having the heel primer sequence, and a second primer, having the 5'-primer sequence. This method produces subsamples of fragments derived from nucleic acids having two known subsequences, one of which is the recognition site of the Type II RE and the other of which is a subsequence of one or more nucleotides adjacent to the poly(A) tail of mRNAs. The Y-adaptor or the "heel" can be adapted to contain a Type IIS recognition site in order to recognize an additional subsequence.

According to another exemplary method (U.S. Pat. No. 5,459,937), cDNAs are synthesized from natural sources using a first-strand phasing primer with an oligo(dT) core, a number of phasing nucleotides, and a recognition site for a rare-cutting Type II RE. The resulting cDNAs are then digested by the rare-cutting RE and another more frequently-cutting Type II RE. Doubly-digested fragments are ligated in an anti-sense orientation into a cloning vector, which is then used to synthesize cRNA. Further, cDNA is synthesized from this cRNA using first-strand primers having sequences corresponding to the portion of the cloning vector adjacent to the 3'-end of each insert and further phasing nucleotides. Finally, the resulting products are PCR amplified using primers comprising adjacent portions of the cloning vectors on both sides of the insert, one of these primers having additional phasing nucleotides. Thereby, by using multiple sets of phasing primers, this method generates final cDNA subsamples derived from mRNA having two known subsequences, one of which comprises a Type II RE recognition site extended by a certain number of nucleotides, and another of which is a subsequence adjacent to the poly(A) tail. Either final primer can be adapted to contain a Type IIS recognition site in order to recognize an additional subsequence. See, also, European Patent Application 534,858 A1.

According to further alternatives, the subsamples can be created by PCR amplification with primers recognizing the primary subsequences. Alternatively, the primary subsequences can be recognized by chemical cleavage, using such chemicals as neocarzinostatin (Gao et al., Biochemistry 34:40–49 (1995)), C1027 (Xu et al., Biochemistry 33:5947–5954 (1994)), or calicheamicin (Dedon et al., Biochemistry 32:3617–3622 (1993)).

5.1.2 Determination of Additional Subsequence

The second step of the two step observational method determines additional subsequence A1. This subsequence may be determined according to any procedure. For example, a less preferred procedure uses a plurality of phasing primers in a plurality of PCR reactions. Production of PCR product in any PCR reaction then signifies presence of the additional phasing nucleotides recognized by that phasing PCR primer. The additional subsequence is constructed from the phasing nucleotides so recognized. The multiple PCR amplifications necessary here can be advantageously performed by a laboratory robot. This less preferred alternative is adaptable to an additional subsequence of any length.

However, as previously described, it is preferable to use a procedure which recognizes all the additional subsequences in a subsample in a simultaneous, parallel, and quantitative manner. One preferred method uses a universal detection array ("UDA") in conjunction with a Type IIS RE, which is used to generate a "handle," or single-stranded overhang, for hybridization to the oligomers of a UDA. According to this preferred method, then, the additional subsequence includes the nucleotide sequence of the overhang produced by digestion of a nucleic acid having the structure of fragment 221 of FIG. 2 with a Type IIS RE.

Prior to description of this preferred method, the capabilities of a preferred implementation of a UDA are briefly reviewed. This implementation is described in detail in Section 5.2. A UDA is a simple high throughput device for accurately recognizing short terminal subsequences. Using hybridization/ligation (Section 5.2.3) a UDA recognizes single-stranded terminal subsequences. Using strand-invasion hybridization (Section 5.2.4), a UDA can also recognize short double-stranded subsequences adjacent to single-stranded terminal subsequences. Since a UDA contains all oligomers of a given length, it is therefore capable of recognizing in parallel all subsequences of that length with a single hybridization. No cumbersome cloning, sequencing reactions, and electrophoretic separation are necessary. By hybridization with a plurality of distinguishably labeled subsamples, a single UDA can simultaneously recognize subsequences in this plurality of subsamples. By adjustment of subsample nucleic acid concentration and UDA oligomer density, a UDA is capable of returning information on the quantitative amount of recognized subsequence present in a sample. Finally, various optional but preferred oligomer placement structures (error checking regions) and methods (stacking oligomers) result in highly-specific signals.

According to the preferred method, the Type IIS enzyme generates the single-stranded terminus, or "handle," necessary for a UDA. In more detail, a Type IIS RE cuts the dsDNA strands at a location displaced from the recognition site generating a single-stranded terminus, or overhang. It is preferable to use Type IIS REs of high specificity which generate a single-stranded terminus of at least 4 bps displaced at least 5 bp from the recognition site. The at least 5 bp displacement is preferable in order to cut beyond the portion of the 6 bp Type II RE recognition site remaining on the nucleic acid fragments. Type IIS REs adaptable to this invention include: BbvI, which generates a 4 bp overhang displaced 8 bp from the recognition site; FokI, which generates a 4 bp overhang displaced 9 bp; HgaI, which generates a 5 bp overhang displaced 5 bp; and CjeI, which generates two 6 bp overhangs displaced 8 or 9 bp in both directions from the recognition site.

In more detail, with reference to FIG. 2, type IIS recognition subsequence 220 is present on fluorescently labeled adapter 218. For each particular Type IIS RE, subsequence 220 is positioned in view of the length of the Type II RE recognition site 202 (typically 6 bp), the position of the Type II cut within subsequence 202 (for Type II REs generating 4 bp overhangs, the remaining portion, subsequence 223, of the recognition site remaining on fragment 221 is 5 bp in length), and the displacement between the Type IIS recognition site and cutting sites. Details of determining the exact placement of Type IIS recognition site 220 on adapter 218 are known in the prior art (see, e.g., PCT Publication No. 97/15690).

As illustrated by fragment 231, in case recognition site 220 is positioned so that Type IIS overhang 232 is adjacent to subsequence 222, the remaining portion of the Type II recognition site, then additional subsequence 204 is the sequence of this overhang. A UDA used according to hybridization/ligation can recognize additional subsequence 204 as the sequence of overhang 232. Alternatively, a UDA used according to strand-invasion hybridization can recognize both additional subsequence 204 as the sequence of overhang 232 as well as confirming one or more nucleotides of the known subsequence 222. Alternatively, as illustrated by fragment 241, in case recognition site 220 is positioned so that Type IIS overhang 232 is spaced apart from subsequence 222 by short double-stranded subsequence 242, then additional subsequence 204 is the sequence of single-stranded overhang 232 joined to that of double-stranded subsequence 242. A UDA is then used according to strand-invasion hybridization in order to recognize this entire additional subsequence 204. Also, optionally, one or more nucleotides of the known subsequence 222 can be confirmed. Less preferably, the UDA is used according to hybridization/ligation and double-stranded sequence 242 is ignored. Here in this less preferred case, there is a fixed gap between primary subsequence 202 and additional subsequence 204.

It is much less preferred to place the Type IIS recognition site so that the Type IIS RE cuts within the Type II recognition site. In this case the Type IIS overhang merely recreates part or all of the original Type II overhang. Thereby, the additional subsequence is shorter and the resulting subsequence set has less resolution.

For example, Type IIS RE FokI generates a 4 bp overhang displaced 9 bp from the recognition site. If its recognition subsequence 220 is placed 4 bp from the end of strand 218, then, since sequence 222 is 5 bp for a Type II RE generating a 4 bp overhang within a 6 bp recognition site, a fragment of type 231 is generated with FokI overhang subsequence 232 adjacent to subsequence 222. In this case additional subsequence 204 is 4 bp. Alternatively, if subsequence 220 is placed 3, 2, or 1 bp from the end of strand 218, a fragment of type 241 is generated with double-stranded subsequence of length 1, 2, or 3 bps, respectively. In this case additional subsequence 204 is 5, 6, or 7 bps, respectively. Thereby, FokI is capable of generating "handles" for additional subsequences of length 4–7 bps, which are recognized by a UDA used according to strand-invasion ligation.

In view of the previous, the second step receives a subsample of fragments generated with selected adapters 214 and 215 and then digests them with a selected Type IIS RE. Reaction conditions are chosen as is known in the prior art or according to manufacturer's recommendations in order to achieve complete digestion. See, e.g., PCT Publication No. 97/15690, or *New England Biolabs* 96/97 *Catalog*, New England Biolabs, Beverly, Mass. (1996). After digestion, the reaction products are contacted to an immobilized capture moiety, such as, e.g., streptavidin coated beads, that can bind binding moiety label 250, such as, e.g., biotin, and the contacted beads are washed. Thereby, the short digested fragments 231 or 241 are separated into the supernatant and the longer fragments not of interest are retained bound to the beads. These length of fragments 231 or 241, that is the length of subsequence 222 plus the length of primer 218, is typically from 17 to 35 nucleotides, and preferably approximately 29 nucleotides. Fragments 231 or 241 are labeled with, e.g., fluorescent moiety 251 and are ready for additional subsequence determination with, e.g., a UDA.

Alternatively, the nucleotide sequence of additional sequence 204 can be determined by any procedure known in the art. A less preferred alternative method for identifying this sequence from fragments 231 or 241 is to use such sequencing methods as Sanger sequencing reactions followed by denaturing gel electrophoresis. These alternative methods may also include a cloning step. Other methods involve determining the additional subsequence as the sequence of a single-stranded overhang generated by careful digestion with a exonuclease that preferentially digests a single strand of a double-stranded nucleic acid. T4 DNA polymerase has such exonuclease activity in the absence of dNTPs.

Embodiments Utilizing Mass Spectroscopy

A more preferred alternative method of determining additional nucleotide sequence 204, as well as alternative embodiments of the previous steps of this method, depend on mass spectroscopy ("MS"). MS alone can determine the sequence of fragments such as 231 or 241, without the need for hybridization or other means.

As is known to one of ordinary skill in the art, identification of nucleotide sequences of nucleic acid fragments by MS depends on mass determination of the nucleic acid fragments with sufficient accuracy so that each base can be recognized by its unique mass. See, e.g., Fitzgerald et al., Rapid Commun. Mass Spectrom. 7: 895–897 (1993). A mass accuracy achieved has been reported to be typically better than 0.1%. See, e.g., Bentley et al., Anal. Chem. 68:2141–2146 (1996). Recently, MS methods of improved resolution and sensitivity and applicable to complex mixtures of oligonucleotides have been developed. These are based on a variation of the matrix-assisted laser desorption/ionization time of flight method ("MALDI-TOF") using delayed ion extraction ("DE-MALDI"). See, e.g., Roskey et al., Proc. Natl. Acad. Sci. USA 93:4724–4729 (1996), which reports that by coupling a high yield cycle sequencing protocol to DE-MALDI, sequencing of dideoxy-terminated DNA mixtures of templates up to 40 or 50 bases long was achieved.

Accordingly, in one alternative implementation, the sequence of fragments 231 or 241, and thus additional subsequence 204, are determined using appropriate MS methods. For example, since these fragments are typically less than 40 nucleotides, the DE-MALDI method reported by Roskey et al. may be directly applied.

An improvement to the previous alternative involves a further digestion of fragments 231 or 241 by a Type II RE. This improvement can dramatically improve resolution and specificity of subsequent MS sequence determination by removing unnecessary known sequence from the fragment to be sequenced. Subsequence 222 of these fragments typically consists of 5 bp out of the 6 bp palindromic recognition site of the Type II REs recognizing primary subsequences 202. Therefore, subsequence 222 typically contains a 4 bp palindromic sub-subsequence that can be cleaved by a Type II RE recognizing such a 4 bp subsequence. In fact, Type II REs are commercially available that recognize all 4 bp palindromic sequences other than the sequences ATAT, TATA, and TGCA. Cleavage of fragments 213 or 214 with such a Type II RE produces larger sub-fragments of known sequence, which are not of interest, as well as sub-shorter fragments containing additional subsequence 204, which are of interest. Since these shorter sub-fragments have at most 5 bp of known sequence linked to unknown additional sequence 204, MS determination of their sequence is much more sensitive. Therefore, instead of approximately 25 bp of known sequence, the shorter sub-fragments have only approximately 5 bp known sequence forming the background for the MS mass, and therefore sequence, determination.

In brief, this alternative proceeds by further digesting fragments 213 or 214 with Type II REs that cleave within sequence 222. The short fragments of interest are separated from the long fragments not of interest by, e.g., reverse phase HPLC. The separated short fragments can then be directly sequenced by any appropriate MS method, for example by DE-MALDI. Thereby, additional sequence 204 is determined.

An alternative embodiment of this invention utilizes mass spectrometry to determine the sequences of fragments produced by those unique REs that cut on both sides of their recognition site, directly producing short nucleic acid fragments from a nucleic acid in the original sample. Such REs include BcgI and CjeI which produce 34 bp fragments, and BaeI and CjePI, which produce 33 bp fragments. An input sample is digested by such an enzyme under conditions, according to manufacturer recommendation or as known in the art, for substantially complete digestion. The short cut fragments of appropriate length are isolated by any separations method, preferably, HPLC or denaturing gel electrophoresis. These sequences of these short fragments can be directly determined by MS according to the DE-MALDI method. Finally, the sequences for 33–34 bp fragments of nucleic acids in the sample can be directly used by known sequence database search tools to identify nucleic acids present in the input sample that could be a source for such fragments. For example, sequences in a sequence database can be directly searched for the identified substrings, or alternatively, homology search tools, such as, e.g., BLASTN, can be used. As is known in the art, a fragment of such a length will in most cases uniquely identify a source nucleic acid in the database.

5.1.3 Database Search

This subsection describes the third step of the gene-calling methods of the instant invention. The previous two method steps, that is the step of generating a subsample of fragments from those nucleic acids of the original sample having two specified primary subsequences and the step of determining an additional subsequence in the nucleic acid fragments of the subsample, have observed that certain subsequence sets, which are defined by the primary subsequences and the additional subsequence, are present in nucleic acids of the original sample. This third step searches a database of nucleic acid sequences which are likely to be present in the original sample for sequences having the observed subsequence sets. In the following, this section generally describes, first, nucleic acids databases useable in this invention, next, relevant data processing techniques which this step utilizes, then, methods for producing a database of sequences likely to be present in the sample, and last, methods for searching such a database to find sequences having particular sequence sets.

Numerous nucleic acid sequence databases are known in the art. Such databases include the "official" databases, whose goal is to make substantially all known nucleic acid sequences publicly available from only a few sources. The official databases include GenBank (National Center for Biotechnology Information, Bethesda, Md.) Benson et al., Nuc. Acids Res. 25(1): 1–6 (1997)), the EMBL Nucleotide Sequence Database, (European Bioinformatics Institute, Hinxton, United Kingdom) (Stoesser et al., Nuc. Acids Res. 25(1):7–13 (1997)), and the DNA Databank of Japan (National Institute of Genetics, Shizuoka, Japan) (Tateno et al., Nuc. Acids Res. 25(1):14–17 (1997)). Such databases attempt to collect at least all published nucleic acid sequences into a standardized representation. They typically make this collection available in periodic releases (entire copies as of a certain date) available on CD-ROM or other media, and are accessible over the Internet for download or search.

Other databases are also known to those of skill in the art and are publicly available. Such database includes those directed to particular organisms, those directed to mutations associated with particular genes or linked to particular diseases, and so forth. Databases directed to particular organisms include, for example, the MIPS database with the complete genome of *Saccharomyces cerevisiae* (Mewes et al., Nuc. Acids Res. 25(1):28–30 (1997)), the FlyBase database with sequences of *Drosophila melanogaster* (The FlyBase Consortium, Nuc. Acids Res. 25(1):63–66 (1997)), various databases with complete or partial microbial genomes (see, e.g., The Institute for Genomic Research, Rockville, Md., and at http://www.tigr.org), and so forth, Databases directed to particular mutations and diseases include, for example, those with Factor VIII mutations (Kemball-Cook et al., Nuc. Acids Res. 25(1):128–132 (1997)), with p53 and APC mutations (Beroud et al., Nuc. Acids Res. 25(1):128 (1997)), with Marfan disease related mutations in the FBN1 gene (Collod-Beroud et al., Nuc. Acids Res. 25(1):147–150 (1997)), and so forth. A comprehensive review of nucleic acid sequence databases can be found in the Jan. 1, 1997, issue of Nucleic Acid Research (vol. 25, no. 1) and preceding annual database issues.

The methods of this subsection are adapted to the general structure adopted by the "official" sequence databases. See, e.g., *EMBL Nucleotide Sequence Database User Manual*, European Bioinformatics Institutes, Hinxton, United Kingdom (Release 51, 1997); *NCBI-GenBank Flat File Release 102.0 Distribution CD-ROM Release Notes*, National Center for Biotechnology Information, Bethesda, Md. (1997). This general structure includes separation of the database into "divisions," each division containing a large number of "sequence entries." Each division generally groups sequence entries of similar taxonomic derivation. For example, GenBank has divisions containing sequence entries from primates, rodents, other mammals, other vertebrates, invertebrates, plants, bacteria, viruses, phages, along with several EST ("expressed sequence tags") divisions. (The EST divisions are separated because of the particular characteristics of EST sequences).

In a preferred (flat file) embodiment, each division is represented as a plurality of sequence entries, each entry being a plurality of structured data lines of text in ASCII characters. Each GenBank division is distributed as a separate flat file, which in this representation is therefore a flat text file. Each data line has data of a particular type, which is identified by keywords or key symbols placed at fixed positions in each data line. Most data types include parameters identifying a sequence entry, including, for example, the accession number of the entry, origin species of the entry, taxonomy of the origin species, biological type of this sequence, biological features of the sequence, literature references relating to this sequence, and so forth. One data type is reserved for the nucleotide sequence data lines. A special key symbol (for GenBank, "//") marks special lines dividing separate sequence entries. The biological type parameter distinguishes the biological function of the sequence, such as DNA (genomic sequences), mRNA (expressed sequences), structural RNAs, etc. The sequence features parameter typically can include the coding domain sequence ("CDS") (as a character string or as an indication of the position of the CDS in the sequence data), positions of introns, position of exons, positions of any STS markers, and so forth. Sequence databases can optionally include indexes permitting retrieval of entries based on entry content.

In view of the above, in a preferred embodiment, the methods of the database searching step can be implemented using computer techniques relating to text or string processing and parsing. For example, since GenBank flat files consist of entries with structured data lines identified by tokens (that is, keywords) of text and in particular, in which the sequence data appears in the form of character strings of the letters A, C, G, and T (representing nucleotides), the methods of this invention require recognizing tokens in sequence entry data lines, in order to identify sequence entries of interest, and recognizing patterns of subsequences in sequence data strings, in order to recognize sequence sets in sequence data strings. Both these tasks are cases of the general problem of recognizing regular expressions in strings. Regular expressions are well known in the computer arts. A definition can be found in, e.g., Sedgewick, *Algorithms in C*, Addison-Wesley Publishing Co., Reading, Mass. (1990), which is incorporated herein by reference in its entirety, especially chapter 20. Given a specification of a regular expression, it is also well known in the computer arts how to routinely and simply create a program for recognizing such an expression in strings. See, e.g., Id.; Aho et al., *Compilers Principles, Techniques, and Tools*, Addison-Wesley Publishing Co., Reading, Mass. (1986), which is incorporated herein by reference in its entirety, especially chapter 3.

These string processing techniques have been implemented in numerous, publicly available, regular expression recognition and parsing tools are already, as is known to one of ordinary skill. These tools can be adapted to alternative embodiments of this invention. Such tools include, for example, system utilities such as the UNIX utility "grep," which can recognize an input regular expression in an input string. Many word or text processing programs accept regular expressions for searching retrieved text. Special languages are available which include built-in regular expression recognition and parsing, such as the language Perl. See, e.g., Wall et al., *Programming Perl*, O'Reilly & Associates, Inc., Sebastopol, Calif. (1992). Perl includes a syntax for specifying regular expressions and a run-time engine for recognizing regular expressions in text strings. Finally, regular expression algorithms known in the art, such as those disclosed in Sedgewick or Aho et al., can be implemented in general purpose programming languages, e.g. C or C++.

In an alternative embodiment, sequence databases are stored in a database system according to particular data model, e.g., in a relational database system such as SYBASE from Sybase, Inc. (Emeryville, Calif.) or the systems available from the Oracle Corporation. According to this embodiment, sequence data strings for nucleotide sequences of, for example, selected origin species and selected type can be retrieved by SQL queries from the relational database, as is well known in the computer arts. See. e.g., Ullman, *Principles of Database Systems*, Computer Science Press, Rockville, Md. (1992); McGovern et al., A Guide to SYBASE and SQL Server, Addison-Wesley Publishing Co., Reading, Mass. (1993). These strings can then be subsequently parsed for regular expressions representing observed sequence sets. Alternatively, a sequence database in relational format may be converted into a series of text files, and processed according to the previously described preferred embodiment.

Now turning to the specific methods for database searching, in a preferred embodiment these methods include two general steps: a first step which produces a database of sequences likely to be present in an original sample, and a second step which searches this database of sequences likely to be present for those sequences with the particular sequence sets observed in the preceding two steps of this invention.

FIG. 9A generally illustrates a preferred embodiment of the database searching step. One input to this step is sequence database 901, which is represented here in an exemplary manner as a plurality of files, one file for each division. Another input to this step are quantitative observations 905 of sequence sets in the original sample, which are output from the preceding method steps applied to an original sample. The first processing step, selection step 902, selects from sequence database 901 those sequence entries for nucleic acids likely to be present in the original sample and stores these sequences in database 903. In one embodiment, selection step 902 sequentially (that is, in the order as stored in the database) scans all the sequence entries of the appropriate division or divisions of the sequence database and selects those entries having parameters most closely describing the types of sequences in the sample. Where indexes are present, these can advantageously be searched in order to find directly the particular sequence entries of interest, thereby avoiding sequential search of all sequence entries.

In more detail, each sequence entry is fetched, and the keywords describing the data lines are recognized. For data lines with keywords of importance, the parameters describing this entry are recognized, compared to values describing the original nucleic acid sample, and the entry is retained if the values match. For example, in the case of a sample of cDNA from a mouse, entries for the rodent division of can be sequentially searched for an origin species of "Mus musculus." Such mouse sequence entries that are further of type "mRNA" (which is also used for cDNA) or which contain a coding domain sequence (that is have a value for feature "CDS") are stored. Alternatively, the EST divisions may also be searched for mouse entries. For a further example, in the case of a sample from a virally infected mouse, the virus division can also be similarly searched for CDS or expressed entries from the infecting virus. Certain sequence entry parameters, such as literature reference parameters, are unlikely to be significant in defining selection criteria Next, sequence search step 904 searches sequence strings stored in sequence entries. in database 903 in order to find those sequence strings containing observed sequence sets 905. As previously discussed, a sequence set is observed only if a nucleic acid in the original sample has the observed first primary subsequence S1, the observed additional subsequence A1 a fixed number, N (determined by the observational method), of nucleotides 3' to S1, and the observed primary subsequence S2 any number of nucleotides 3' to A1. As is apparent to one of ordinary skill in the computer arts, a sequence set defines a regular expression which can be used to search strings representing nucleic acid sequences for occurrences of the sequence set. As an example, and without limitation, in the notation of Perl, a regular expression representing a sequence set is denoted by:

$$\$s1[A,C,T,G]\{N\}\$a1[A,C,T,G]*\$s2 \qquad (1)$$

(blanks present for clarity only) where $\$s1$ ($\$s2$) is a scalar variable having a value which is the nucleotide sequence of the first (second) primary subsequence, S1 (S2) and $\$a1$ is a scalar variable having a value which is the nucleotide sequence of the additional subsequence, A1. A nucleic acid produces an observation of this sequence set only if the string representing the nucleotide sequence of the nucleic acid matches regular expression (1). In other words, the sequence string must have subsequence $s1, followed by exactly N occurrences of any nucleotide, followed by subsequence $a1, followed by any number (or zero) of nucleotides, and lastly followed by subsequence $s2. For a concrete example, if S1 has the sequence GAATTC (i.e., the value of $s1), A1 has the sequence AACGGTT (i.e., the value of $a1), S2 has the sequence AAGCTT (i.e., the value of $s2), and A1 is adjacent to S1 then the regular expression defining the sequence set pattern is:

GAATTC AACGGTT[A,C,T,G]*AAGCTT.

(blanks present for clarity only).

In more detail, sequence search step 904 reads sequence entries from database 903, and retrieves sequence string data from the entries. Next, this step parses these lines according to each previous regular expression representing an observed sequence set from input sequence sets 905, and returns the identity of those sequence entries matching a regular expression representing an observed sequence sets. Details of these sequences, for example, the sequence accession number and gene name, can then be retrieved from sequence entry parameter data lines and displayed to the user on, e.g., terminal 906, or stored for future retrieval (see below). Where quantitative abundance information is observed along with sequence set identification, as is preferred, this information can also be output to the user. Construction of such a program in an appropriate computer language, for example, Perl, in view of this foregoing detailed description is routine for those of ordinary skill in the art.

Alternatively, the construction of database 903 of sequences likely to be present in the sample can be avoided. In such an implementation, first, the method call selection step 904 to retrieve each entry from the appropriate division (or divisions) of sequence database 901 and to select those sequence entries likely to be present in the sample according to the previously described criteria, second, passes each selected sequence entry directly to sequence search step, and third, call sequence search step 904 to parse as previously the selected sequence with regular expressions representing each observed sequence set. In this manner, intermediate storage of database 903 is thereby, avoided.

In another embodiment, sequence search step 904 is replaced by the further steps illustrated in FIG. 9B. This alternative implementation is directed to making more efficient those applications involving multiple, repetitive searches of a single (or slowly changing) database of sequences likely to be present in a sample. Such an exemplary application can involve repetitive analysis of similar samples from the same species. According to the prior implementation, the time for each search of database 903 is proportional to the product of the sum of sizes of all the regular expressions representing the observed sequence sets and the total complexity of database 903 (the sum of the lengths of sequences in this database). Generally, increased database search efficiency can be achieved by preliminary creation of an index of substrings for the nucleotide sequences in database 903. Using such an index, the time for a search of database 903 is proportional only to the size of the regular expressions representing the observed sequence sets, a typically considerable improvement. The overhead of index creation, which is preferably linear in the total complexity of database 903, is amortized over all the individual sequence set searches.

Various data structures for such substring indexes are well known in the art. See, e.g., Gonnet, Handbook of Algorithms and Data Structures, Addison-Wesley, London (1984); Califano et al., *Proceeding, First International Conference on Intelligent System in Molecular Biology,* A.A.A.I. Press, Menlo Park, Calif., 56–64 (1993); Manber et al., *Proceeding: First Annual ACM-SIAM Symposium on Discrete Algorithms,* ACM, New York, N.Y., 319–327 (1990); McCreight, J. Assoc. Comp. Mach. 23:262–272 (1976); and Kempf et al., Acta Informatica 24:461–474 (1987). A preferred data structure is the position tree. See, e.g., Aho et al., *The Design And Analysis of Computer Algorithms,* Addison-Wesley, Reading, Mass. (1974). It is well known in the art that position trees are capable of improving the performance of queries to nucleotide and other biological sequence databases. See, e.g., Gonnet et al., Science 256:1443–1445 (1992); Lefevre et al., Comp. Appl. Biosc. 9:343–348 (1993); Lefevre et al., Comp. Appl. Biosc. 9:349–354 (1993); and Bieganski et al., *Proceedings of the Twenty-Seventh Hawaii International Conference on System Sciences Vol 5, Biotechnology Computing,* I.E.E.E. Comp. Soc. Press 35–54 (1994).

In detail, a position tree for a string, such as a nucleotide sequence, is a tree with leaves uniquely corresponding to each nucleotide position of the string and edges labeled by nucleotides, such that the sequence of edge labels from the root to a leaf corresponding to a particular position is the subsequence identifying that position in the sequence. A subsequence identifying a particular position in the sequence is the shortest unique subsequence of the sequence that begins at that position. Algorithms for the construction of such a tree in a time linear in the length of the input sequence are known in the art and discussed in the previous references. A database of sequences can be considered for this purpose as the single sequence which is formed by concatenating all the database sequence, each database sequence being terminated in the concatenation by a unique inter-sequence character. A position tree can be used for pattern matching by following the path from the root whose edges are labeled by the nucleotides of the pattern. See, e.g., Aho et al., Section 9.5. A preferred implementation of a position tree, termed a hashed position tree, is directed to the requirements of searching large sequence databases and is designed to efficiently use secondary storage to for storing index information. See, e.g., Mewes et al., Genome Analysis: Pattern Search In Biological Macromolecules, in Galil et al. eds., Combinatorial Pattern Matching, Lecture Notes in Computer Science 937, Springer, Berlin (1995), for the structure and storage layout of hash position trees.

Accordingly, the additional steps of this alternative embodiment include, first, index construction step 920. In a preferred embodiment, this step constructs a hashed position tree index stored in database 921 for the sequences in database 922 of sequences likely to be present in the sample (or alternately of appropriate divisions of sequence database 901). Database 922 is database 903 reorganized (if necessary) to permit efficient indexing. Although index 921 is illustrated as resident entirely on disk, it is preferable for efficient access that as much as possible of the index reside in memory during processing, with the non-resident parts accessible in a single disk access. A hash position tree is so structured. Next, sequence search step 924 takes as input regular expressions representing the observed sequence sets 923, reorganized sequence database 922, and constructed index 921, and searches for all sequence strings matching one of the regular expressions. The results are output to the user on, e.g., terminal 925, as previously. One of ordinary skill in the art will be able to construct programs for index construction and index search in a general-purpose language such as C or C++ in view of the prior description.

Further alternative implementations of the database searching steps optimized for specific applications will be apparent to those of ordinary skill. In particular PCT Publication No. 97/15690 contains extensive discussion of the computer processing of observations, like sequence sets, generated from nucleic acids in a sample.

Thereby, upon the completion of this step of database searching, candidate sequences are identified and quantified for nucleic acids present in the original sample. The candidate sequences identified are those sequences having observed sequence sets, as determined by their matching one of the input regular expressions. The candidates are quantified with the quantitative values observed for the corresponding sequence sets.

Various optional subsequent steps are appropriate for particular applications of the instant invention. A generally preferable further step is to store the results of the located candidate sequences and associated sequence database information together with an annotation of the nature of the original samples themselves for later processing and analysis. This storage is preferably organized in a relational format in a relational database system, and less preferably organized in other storage formats (such as text files). Accordingly, sequence search step 904 also outputs results to database storage system 910. These results advantageously include both the presence and the amount of candidates in the nucleic acid sample. The database storage system also receives input 911 describing the samples, for example their origin and processing, from which the gene-expression results originated. These two pieces of information are coordinated and stored in permanent computer-readable storage 912. Although illustrated as magnetic disc storage, permanent storage can be any form of such storage, including forms of semiconductor storage or optically based storage. Further, where confirmation steps (described in Section 5.1.4) have been performed, the candidate sequence information can be annotated to indicate its confirmation status.

Additional processing of the stored results can be advantageous, and processing and analysis step 913 generally includes means for a user to request various such additional processing and comparing and to receive output from these requests. Such additional processing can include simply redisplay of previously stored data for later review. More importantly, the stored data can be combined for various comparative analyses. For example, where a differential gene-expression experiment results in gene-expression data from tissue samples in controlled and related biological states, this data can be compared for interesting gene-expression differences. The quantitative gene-expression information in one dataset from one tissue sample can be subtracted, or otherwise numerically compared, with that from another dataset from a second tissue sample in order to yield differential expression information. In this manner, e.g., gene-expression in diseased and normal states can be compared.

Advantageously, such comparison can also involve more complex combinations. For example, where the genomic effects of a particular treatment for a particular disease in an organism are sought, permanent storage 912 can contain datasets reflecting the results of gene-expression experiments of this invention performed on nucleic acid samples from diseased-untreated tissue samples, normal-untreated tissue samples, diseased-treated tissue samples, and normal-treated tissue samples. As before, comparisons of datasets from the diseased-untreated tissue samples with those from the normal-untreated tissue samples can reveal genetic effects of the disease alone. Comparisons of datasets from the normal-treated tissue samples with those from the normal-untreated tissue samples can reveal the genetic effects and side effects, perhaps toxic, of the treatment on a normal organism. Additionally, comparisons of datasets from the diseased-treated tissue samples with those from the normal-treated tissue samples can reveal the total effects of the treatment in the context of the disease. Even more specific genetic effects of treatment can be seen by comparing datasets from the diseased-treated tissue samples with a comparison of normal-treated and normal-untreated datasets. Such a multiple comparison can reveal those unique genetic effects of the treatment in the context of the disease that are different from the effects of the treatment on the normal organism. Further useful comparisons will be apparent to one of average skill in the art.

Accordingly, analysis step 913 is advantageously constructed to accept requests from the user to perform various manipulations and comparisons on the data, where two, three, four, or more datasets are combined and compared according to various operations. Preferable comparison operations include algebraic operations (for example, finding differential gene-expression), boolean operations (for example, finding the presence or absence of gene-expression), and thresholding operations (for example, finding differential gene-expression above a certain threshold) on corresponding data values (data values relating to the same candidate nucleic acid) of the datasets. Operations supported also allow advantageously combinations of comparisons from different candidate nucleic acids into one criteria. Construction of programs to scan databases and perform such combinations and operations on retrieved data items are routinely built with standard tools using the facilities of, e.g., SQL queries and general purpose programming languages. Construction of such programs is within average skill in the art.

Further, processing and analysis step 913 can advantageously perform user requests for various types of homology searches. Located candidate sequences can be searched to find sequences having homologies, either at the nucleotide sequence level or at the protein sequence level, with a particular user query sequence. For example, identified sequences can be searched for those that are either (fully or partially) homologous to a nucleotide sequence of user interest, or for those that have protein products with protein homologies, or domains or motifs of user interest. Such homology search programs can be built on known algorithms, e.g., BLAST and BLAZE (Altschul et al., 1990, J. Mol. Biol., 215:403–510). Publicly available search tools of this type are exemplified by BLASTN and BLASTP (National Center for Biotechnology Information, Bethesda, Md.).

In further embodiments, this invention includes computer systems for performing such manipulations and comparisons on data previously stored on computer-readable storage media. Such systems include processing means for user requests and user input/output means for receiving requests and displaying processing responses. Processing means include programs for carrying out processing and analysis step 913, and in particular for carrying out the previously described user requests. These means also can access permanent storage systems 910 and computer-readable media 912, on which are recorded the results of gene-expression experiments performed according to this invention. Input/ output means include, for example, user terminals or PCs presenting a range of input modalities, such as keyboards and pointing devices, and a range of output devices, such a graphics displays and printers. Input/output means and processing means can be collocated on one computer system, or alternately, can be located on separate client and server systems, respectively, connected by a network.

FIG. 11 illustrates exemplary hardware means preferred for executing the programs of this invention. In general, the powers and capacities of these means are adapted, as routinely known in the art, to the size of the databases stored and to the required search times and the types of user processing. For example, database storage and user request processing can be performed on a single or multi-processor Pentium (Intel Corp.) server computer system 1101 running Windows NT Server (Microsoft Corp, Redmond, Wash.). Alternately, system 1101 can be a single or multi-processor server computer system from Sun (Mountain View, Calif.) running a version of the UNIX operating systems. In both cases, sufficiently numerous and capable server system processors are provided to process the expected number of parallel sequence set queries and user processing requests. Sufficient server system main memory is provided so that key components of the operating system and application programs can be memory resident along with sufficient data buffers for adequate search performance. Storage system 1102, for example system hard disks, is preferably provided to store on-line at least all the sequence and experimental results databases previously described. Preferably server systems also are provided with removable storage systems 1103, which can be tape or CD-ROM drives. A communications connection to the Internet is also preferable. Updated sequence database information can be obtained by either means.

User input/output means can be variously provided wither by direct attachment of user display 1104 to server system 1101, or by attachment of user display 1109 to local user system 1106. In the latter case, local user system 1106 is connected to server system 1101 by an, e.g., LAN connection 1105. Additionally, local system 1106 can have local storage 1107, local printers 1108, and other peripherals. User terminals can run, e.g., the Windows NT Client or the Window 95 system.

5.1.4 Confirmation Steps

Upon completion of the previous steps of the methods of this invention, candidate sequences for nucleic acids present in the original sample are identified, to the expected resolution, and quantitated. This invention includes optional, additional confirmation steps, which permit unequivocal and independent identification of the candidate sequences of particular interest previously identified by database search. These confirmation methods can also additionally serve to verify that additional subsequences have been correctly identified by, e.g., a UDA device.

Candidate nucleic acid sequences, which the previous database search step identified as containing observed sequence sets, can be of sufficient interest to apply the confirmation steps for several reasons. For example, a certain observed sequence set may be of interest if the database search identifies no candidate nucleic acids. Such sequence sets may derive from novel genes, novel gene regions, alternative splices of known genes, or additional members of gene families. Another observed sequence set may be of interest if the database search identifies multiple candidate nucleic acids. Such may occur because the resolution associated with the choice of subsequence lengths, as previously described, may be insufficient to permit a unique nucleic acid identification. Here, it may be of interest to determine exactly which candidate is actually present.

Finally, even if database search uniquely identifies a candidate sequence for a certain sequence set, this sequence set may be of interest if it has a different or unexpected quantitative intensity. Such a differentially expressed sequence set can arise from a gene is dysregulated or altered in the source cell or tissue used for preparing the sample. For example, two input samples of nucleic acids can be derived from similar tissues in pairs of comparable states. Pairs of comparable states can be normal versus physiologically perturbed, normal versus diseased, untreated diseased versus treated diseased, and so forth. Next sequence sets derived from the two samples are observed and comparisons made between the quantitative intensities of sequence sets derived from the two input samples. Different intensities for a particular sequence set can indicate alterations in the expression of one or more genes, gene families, alternatively spliced forms, or other genetic or epigenetic change(s). Unequivocal identification of the source of such sequence sets is of interest even if database search uniquely identified a candidate gene.

Having selected certain observed sequence sets of interest for confirmation for any of the above (or other) reasons, there are, according to this invention, two preferred methods for independent identification and verification of candidate DNA fragments from the subsample pool. A first method, termed selective amplification, utilizes a phasing primer for selective PCR amplification of those nucleic acids fragments in the subsample pool having the subsequence set of interest. The amplified and isolated fragment(s) are sequenced to confirm the identity of the fragment. A second method, termed signal suppression, utilizes an unlabeled phasing primer in molar excess (for example, 100–200 fold excess) to the labeled primer, which was used for the PCR amplification in the first method step, to competitively reduce or substantially eliminate observations of the sequence set of interest.

Both confirmation methods use a phasing primer constructed to recognize and amplify only those nucleic acid fragments with a particular sequence set. In the previous PCR amplification used to generate subsamples with fragments of the structure of fragment 221 (FIG. 2), primer sequences 218 and 219, or a similarly labeled, hybridizable portion of sequences 218 and 219, were used as PCR primers. The instant phasing PCR primer extends the primer having only sequence 218 (or a hybridizable portion of this sequence) with one also including subsequence 220 and additional subsequence 204. Therefore, the phasing primer only hybridizes with and amplifies only fragments having a particular specified additional sequence. In other words, this phasing primer amplifies only fragments with the corresponding sequence set. The second primer, having only sequence 219 (or a hybridizable portion of this sequence), can be used as previously.

In more detail, FIG. 3 illustrates the structure of a phasing primer. Phasing primer 302 is composed of three subsequences, which are in 5' to 3' order subsequence 303, subsequence 316, and subsequence 301. Subsequence 303 is a hybridizable portion of the sequence 218 and is preferably 10–14 bases long. It includes part of all of Type IIS recognition subsequence 220. Subsequence 316 is complementary to the remaining portion of the Type II recognition sequence, subsequence 222. Finally, 3' terminal subsequence 301 is complementary to the particular candidate subsequence 204 for the particular sequence set. For selective amplification, the phasing primer may be labeled or unlabeled. For signal suppression, the phasing primer is unlabeled. Finally, the phasing primer may contain one or more modifications known in the art, but is, preferably, unmodified.

Both confirmation methods proceed by a confirmation PCR amplification of a diluted aliquot of the subsample using a primer set including a phasing primer directed to the particular sequence set of interest. An aliquot of the nucleic acid subsample, after the steps of RE cutting, adapter ligation and PCR amplification, is diluted at least 1:100, or preferably 1:1000, or 1:10,000, or more. PCR amplification is performed as previously for 6, 10, 14, or more cycles, respectively, using conditions optimized for specificity and reproducibility.

For the method of selective amplification, only fragments having the particular additional subsequences are amplified (which are in turn derived from nucleic acids with the particular sequence set). Amplified fragments in the reaction products can be then identified by separation and sequencing. The reaction products can be separated by any method known in the art, preferably by agarose or polyacrylamide gel electrophoresis, and visualized using appropriate staining procedures or primer labels. See, e.g., Sambrook et al., *Molecular Cloning: A Laboratory Manual*, Cold Spring Harbor Press, (2nd. ed., 1989). The apparent length of the PCR products can be estimated by comparison to molecular size standards. A plurality of PCR products with different sizes means that multiple nucleic acids in the sample contained the particular sequence set. Further, it is preferable to extract and purify each separated reaction product. Any extraction procedure known in the art can be used, such as, e.g., electrophoretic separation of bands and extraction and purification using a commercial gel extraction kit, such as QIAquick Gel Extraction Kit, Qiaqen (Hilden, Germany). The extracted product from each individual band can be re-amplified. Additionally, the sizes of the PCR fragments and clones should match the subsequence length for at least some of the hits identified by database searches. Alternately and less preferably, the products from the PCR reaction can be ligated into a suitable vector, transformed into a suitable *E. coli* host and cloned.

The separated products can be sequenced by any method known in the art. In particular Sanger sequencing reaction products can be separated on a commercial gel electrophoresis device to determine the sequence. For example, the sequencing kit ABI PRISM™ dRhodamine Terminator Cycle Sequencing Kit together with an ABI 377 (Applied Biosystems, Inc. Foster City, Calif.) device can be used. The fragment sequences obtained can be matched with sequences present in DNA sequence databases in order to identify the fragment by using, e.g., the BLASTN program.

Thereby, the methods of selective amplification identify the nucleic acids in the sample contributing to a particular sequence set observations of interest.

The confirmation method of signal suppression confirms that the particular sequence set of interest was correctly observed by, e.g., a UDA. If the sequence set was correctly observed, signal suppression results in suppression of the observed signal after a second, confirmatory PCR amplification and additional subsequence observation. For this method, a diluted aliquot of the nucleic acid fragment subsample is subjected to a confirmatory PCR amplification as previously described, except for the primers present. The original primers based on subsequences 218 and 219 (FIG. 2) are used as described in the previous subsection along with a molar excess (preferably 100 to 200 fold) of the unlabeled phasing primer. Since the excess phasing primer competitively amplifies fragments having the particular sequence set, these products are therefore unlabeled. All other fragments will be amplified and labeled as previously. Upon determination of the additional subsequence, for example, by a UDA, the signal from the particular sequence set is suppressed. However, if the additional sequence was incorrectly determined, the phasing primers will not suppress the signal of interest.

According to these confirmation methods both the correct observation of a sequence set of interest can be verified, and the identities of nucleic acids producing an observed sequence set of interest can be independently confirmed.

5.2 Universal Detection Arrays

A universal detection array (UDA) is a set of probe oligonucleotides designed to recognize terminal subsequences of target nucleic acids in a sample of nucleic acids. In one embodiment, a UDA is universal because it is capable of recognizing all terminal subsequences of a given length, N, in which case it includes $4^N$ species of probes, one for each possible terminal subsequence of length N. In another embodiment, a UDA is designed to recognize only certain nucleic acids of interest, in which case it includes fewer than $4^N$ species of probe oligomers. Generally, in both embodiments, target recognition depends on probe hybridization to the terminal subsequences recognized.

In a preferred application to the gene-calling methods of Section 5.1, a UDA is used to recognize short terminal subsequences of a nucleic acid. The length of recognized terminal subsequences is preferably between 4 and 12 nucleotides, and more preferably between 6 and 8 nucleotides. Preferably, methods of using a UDA includes features to stabilize hybridization to such short terminal subsequences, including enzymatic recognition of hybridization and base stacking energetic assists. According to the preferred embodiment of this invention, a UDA is used preferably, according to the methods of hybridization/ ligation ("h/l" method) or strand invasion ligation ("SIL" method), both of which incorporate such features. Target nucleic acids are preferably fluorescently labeled and detection of recognition is by fluorescent imaging. The location of a fluorescent signal on the array indicates the terminal subsequence recognized.

The following subsections describe details of construction and use of a UDA. First, the construction of a UDA is described in separate subsections detailing the design of probe oligomers and the physical layout and preparation of a UDA. Second, the use of a UDA is described in separate subsections detailing the method of hybridization/ligation, the method of strand invasion ligation, and the methods of detection.

5.2.1 Probe Design

Figure 4A:
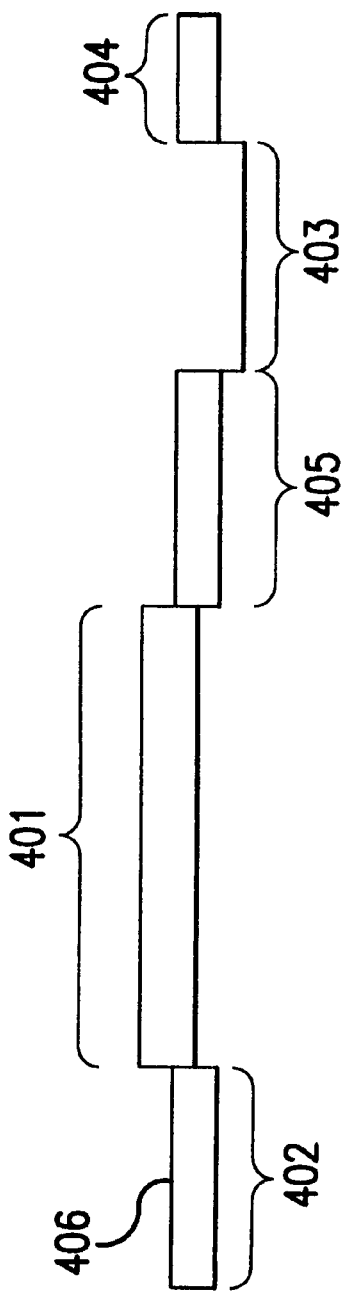
FIG. 4 illustrates a preferred structure for a probe of a universal detection array of this invention.
Figure 4B:
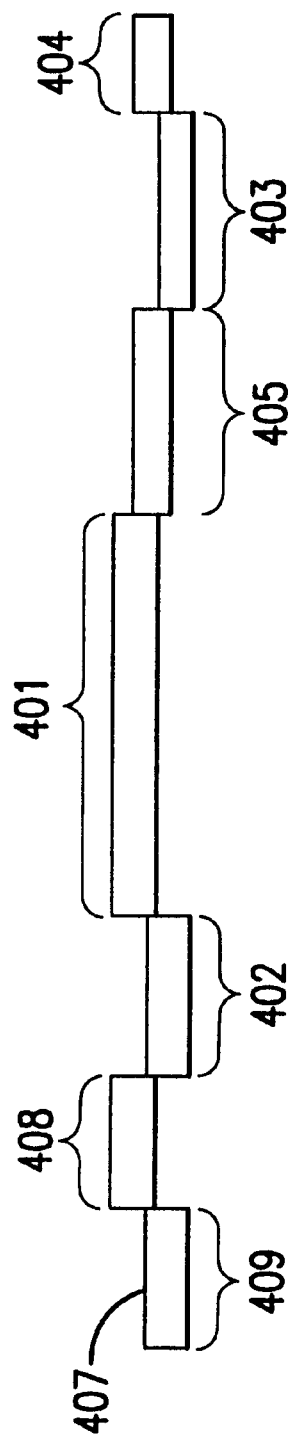

According to this invention, a probe oligomer is a substantially linear structure having several regions of defined internal function and structure, one of which functions to hybridize with and recognize short terminal subsequences of a target nucleic acid. In a preferred but non-limiting embodiment, probe oligomer 406 is illustrated in FIG. 4A to be comprised of 5 regions: hybridization region 402, core region 401, spacer region 405, linker region 403, and functional group 404. One or more of these regions can be nucleotide polymers and the remainder of the regions can be polymers of other than nucleotide monomers, or of alternative structure. In this subsection, these regions are described in the listed order, followed by description of certain probe alternatives.

Hybridization region 402 is a terminal region of a probe molecule that participates directly in recognition of a terminal subsequence of a target nucleic acid according. Preferably, this is an oligonucleotide sequence that recognized by hybridization, according to either the h/l or the SIL methods. The direct h/l methods, described in Section 5.2.3, recognize only single-stranded terminal subsequences, In this case, region 402 is, preferably, of the same length as such a single-stranded terminal region in the target nucleic acids. The SIL methods, described in Section 5.2.4, recognize a terminal subsequence including a short double-stranded subsequence adjacent to the terminating single-stranded region. In this case, region 402 is the sum of the number of nucleotides in the single-stranded overhang and the number in the adjacent double-stranded subsequence. Alternatively, this region can include one or more nucleotide mimics, such as, e.g., peptido-nucleic acids.

The sequence of the oligonucleotide hybridization regions of probes in a UDA varies according to the application of the UDA. Since a probe recognizes a terminal subsequence of a target by hybridization of the probe to the target terminal subsequence, where the UDA is designed to recognize all possible terminal subsequences of length N, the UDA should include probes with hybridization regions of all possible sequences of length N (i.e., a universal set), that is $4^N$ probe species are necessary. The length N is the length of a terminal single-stranded subsequence, and for the SIL method, the adjacent double-stranded region. For example, if the length N is 4 bases the maximum number of probe species in the UDA is $4^4$ or 256; if N is 54 bases the UDA size is $5^4$ or 1024; if N is 6 bases, the UDA size is $6^4$ or 4096; if 7 bases, it is 16,384; if 8 bases, it is 65,536; and so on. Preferably, the length of the hybridization region is between 4 and 8 nucleotides.

In other applications, the UDA can be designed to use a partially known terminal subsequence of target nucleic acids to increase hybridization specificity. In this case, target nucleic acids have known nucleotides at certain positions in their terminal subsequences, which are complementary to the known nucleotides at the corresponding positions in the terminal subsequence. In particular, in the case of the SIL method, all or the distal part of the double stranded region may be known and shared in all target nucleic acids. Then, the hybridization regions include a terminal fixed subsequence adjacent to a variable subsequence.

Finally, in further applications, a UDA may be designed to recognize only certain nucleic acids of interest in a sample. When used according to the gene-calling methods of Section 5.1, such a UDA recognizes only the certain additional subsequences (A1) of the sequence sets characterizing the nucleic acids of interest. In this case, the UDA need include only probe species having oligomer hybridization regions complementary to these certain additional subsequences. Such an application can be directed, for example, to analysis of patient samples for medical diagnostic purposes, for monitoring therapy, and so forth.

Core region 401 of the probe molecule, adjacent to hybridization region 402, is preferably an oligonucleotide (but can also include nucleotide mimics). The length and sequence of the core region is subject to several requirements. One such requirement derives from keeping hybridization region 402 sufficiently removed from any support to minimize stearic hindrance during target nucleic acid hybridization with the hybridization region. Further, when stacking oligonucleotides are used (see below), core region 401 itself must be kept sufficiently removed from any support to minimize stearic hindrance during stacking oligonucleotide hybridization with core region 401. This sufficient distance is known to be at least 40–60 atoms, or equivalently at least 6–10 nucleotides in length, for hybridization alone (Schepinov et al., 1997, Nuc. Acids Res. 25:1155–1161), and to be at least 50 Å for hybridization together with enzymatic ligation of hybridized nucleic acids (Broude et al., 1994, Proc. Natl. Acad. Sci. U S A 91:3072–3076). Therefore, the length in nucleotides of core region 401, along with the lengths of both spacer region 405 and linker region 403, are so chosen that this sufficient distance is met to obviate hybridization hindrances due to stearic effects of the support to which the probe oligomer is anchored. Another requirement on the length of core region 401 is that it be sufficiently long so that stacking oligomers can be designed with sufficiently strong hybridization characteristics (see below).

Other requirements to which core region 401 are subject derive from criteria for adequate hybridization with a stacking oligomer, which is at least partially complementary to the core region. The stacking oligomer (or oligonucleotide) preferably hybridizes adjacent to the hybridization region in order that there be base stacking interactions with a hybridized target nucleic acid. Preferably, the stacking oligomer hybridizes with the entire core region. In any case, the duplex of a core region and a stacking oligomer should have a sufficient Tm in view of the washing steps in the h/l and SIL methods (see below), which are designed to remove from an array mis-hybridized and non-specifically bound nucleic acids. (Mis-hybridization occurs if the oligomers undergo non-complementary hybridization or if the hybridized oligomers are not correctly aligned.) (Non-specific binding occurs if oligomers adhere to components of a UDA by interactions other than complementary base-pairing interactions, such as e.g., mere electrostatic attraction.) Therefore, $T_m$s should be at least approximately 40–45° C., preferably 50–55° C., and more preferably 60–65° C. for maximal discrimination between ligated and un-ligated species of stacking oligomer. Accordingly, core region 401 is preferably between 12 and 36 nucleotides, and is more preferably at least 16 nucleotides long with an at least 45% G+C content. (Accordingly, the core plus hybridization regions are preferably at least 20 nucleotides long.) Advantageously, the core region sequence is also limited to be free of secondary structure, dimers, hairpins, and so forth. It is preferable, but optional, that all the core regions in a UDA have the same sequence. Core region sequences can be designed in detail in view of these length and sequence requirements by method known in the art, for example, by software packages are available for oligomer construction, such as OLIGO™ from National Biosciences, Inc. (Plymouth, Minn.). The following exemplary core region sequence satisfies the previous requirements.

5'-ACC GAC GTC GAC TAT GGA-3' (SEQ ID NO:55)

The spacer region, linker region, and functional group form the attachment means. These attachment means link the hybridization and core regions to a support while promoting hybridization by reducing stearic hindrance, excess charge, and so forth.

Spacer region 405, adjacent to core region 401, is also preferably an oligonucleotide advantageously used to obtain sufficient distance between hybridizing region 402 and/or core region 401 and the array supports in order to minimize stearic hindrance of hybridization and ligation. A sufficient distance, preferably 30–70 Å, and more preferably at least 50 Å, between the support and areas of hybridization on the probe oligomer can be achieved by the length of the spacer region 405, by length of the linker region 403, (see below) or by the sum of both lengths. It is preferred that most of the distance be achieved by the linker region, the spacer region being optional.

The preferred sequence of spacer region 405 is $(dN)_n$, where dN is any deoxyribonucleotide and "n" is length of the oligomer. Preferably, space region 405 has the sequence $(dT)_n$, where n=5 to 20. Alternatively, the spacer region can have any sequence preferably not containing palindromic regions, G+C rich regions, subsequences of significant complementarity to the core region 401, or regions of self-complementarity. Spacer region 405 can also be modified as described subsequently.

Alternatively, regions of probes specified herein to be oligonucleotide, and other oligonucleotides of this invention, can include oligonucleotide mimics, such as peptide-nucleic acids ("PNAs"). See, e.g., Weiler et al., 1997, Nucleic Acids Res. 25, 2792–2799. In a PNA the bases are linked via N-(2-aminomethyl)-glycine unit. As a result, PNA:DNA duplexes exhibit higher stability than the corresponding DNA:DNA hybrids (~1.5 degrees Celsius per base pair) due to lack of the inter-strand repulsion between DNA phosphate groups. This is advantageous to improve the hybridization specificity of shorter oligomers. Single-stranded oligomers can include or be exclusively PNAs. Suitable double-stranded oligomers may be constructed entirely from PNAs or from mixed PNA and DNA, or mixed PNA, DNA, and RNA oligomers.

Linker region 403, adjacent to spacer region 405, is designed in view of its charge, length, and hydrophobicity and solvation. Concerning charge, it is preferable the linker region be substantially neutral in order to increase hybridization of target nucleic acids and stacking oligomers to probes. The negatively charged phosphodiester backbones of hybridization region 402, core region 401, and optional spacer region 405, especially when concentrated in a limited area of a support, can repel the similarly negatively charged backbone of a target nucleic acid. See, e.g., Schepinov et al., 1997, Nuc. Acids Res. 25:1155–1161. Consequently to reduce such concentrated negative charge and electrostatic interaction of the linker with the remainder of the probe, it is preferably that the linker be substantially neutral. Further, to minimize total probe charge, it is preferred that linker region 403, partially or wholly replace 405, as advancements are made in the technology for synthesizing longer and stable linkers. Concerning length, the linker region should be of a length such that, combined with the length of the spacer region, stearic hindrance of target nucleic acid or stacking oligomer hybridization due to probe supports is minimized.

Accordingly, it is preferable that linker region 408 not be an oligonucleotide. It is most preferable that linker region 405 be a hydrophobic aliphatic chain, more preferably an aliphatic chain having a length of the form of $(CH_2)_6$ to $(CH_2)_{40}$, which have an extended length of approximately 50–100 Å, and most preferably an aliphatic chain of approximately the length $(CH_2)_{12}$ to $(CH_2)_{20}$. Alternatively, the linker can be substituted with neutral groups in order to increase its hydrophilic character. Such linkers can be synthesized from monomeric units including propanediol, di- or tri-ethylene glycol. Either aliphatic or substituted aliphatic chains can be covalently attached to the terminal nucleotide of spacer region 405 according to such chemistries as synthesis of the last dT residue in the space region with a modified phosphoramidite containing the appropriate linker and functional group as a modification.

In addition, the linker can include a segment that permits chemical cleavage of the probe from the UDA support. For example, incorporation of the reagent (2-cyano-ethoxy)-2-(2'-O-DMTr oxyethylsulfonyl) ethoxy-N,N-diisopropylaminophosphine during linker synthesis permits selective cleavage of the oligomer by treatment with ammonia. See, e.g., Schepinov et al., 1997, Nuc. Acids Res. 25:1155–1161. A cleavable linker section can aid in the isolation and identification of rare species of nucleic acids, even single copies of nucleic acids in the sample. Specifically, after target nucleic acid ligation according to the h/l method, isolation is achieved by cleavage of the linker followed by PCR amplification of the ligated target and Sanger sequencing of the PCR product. This method can be applied to those probes that have low signals difficult to detect by the preferred optical detection methods described below. Probes with cleavable linkers can be mixed with non-cleavable probes and bound together to the same regions of a UDA or a separate array can be constructed having exclusively probes with cleavable linkers.

The terminal component of a probe is function group 404, which is covalently attached to linker region 403, either at or near its terminus. Functional group 404 is chosen to readily bind to the derivitization provided on the surface of the array supports with sufficient energy to resist the washes used in the h/l and SIL methods of this invention. In particular, covalent attachment is preferable with alternative binding interactions, such as that of biotin with streptavidin/avidin less preferable. Functional group 404 can include such active moieties as amino, sulfhydryl, biotin, dinitrophenol, and so forth. In the case of amino, the surface can be derivitized with thiocyanate, isothiocyanate, or carboxylic acids. In the case of biotin, the surface can be derivitized with avidin or streptavidin. In the case of dinitrophenol, digoxigenin, or other hapten, the surface can be derivitized with an antibody to these moieties. In the case of glass surfaces, derivitized with phenylisothiocyanate groups, an amino functional groups is preferred. Alternately, in the case of a surface with bound streptavidin, a biotin functional group is preferred.

Exemplary probes are illustrated in the Examples set forth in Section 6. Such probes can be synthesized by well known methods for synthesis of polynucleotides, such as, e.g., phosphoramidite chemistry performed by a commercial synthesizer, exemplary synthesizers being obtainable from Applied BioSystems, Inc. (Foster City, Calif.). The linker and functional group can be added by a modifying the phosphoramidite used to link the last nucleotide to also contain the appropriate linker and functional group. See, e.g., Schepinov et al., 1997, Nuc. Acids Res. 25:1155–1161. Alternately, the probes of this invention can be supplied by commercial suppliers, such as, e.g., Biosynthesis, Inc. (Lewisville, Tex.).

In embodiments of this invention where DNA oligomers are specified for performing functions, including use in probes or for hybridization and chain elongation priming, alternative oligomers can be used that comprise those of the following nucleotide mimics which perform similar functions. Nucleotide mimics are subunits (other than classical nucleotides) which can be polymerized to form molecules capable of specific, Watson-Crick-like base pairing with DNA. The oligomers can be DNA or RNA or chimeric mixtures or derivatives or modified versions thereof. The oligomers can be modified at the base moiety, sugar moiety, or phosphate backbone. The oligomers may include other appending groups such as peptides, hybridization-triggered cleavage agents (see, e.g., Krol et al., 1988, *BioTechniques* 6:958–976), or intercalating agents (see, e.g., Zon, 1988, *Pharm. Res.* 5:539–549). The oligomers may be conjugated to another molecule, e.g., a peptide, hybridization triggered cross-linking agent, transport agent, hybridization-triggered cleavage agent, etc.

The oligomers may also comprise at least one nucleotide mimic that is a modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. The oligomers may comprise at least one modified sugar moiety selected from the group including but not limited to arabinose, 2-fluoroarabinose, xylulose, nucleic acids ("PNAs"). See, e.g., Weiler et al., 1997, Nucleic Acids Res. 25, 2792–2799. In a PNA the bases are linked via N-(2-aminomethyl)-glycine unit. As a result, PNA:DNA duplexes exhibit higher stability than the corresponding DNA:DNA hybrids (~1.5 degrees Celsius per base pair) due to lack of the inter-strand repulsion between DNA phosphate groups. This is advantageous to improve the hybridization specificity of shorter oligomers. Single-stranded oligomers can include or be exclusively PNAs. Suitable double-stranded oligomers may be constructed entirely from PNAs or from mixed PNA and DNA, or mixed PNA, DNA, and RNA oligomers.

Linker region 403, adjacent to spacer region 405, is designed in view of its charge, length, and hydrophobicity and salvation. Concerning charge, it is preferable the linker region be substantially neutral in order to increase hybridization of target nucleic acids and stacking oligomers to probes. The negatively charged phosphodiester backbones of hybridization region 402, core region 401, and optional spacer region 405, especially when concentrated in a limited area of a support, can repel the similarly negatively charged backbone of a target nucleic acid. See, e.g., Schepinov et al., 1997, Nuc. Acids Res. 25:1155–1161. Consequently to reduce such concentrated negative charge and electrostatic interaction of the linker with the remainder of the probe, it is preferably that the linker be substantially neutral. Further, to minimize total probe charge, it is preferred that linker region 403, partially or wholly replace 405, as advancements are made in the technology for synthesizing longer and stable linkers. Concerning length, the linker region should be of a length such that, combined with the length of the spacer region, stearic hindrance of target nucleic acid or stacking oligomer hybridization due to probe supports is minimized.

Accordingly, it is preferable that linker region 408 not be an oligonucleotide. It is most preferable that linker region 405 be a hydrophobic aliphatic chain, more preferably an aliphatic chain having a length of the form of $(CH_2)_6$ to $(CH_2)_{40}$, which have an extended length of approximately 50–100 Å, and most preferably an aliphatic chain of approximately the length $(CH_2)_{12}$ to $(CH_2)_{20}$. Alternately, the linker can be substituted with neutral groups in order to increase its hydrophilic character. Such linkers can be synthesized from monomeric units including propanediol, di- or tri-ethylene glycol. Either aliphatic or substituted aliphatic chains can be covalently attached to the terminal nucleotide of spacer region 405 according to such chemistries as synthesis of the last dT residue in the space region with a modified phosphoramidite containing the appropriate linker and functional group as a modification.

In addition, the linker can include a segment that permits chemical cleavage of the probe from the UDA support. For example, incorporation of the reagent (2-cyano-ethoxy)-2-(2'-O-DMTr oxyethylsulfonyl) ethoxy-N,N-diisopropylaminophosphine during linker synthesis permits selective cleavage of the oligomer by treatment with ammonia. See, e.g., Schepinov et al., 1997, Nuc. Acids Res. 25:1155–1161. A cleavable linker section can aid in the isolation and identification of rare species of nucleic acids, even single copies of nucleic acids in the sample. Specifically, after target nucleic acid ligation according to the h/l method, isolation is achieved by cleavage of the linker followed by PCR amplification of the ligated target and Sanger sequencing of the PCR product. This method can be applied to those probes that have low signals difficult to detect by the preferred optical detection methods described below. Probes with cleavable linkers can be mixed with non-cleavable probes and bound together to the same regions of a UDA or a separate array can be constructed having exclusively probes with cleavable linkers.

The terminal component of a probe is function group 404, which is covalently attached to linker region 403, either at or near its terminus. Functional group 404 is chosen to readily bind to the derivitization provided on the surface of the array supports with sufficient energy to resist the washes used in the h/l and SIL methods of this invention. In particular, covalent attachment is preferable with alternative binding interactions, such as that of biotin with streptavidin/avidin less preferable. Functional group 404 can include such active moieties as amino, sulfhydryl, biotin, dinitrophenol, and so forth. In the case of amino, the surface can be derivitized with thiocyanate, isothiocyanate, or carboxylic acids. In the case of biotin, the surface can be derivitized with avidin or streptavidin. In the case of dinitrophenol, digoxigenin, or other hapten, the surface can be derivitized with an antibody to these moieties. In the case of glass surfaces, derivitized with phenylisothiocyanate groups, an amino functional groups is preferred. Alternately, in the case of a surface with bound streptavidin, a biotin functional group is preferred.

Exemplary probes are illustrated in the Examples set forth in Section 6. Such probes can be synthesized by well known methods for synthesis of polynucleotides, such as, e.g., phosphoramidite chemistry performed by a commercial synthesizer, exemplary synthesizers being obtainable from Applied BioSystems, Inc. (Foster City, Calif.). The linker and functional group can be added by a modifying the phosphoramidite used to link the last nucleotide to also contain the appropriate linker and functional group. See, e.g., Schepinov et al., 1997, Nuc. Acids Res. 25:1155–1161. Alternately, the probes of this invention can be supplied by commercial suppliers, such as, e.g., Biosynthesis, Inc. (Lewisville, Tex.).

In embodiments of this invention where DNA oligomers are specified for performing functions, including use in probes or for hybridization and chain elongation priming, alternative oligomers can be used that comprise those of the following nucleotide mimics which perform similar functions. Nucleotide mimics are subunits (other than classical nucleotides) which can be polymerized to form molecules capable of specific, Watson-Crick-like base pairing with DNA. The oligomers can be DNA or RNA or chimeric mixtures or derivatives or modified versions thereof. The oligomers can be modified at the base moiety, sugar moiety, or phosphate backbone. The oligomers may include other appending groups such as peptides, hybridization-triggered cleavage agents (see, e.g., Krol et al., 1988, *BioTechniques* 6:958–976), or intercalating agents (see, e.g., Zon, 1988, *Pharm. Res.* 5:539–549). The oligomers may be conjugated to another molecule, e.g., a peptide, hybridization triggered cross-linking agent, transport agent, hybridization-triggered cleavage agent, etc.

The oligomers may also comprise at least one nucleotide mimic that is a modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. The oligomers may comprise at least one modified sugar moiety selected from the group including but not limited to arabinose, 2-fluoroarabinose, xylulose, and hexose. The oligomers may comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. Alternatively, the oligomers may be constructed from DNA mimics which have improved hybridization energetics compared to naturally occurring nucleotides. A preferred mimic is a peptido-nucleic acid ("PNA"), which has be previously described.

The oligomer may be an α-anomeric oligomer. An α-anomeric oligomer forms specific double-stranded hybrids with complementary RNA in which, contrary to the usual α-units, the strands run parallel to each other (Gautier et al., 1987, *Nucl. Acids Res.* 15:6625–6641).

The oligomers may contain additional modifications including, but not limited to, amino or sulfhydryl groups, fluorescent labels, metal ions, affinity labels, such as, biotin, digoxigenin, peptides, antibodies, or other labels that might allow advanced detection technologies be applicable to the present invention. These modifications may be added before, during or after the synthesis of the oligonucleotides either in precursor form, activatable form, or any other way known in the art. The modifications may be attached to either the 5' or the 3' end of the oligonucleotide or anywhere along its length. Amino modifications may include a $C_6$-amino, $C_{12}$-amino, or other spacer molecules known in the art (Maskos and Southern, 1992, *Nuc. Acids Res.* 20:1679–1684).

Oligomers of the invention may be synthesized by standard methods known in the art, e.g., by use of an automated DNA synthesizer (such as are commercially available from Biosearch, Applied Biosystems, etc.). As examples, phosphorothioate oligomers may be synthesized by the method of Stein et al. (1988, *Nucl. Acids Res.* 16:3209), methylphosphonate oligomers can be prepared by use of controlled pore glass polymer supports (Sarin et al., 1988, *Proc. Natl. Acad. Sci. U.S.A.* 85:7448–7451), etc. Oligomers may be of any base composition of known, partially unknown or degenerate sequence, and may be randomized at any position or positions along their lengths.

5.2.2 Array Physical Design

The subsection describes construction of a universal detection array. First, exemplary embodiments of the logical arrangement of a UDA are described. Second, materials and methods for constructing particular UDAs are described.

In one embodiment as previously described, a UDA is directed to recognizing all terminal subsequences of length N (typically 4 to 8) of target nucleic acids. In this case, the UDA includes $4^N$ probes with hybridization regions capable of recognizing all subsequences of length N (termed herein a "complete" UDA). For ease of description only and without any limitation, this section describes a UDA ligation chip useful for recognizing 4 base terminal subsequences, and therefore having 256 species of probes (termed herein a "256-array"). UDAs capable of recognizing longer terminal subsequences can be built from 256-array building blocks, as described subsequently. Also as described, a UDA can be directed to recognizing only certain terminal subsequences of interest. In this case, the UDA includes fewer than $4^N$ species of probes. Such an array can be simply constructed in the format of a complete UDA by including only the needed probes. If the resulting array is sufficiently sparse, then it may be rearranged into more compact formats to minimize use of support area.

FIG. 5A illustrates an exemplary arrangement for a 256-array described with respect to probe hybridization regions of sequences denoted as "$N_1 N_2 N_3 N_4$." This array is generally illustrated as including a primary observation section outlined as section 501, together with optional but preferable error-checking sections. The primary observation section can be advantageously, but optionally, configured as a rectangular array of 16 sub-arrays, each sub-array configured as a rectangular array of 16 cells in which are bound individual species of probes. According to the illustrated labeling, $N_1$ and $N_2$ vary over the possible nucleotides (A, T, G, and C in order) in a horizontal direction, with $N_2$ varying more rapidly than $N_1$. Similarly, $N_3$ and $N_4$ vary over the possible nucleotides with $N_4$ varying more rapidly than $N_3$. Therefore, each sub-array of 16 cells has probes with a given nucleotide assignment for $N_1$ and $N_3$ but with all possible nucleotide assignments for $N_2$ and $N_4$. In particular, cell 502 has a probe with a hybridization region of sequence TGGT.

The rectangular (or square) arrays illustrated in FIG. 5A are advantageous in that each cell has easily determined cell coordinates, and that the hybridization target is easily predictable from these coordinates. Other geometric designs with these properties are equally preferable.

An error checking section includes further cells designed to confirm that a signal observed from a particular cell in the primary observation array is in fact due to hybridization with the probe and not to an artifact, such as non-specific binding to the probe or to the substrate in the vicinity of the probe or to a mis-hybridization with a probe hybridization region.

Such confirmation is a preferred feature of a UDA. Error-checking cells contain a mixture of probes, each with a particular hybridization region. If a correct hybridization occurs to a cell in the primary observational array containing probes having a particular hybridization region, then hybridization should also occur to all error-checking cells also containing probes with this particular hybridization region. Hybridization should not occur to error-checking cells not containing probes with this particular hybridization regions. Many schemes can be used for combining multiple probes into error-checking cells according to various error checking codes.

In a preferred embodiment, error-checking cells contain hybridization regions fully degenerate on one or more nucleotides (termed herein "degenerate" probes) to which a target nucleic acid should hybridize if it also hybridizes to a cell in the primary observation array with probes having a unique hybridization region sequence. For example, if a target nucleic acid hybridizes with probes in cell 502, which have hybridization regions of the sequence TGGT, then it should also hybridize with cells containing such degenerate probes as NGGT ("N" is taken to stand for all nucleotides, and "NGGT" represents the particular sequences AGGT, TGGT, CGGT, GGGT, TNGT, TGNT, TGGN, NNGT, NGNT, and so forth, and it should not hybridize with cells containing such degenerate probes as NCGT, NAGT, NTGT, GNGT, and so forth.

Accordingly, a complete error checking section can include cells with all degrees of degeneracy. In the following, nucleotide positions marked by "-," and not marked by "N," are taken to have fixed assignments in any one cell. Error checking cells of first-degree of degeneracy include those with sequences: N---, -N--, --N-, and ---N. Error checking cells of second-degree of degeneracy include those with sequences: NN--, N-N-, N--N, -NN-, -N-N, and --NN. Error checking cells of third-degree of degeneracy include those with sequences: NNN-, NN-N, N-NN, and -NNN. Finally, the error checking cell of fourth-degree of degeneracy has the sequence NNNN, but is of little interest.

In an actual embodiment, the error checking section of a UDA can include one or more cells of one of more of these degrees of degeneracy. It is preferred that sufficient error-checking cells be included so that every cell of the primary observational array is checked by at least one error-checking cell. Depending on the configuration of the primary array, such error-checking cells can be arranged within and adjacent to the primary array. For example, in FIG. 5A first-degree groups -N-- and ---N are arranged adjacent to the sub-arrays of 16 cells of the primary array. For example, group 503 includes cells TAGN, TTGN, TGGN, and TCGN of the first-degree group ---N, and group 504 includes cells TNGA, TNGT, TNGG, and TNGC, of the first-degree group -N--. Therefore, hybridization at cell 502, if correct, should be confirmed by hybridization in error-checking cells TGGN and TNGT of groups 503 and 504, respectively. Further, the 16 cells of the second-degree groups NN-- and --NN are arranged in vertical column 505 and horizontal column 506, respectively, adjacent to the primary observational array. For example, sub-column 507 includes cells NNGA, NNGT, NNGG, and NNGC, and sub-column 508 includes cells TANN, TTNN, TGNN, and TCNN. Therefore, hybridization at cell 502 should be confirmed by hybridization in error-checking cells NNGT and TGNN of sub-columns 507 and 508, respectively.

Further error-checking cells can be included adjacent to the primary observational array. FIG. 5A illustrates an exemplary embodiment with a complete set of such cells of all but the fourth degree groups. Thus, two 64-cell arrays 509 and 510 can include first-degree groups N--- and --N-; four 16-cell arrays 511 can include the remaining second-degree groups N-N-, N--N, -NN-, and -N-N; and the four 4-cell arrays 512 can include all the third-degree groups.

If a signal from a cell of the primary observational array is not confirmed by the error-checking cells present in an implementation of a UDA, it is preferably ignored as artifactual. Preferably such a signal is confirmed by at least two error-checking cells, by at least four cells, by at least 50% of the possible error-checking cells, by at least 75%, by at least 90%, or by at least 100% of the possible error-checking cells.

Advantageously, a UDA can also include alignment cells to aid in signal detection. Such cells have labeled probes and are positioned at known locations in order to provide a signal which the detection apparatus can use to position itself with respect to a UDA. For example, cells are positioned at periphery of the observational and the error-checking section in order to provide orienting signals for the detection apparatus. In FIG. 5A, cell 513 is such a cell.

A UDA capable of recognizing all terminal subsequences of length 5, and having 1024 species of probes (a "1024-array"), can be constructed from 256-array building blocks. FIG. 5B illustrates an exemplary embodiment of a 1024-chip including a primary observation array of four quadrants, each quadrant similar to a 256 grid as illustrated in FIG. 5A. Probes in each quadrant, however, have hybridization regions of length 5, which are constructed from hybridization regions of the 256-array of length 4 by adding an extra nucleotide. Preferably, in each quadrant the extra base is uniformly either A, T, G, or C. Error checking can be performed separately on the four nucleotides which vary within each quadrant and on the fifth nucleotide. Within each quadrant, error checking can be performed as previously described. The error-checking probes can contain the fifth nucleotide of that array in order to check its hybridization. Alternatively, if these probes are degenerate at the fifth nucleotide, additional error checking on the fifth nucleotide can be performed by error checking cells of any degree of degeneracy, which, however, are not degenerate in the fifth nucleotide. Illustrated is an exemplary error-checking 256-array quadrant having cells of the sequence N----. For example, a hybridization signal recognizing a sequence TGGTA is confirmed in this array by a signal from error-checking cell NGGTA. Numerous other error checking possibilities degenerate in various combinations of nucleotides other than the fifth nucleotide include cells having such sequences as -N---, NN---, NNN--, and so forth, all of which can be applied to 1024-arrays.

UDAs of higher complexity, such as arrays having 4096, 16,384, 65,536, and more species of probes, can be constructed in a similar recursive manner. An array of increased complexity being constructed from four arrays of the immediately preceding complexity along with any optional extra error-checking cells. For example, a 4096-array can be constructed with a primary observational section of four 1024-arrays together with an optional array of error-checking cells for the sixth nucleotide of the hybridization region.

The remainder of this subsection describes methods and materials for the construction of UDAs according to the previous logical designs. In particular probe surface densities, surface binding chemistry, probe deposition protocols, and certain binding alternatives are described.

For implementations of a UDA on a planar surface, in order to maximize hybridization signals, it is important to deposit probes with an appropriate surface density. In general, lower probe surface densities hybridize with fewer target nucleic acids, and therefore, typically lead to less optimum signal intensities. Additionally, lower probe surface densities can become saturated with target nucleic acids, leading to excessively non-linear response of the hybridization signal to initial target nucleic acid concentrations. However, higher probe surface densities lead to higher stearic interference and increased charge repulsion between the oligonucleotide regions of the probes themselves and the target nucleic acids and stacking oligomers, as well as to interference with ligase enzymes used in hybridizing to a UDA. At too high surface densities, this interference and repulsion can also lead to less optimum signal intensities. One aspect of the instant invention is the discovery that these competing effects are balanced over a broad range of low to intermediate surface densities, all of which lead to adequate signal intensity from hybridized target nucleic acids along with economical use of probe molecules. This intermediate surface density is preferably determined empirically, separately in the case of each surface and surface treatment. This can be performed by varying the deposited surface density and observing test hybridization signals.

The preferred probe binding chemistry and protocols is next described. In general, attachment proceeds by first processing the planar surface with a derivitization method that provides functional groups on the planar support which are adapted to readily bind to corresponding functional group 404 provided on the probe. Second, the probes are then deposited on the derivitized planar support in conditions adapted to cause this binding. In a preferred embodiment of this invention, probe arrays are prepared on derivatized glass surfaces. Glass surfaces are preferred because they are readily available and inexpensive, possess relatively homogeneous chemical surfaces of understood properties, and are amenable to surface treatments using a variety of chemistries. See, e.g., Fodor et al., 1991, Science 251:767–773; McGall et al., 1996, Proc. Natl. Acad. Sci. USA 93:13555–13560. Numerous surface derivitization methods are known for glass. In particular where the probes have an amino functional group, glass surfaces can be derivitized to have such surface functional groups as aldehyde, ketone, thiocyanate, isothiocyanate, phenylisothiocyanate, or carboxylic acid groups (Chrisey et al., 1996, Nuc. Acids Res 24:3040–3047). Glass surface derivitization can be performed according to these various known methods, but is preformed, preferably, by the introduction of amino-reactive phenylisothiocyanate groups onto glass surfaces for binding with amino containing probes (Guo et al., 1994, Nuc. Acids Res. 22:5456–5465).

Probe solutions are then deposited on glass surfaces so derivitized, and are reacted with amino functionalized probes under conditions that promote the binding of amino and phenylisothiocyanate groups. The probe concentrations applied to the surface can be varied to achieve desirable final surface densities. Suitable probe concentrations can be determined empirically by anchoring oligonucleotide solutions of various initial concentrations and hybridizing with test samples of labeled target nucleic acids in order to obtain suitable signal intensities. See, e.g., Section 6.5. It is preferred to use lower probe deposition-solution concentrations that remain consistent with adequate hybridization signals. Such lower concentrations make economical use of probes, which can become cumulatively expensive, especially for large arrays.

A wide range of effective initial concentrations of probe deposition-solutions can be employed in this invention. For use in the following preferred protocol, a less preferred range of concentrations is 200 $\mu$m to 20 mM, a preferred range of concentrations is 20–200 $\mu$m, and a more preferred range of concentrations is 2–20 $\mu$m. (Other preferred concentration ranges are 2 $\mu$m to 40 $\mu$m, 60 $\mu$m, 80 $\mu$m, 100 $\mu$m, and 150 $\mu$m.) All these concentrations give adequate hybridization signals, the lower concentrations being preferred in order to make quite economical use of probes. In particular, those probe deposition-solution concentrations below 2 $\mu$m that are found to give adequate hybridization signal intensities are even more preferred. (At the less preferred probe deposition-solution concentration of 5 mM the probe surface density has been observed to be approximately 500 $\text{Å}^2$ per probe molecule, or approximately 0.3 picomole/square mm (Guo et al., 1994, Nuc. Acids Res. 22:5456–5465)).

A preferred protocol for depositing arrays of probes on derivatized glass proceeds by the following general steps. First, glass surfaces are carefully cleaned glass and prepared to be in a defined and reproducible surface chemical state. Then available reactive sites on this prepared glass surface are saturated with amino groups by use of an amino containing silane. Substantially all these surface amino groups are converted into amino-reactive groups by reaction with the bi-functional amino-reactive reagent 1,4-phenylene diisothiocyanate ("PDC"). Onto this controlled and reproducible amino-reactive derivitized glass surface, aliquots of buffered probe solutions of carefully selected concentrations are deposited and subjected to binding conditions. Finally, unbound amino-reactive groups are passivated by reaction with an amino containing reagent which does not produce a detectable signal during subsequence observation steps. Steps of this protocol are described in details with respect to the preferred reagents used. This invention can be adapted to other reagents with similar chemical functions.

Accordingly, in more detail, in a first step glass surfaces are cleaned and prepared. Glass slides, preferably of at least 1.8×1.8 cm size, can be used as glass surfaces in this protocol. Suitable slides are, for example, Fisher-Finest slides (Fisher Scientific, Hampton, N.H.). Surface cleaning and preparation is an important step and includes an initial cleaning with a general purpose laboratory glass cleaning reagent. A preferred such cleaning reagent is Rhodite™, House of Rhodes (Hicksville, N.Y.). Initial cleaning is followed by a strongly alkaline wash by, e.g., soaking in 1–4 M (or higher) NaOH or other equivalent alkali for 3–6 hours, preferably slides are soaked in 1 M NaOH for 4 hours. A final surface cleaning and surface preparation step is washing in a strong acid, which leaves the surface in a definite and reproducible chemical state. Preferably, slides are soaked in concentrated nitric acid (greater than approximately 65% concentration) for from 4–16 hours. Alternatively, other equivalently strong acids (pH less than approximately 1), such as concentrated hydrochloric or sulfuric acids, can be used. Following cleaning and preparation, slides can be stored in a vacuum desiccator until the next protocol step.

The next two protocol steps bind the preferred phenylisothiocyanate to the glass surfaces via an intermediate silanization step which contributes amino groups to the glass surface. Silanization is preferably accomplished by immersing the slides (for example 20 slides in 200 ml of solution) in 3-aminopropyltrimethoxysilane solution (Sigma-Aldrich Chemicals, Milwaukee, Wis.), 1% in 95% acetone in water, for approximately 2 mins. Alternatively, other times and concentrations that achieve surface site saturation can be used, such as 3-aminopropyltrimethoxysilane concentrations of 0.5% to 5% can be used with corresponding immersion times of 3–4 hours down to 1 minute.

Alternative amino-silanes generally suitable for the purpose of amino-derivitizing a glass surface include those with the formula $(R_1R_2)NR_3Si(R_4R_5R_6)$, which has the following structure.

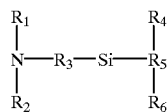

Preferably, at least one of $R_1$ and $R_2$ is an H. $R_3$ can be an optionally substituted aliphatic chain of from $C_1$ to $C_{10}$, and is preferably a propyl or a butyl. At least one of $R_4$, $R_5$, and $R_6$ is a R—O group, where R is an aliphatic chain, preferably a methyl or an ethyl. The remaining ones of $R_1$, $R_4$, $R_5$, and $R_6$ can be optionally substituted aliphatic chains of from $C_1$ to $C_{10}$. Exemplary silanes include the following compounds: 4-aminobutyldimethylmethoxysilane, 3-(1-aminopropoxy)-3,3-dimethyl-1-propenyl-trimethoxysilane, 3-aminopropyltris(methoxyethoxyethoxy)-silane, n-(3-acryloxy-2-hydroxypropyl)-3-amino-propyltriethoxysilane, n-(2-aminoethyl)-3-aminopropylmethyldimethoxysilane, n-(2-aminoethyl)-3-aminopropyltrimethoxysilane, n-2-(aminoethyl)-3-aminopropyltris(2-ethyl-hexoxy)silane (90%), 3-(1 -aminopropoxy)-3,3-dimethyl-1-propenyl-trimethoxysilane, 3-aminopropyltris(methoxy-ethoxyethoxy)-silane, 3-aminopropyldimethylmethoxy-silane, 3-aminopropylmethyldiethoxysilane, 3-amino-propyldiisopropylethoxysilane, 3-aminopropyltrimethoxy-silane, and 3-aminopropyltris(trimethylsiloxy)silane.

Next, the amino-derivitization introduced by the silanization is then converted to amino-reactivity by reacting the surface amino groups with PDC in order to couple phenyl-isothiocyanate groups to the surface amino groups. Conditions are chosen so that substantially all amino groups are so converted. Preferably, this is accomplished by immersing the slides in PDC solution (Sigma-Aldrich Chemicals, Milwaukee, Wis.), 0.2% in 10% pyridine/dimethyl formamide, for 2 hr with occasional stirring. Alternatively, other times and concentrations that substantial total conversion of the surface amino groups can be used, such as PDC concentrations of from 0.05% to 1 % with corresponding immersion times of 3–4 hours to 10 mins. After methanol washing, the slides can be stored in a vacuum desiccator.

Fourth, probes are deposited and bound to the derivitized slides. Probes are dissolved in an alkaline buffer (with a pH of 8–10 preferably approximately 9) at the desired and carefully chosen concentration (in the preferred ranges previously described). A sodium carbonate/bicarbonate solution (approximately 100 mM) is a suitable buffer. Aliquots of the probe deposition-solutions are then deposited on the slide surfaces. For definiteness and without limitation, each of the four 256-arrays of a 1024-array can be deposited as follows. For ease of handling, the 256 probes of one array can be placed individually into wells of a 384-well microtiter plate. An aliquot of each probe solution is then transferred from its well to its designated position on the array being deposited. Preferably, from 2 nl to 2 $\mu$l, and more preferably 25 nl, of probe solution is transferred into each cell of the array. The preferred cell size (diameter) obtained by transfer of 25 nl of probe solution is approximately 200 $\mu$m. With such a cell size, a preferred center-to-center distance of the cells is approximately 600 $\mu$m. With these sizings, the dimensions of 256-array is approximately 9.0 mm×9.0 mm. In the case that only a 256-array is to be deposited, only a single 256-array in one quadrant, or four identical 256-arrays in four quadrants, can be deposited on the 1.8×1.8 cm glass surface. In the case of a larger 4096-array, the sizings must be reduced in order to fit on a 1.8 cm×1.8 cm surface. For a 4096-array, preferably, approximately 5 nl or less of probe solution is deposited at a center-to-center distance of approximately 150 $\mu$m to obtain cells of average diameter approximately 100 $\mu$m. Arrays of larger sizes are preferably accommodated on more than one 1.8 cm×1.8 cm surface, or most preferably, generated using the alternative implementation, namely photolithography (as described below).

Deposition of controlled aliquots of the probe solutions can be performed according to several methods. The size of aliquots of probe solution is chosen in view of the desired spot size. For example, for a spot size of approximately 100 $\mu$m, approximately 2–8 nl of probe solution is deposited; for a spot size of approximately 200 $\mu$m, approximately 8–32 nl of probe solution is deposited. In a simplest method, adaptable to arrays of lower complexity, from 25 to 200 nl of probe solution is applied to a glass surface with a pipette or by dipping the tip of a needle into the DNA solution and touching it to the glass surface. Tips can be micro-machined to deliver aliquots down to approximately 5 nl. The latter method is preferably automated using a standard laboratory robot and a precise X-Y-Z table for accurate relative positioning of the glass surface, such as can be supplied by, e.g., T-Tech, Inc. (Atlanta, Ga.).

After deposition, probe molecules with amino functional groups are bound to the amino-reactive surface phenyl-isothiocyanate groups by gentle hydration by, for example, exposure to a humid atmosphere. For example, the slides can be incubated for 1–3 hours (preferably 1 hr) at 37° C. in a petri dish containing a piece of Whatman #1 paper soaked in deionized $H_2O$ and not in contact with the arrayed slide. The fifth and last step passivates any remaining amino-reactive groups by reacting them with a non-detectable (for example, non-fluorescent) amino bearing reagent, such as a primary amine or ammonia. Preferably, passivation is by an ammonia wash with 1% $NH_4OH$ for 2 minutes at room temperature. Alternatively, 0.1% to 5% $NH_4OH$ can be used with corresponding wash times of 1 hours to ½ min. Passivation concentrations and times are chosen so that substantially all remaining amino-reactive groups are reacted.

This invention is adaptable to other supports, appropriate derivitization methods, and corresponding probe functional groups besides the just described, derivitized, planar glass surfaces. Possible alternative probe supports include planar supports such as nitrocellulose, nylon, acrylamide gel, polystyrene, silicon dioxide, the latter perhaps configured as part of a micro-fabricated device, as well as non-planar supports such as controlled-pore glass beads, activated dextran, polystyrene or latex beads, activated sephadex or sephacryl beads, or microtiter plates. Before contacting the probes with the supports, support surfaces are first activated by chemical treatments so that specific surface functional groups are present that provide for a desired coupling chemistry with a functional group present on probes. For example, probes with a conjugated biotin are, preferably, anchored to surfaces containing avidin or streptavidin. Streptavidin coated beads for magnetic separation are available from Dynal AS (Lake Success, N.Y.). For another example, an aldehyde or carboxylic acid functional group on probes can be bound to latex microspheres containing hydrazide residues. See, eg., Kremsky et al., 1987, Nucleic Acids Res 15:2891–2909.

In particular, preferable beads are controlled-pore glass beads, which can be derivitized and used for probe attachment by the same methods as planar glass surfaces.

In another example of an alternative support, probes, preferably with cleavable linker regions (see previous subsection), are immobilized on derivatized controlled pore glass beads. See, e.g. Maskos and Southern, 1992, Nuc. Acids Res. 20:1679–1684. An array, for example a 256-array, can be conveniently arranged in wells of a microtiter plate. For detection of rare target nucleic acids, probe oligomers are ligated to complementary nucleic acid targets present in a complex sample mixture, cleaved preferably by ammonolysis, and amplified by PCR using primers complementary to known regions of the probe and the target nucleic acid (e.g., complementary to primer sequences). Probe hybridization sequences can be chosen to recognize target nucleic acids of known sequence that may be present in the sample, or alternatively, can be chosen to select target nucleic acids previously recognized or suspected from gene calling. Section 5.1 describes the selection of hybridization region sequences in this case. The implementation is advantageous in expression and differential gene expression monitoring where the amount of sample available is limited, such as, single cells (for example single neurons), early zygotic developmental stages, and so forth.

For construction of arrays of complexity greater than 4096, for example arrays with 16,384, 65,536, or more species of probes, it is preferable to replace the previously described method of mechanical deposition process with a method involving direct synthesis of probes on substrates. Direct synthesis of deoxynucleotide oligomers on derivitized glass using a photolithography and light activated oligodeoxynucleotide synthetic chemistry in cells down to 100 $\mu$m×100 $\mu$m is known in the art. See, e.g., Lockhart et al., 1996, Nature Biotechnol. 14:1675–1680; Maskos et al., 1992, Nuc. Acids Res. 20:1679–1684. Such synthetic techniques permits an array of 16,382 probes to be synthesized on a single 1.8 cm×1.8 cm glass surface, and an array of 65,536 probes to be synthesized on one 2.5 cm×2.5 cm glass surface or on two 1.8 cm×1.8 cm glass surfaces. Using photolithographic techniques conventional in the semiconductor industry, arrays with densities of $10^6$ sequences/cm$^2$ can currently be synthesized, corresponding to cell sizes of 5–10 $\mu$m. See, e.g., Willson, 1994, in Thompson et al, eds., *Introduction to Microlithography*, 2nd ed., Am. Chem. Soc., Washington, D.C., pp. 139–267. McGall et al., 1996, Proc. Natl. Acad. Sci. USA 93:13555–13560 report successful synthesis in 8 $\mu$m cells. This invention is adaptable to these alternate methods for direct synthesis of probes on surfaces.

5.2.3 Method of Hybridization/Ligation

Universal device arrays ("UDAs"), consisting of arrays of probes and constructed according to the previous descriptions, are used for the parallel and simultaneous observation of terminal subsequences of target nucleic acids from a complex mixture of target nucleic acids. For example, the mixture of target nucleic acids can be prepared according to the methods of Section 5.1. Target nucleic acids hybridize to the probe array according to complementarity between their terminal subsequences and the hybridization regions of the probes. Upon this hybridization, UDAs can be used to generate terminal subsequence recognition signals according to various methods, preferred methods being the hybridization/ligation method ("h/l" method) and the strand-invasion ligation method ("SI ligation method" or "SIL method"). According to the h/l method, which is described in this subsection, a UDA can recognize a single-stranded terminal subsequence. According to the SIL method, which is described in the next subsection, a UDA can recognize a terminal subsequence which includes a single-stranded terminus adjacent to a short double-stranded region.

Both the h/l and SIL methods use various enzymatic and physical effects to improve hybridization, and thereby recognition signal, specificity and discrimination. The preferred effects utilized include ligase enzyme specificity and base stacking interactions. Concerning ligase specificity, nucleic acid ligase enzymes join nicks in nucleic acid strands of DNA hybridized to a complementary strand. Ligases are known in the art to discriminate between complementary and non-complementary nicked regions. In fact, ligation rates for exactly complementary double-stranded nucleic acids are 10 to 24 times greater than for double-stranded nucleic acids with even one base-pair of mismatch See, e.g., Broude et al., 1994, Proc. Natl. Acad. Sci. USA 91:3072–3076. This discrimination is greatest within 2 or 3 nucleotides of the nick to be ligated, gradually decreasing with increasing distance from the ligation point, and is retained even in the presence of an excess of unspecific DNA fragments containing non-complementary single-stranded regions. See, e.g., Luo et al., (1996) Nucleic Acids Res. 24:3071–3078. In the SIL method, a single ligation between a stacking oligomer and one strand of a hybridized target nucleic acid is used to improve discrimination. In the h/l method, ligation can occur with both strands of a hybridized nucleic acid at both ends of a single-stranded terminal subsequence. Thus, this latter method can advantageously employ the enhanced ligase discrimination over an entire 4 to 6 nucleotide, single-stranded terminal subsequence.

This invention also advantageously exploits the effects of base stacking interactions on hybridizations. As is known in the art, when two single-stranded nucleic acids hybridize in an adjacent configuration onto a third single-stranded nucleic acid, the additional interaction energy of the adjacent bases contributes to overall hybridization stability. See, e.g., Lane et al., 1997, Nuc. Acids Res. 25:611–616; Parinov et al., (1996) Nuc. Acids Res. 24:2998–3004. The present invention utilizes the advantages of stacking interactions to enhance ligation efficiency. In both the h/l and SIL methods, stacking interactions are present at the ends of both strands of a correctly hybridized target nucleic acid, and thereby, increase the hybridization stability of this complex.

Stacking oligomers (oligomer 612 in FIG. 6A) are designed to cause stacking interactions with a correctly hybridized target nucleic acid and to have a Tm sufficiently high for the subsequent wash steps of the h/l and SIL methods. Stacking oligomers are, preferably, approximately at least 18 nucleotides long, and are hybridizable to core region 601 of the probe oligomer in a configuration such that the end of the stacking oligomer is flush with the end of the probe core region, thereby being contiguous with the probe hybridization region. Alternately, the stacking oligomer can have a length between 5 and 24 nucleotides. The sequence of the stacking oligomer is chosen for increased hybridization stability (Tm at least above 40–45° C. as described in Section 5.2.1) with no likely secondary structure that might impede hybridization. Empirical rules are available for calculating duplex stabilities and likelihood of secondary structure (Wetmur, 1991, Crit. Rev. Biochem. Mol. Biol. 26:227–259). The sequences of stacking oligomers and the complementary core region are chosen in view of these rules and the previous design goals. See Section 5.2.1.

Stacking oligomers constructed according to the previous description (18 nucleotides or more) permits the use of high stringency washes to distinguish true signals from background. High stringency washes are advantageous to remove background signals due to both mis-hybridized (and therefore not ligated) targets and targets non-specifically bound to the probe oligomers, the substrates, or other components of a UDA, and to leave only true signals due to correctly hybridized and ligated target nucleic acids. (Mis-hybridizations occurs when hybridization does not produce a complementary structure of form of FIG. 6A) In those direct labeling methods in which a reporter moiety becomes covalently attached to a probe bound to the surface of a UDA as a result of ligation, the highest stringency washes can be used. In those indirect labeling methods in which a reported moiety is attached to a strand of 24–54 bases, derived from ligation of a stacking oligomer to a strand of a target nucleic acid, hybridized to the bound probe, wash conditions are less stringent, in particular so as not to denature the 24–54 base pair double stranded nucleic acid. This double-stranded product is designed (the lengths and sequences of stacking oligomer and the probe core region) to be stable at least up to 55° C. In contrast, all washes should be at least sufficiently stringent to denature all mis-hybridized target nucleic acids. As these consist of only 4–8 base pairs, they are not stable over 25–30° C.

Such probe, stacking oligomer, and target nucleic acid designs allow a UDA to achieve a high degree of mismatch discrimination, and therefore specific and reliable recognition of short terminal subsequences. Other means for increasing hybridization specificity and reliability adapted to this invention includes an alternate enzyme-catalyzed step, preferably employing a DNA polymerase. DNA polymerases are known in the art as enzymes that incorporate, in a template-dependent manner, nucleotides to the free 3'-end of a duplex nucleic acid fragment. The discrimination factor for extension by DNA polymerase was found to be equal to or higher than that for a ligase. See, e.g., Broude et al., 1994 Proc. Natl. Acad. Sci. U S A 91 :3072–3076. Specifically, this invention is adaptable to the use of a DNA polymerase after the ligation step to increase specificity, or recognition of hybridization mismatches, at locations more distant from the point of ligation. For example, using a DNA polymerase with labeled ddNTPs to extend the sequence of a stacking oligomer by a single base, determines the nucleotide adjacent to the end of the stacking oligomer from the signals from the ddNTPs.

In a less preferred implementation of this invention, direct ligations are performed in the absence of a stacking oligomer. In this case, stacking interactions still occur at the end of one strand of a target nucleic acid.

Turning now to the process details of the hybridization/ligation method, FIG. 6A illustrates the hybridized nucleic acid structure (in general the "hybridization structure") created according to this method. This structure includes target nucleic acid 610, probe 611, and stacking oligomer 612. Target nucleic acid 610 includes hybridized strands 614 and 615 with single-stranded terminus 616, label moiety 617 (in the case of "direct labeling"). Hybridization region 618 of probe 611 is complementary and therefore hybridized with single-stranded terminus 616. Probe 611 is anchored to a discrete cell in a planar array by a chemical interaction (preferably a covalent interaction) between a schematically-represented, surface derivitization moiety 603 and functional group 619, which is conjugated to oligomer 611. To permit ligation, the oligomers used herein have appropriate 5'-phosphates, in particular at nucleotide 620 on probe 611 and at nucleotide 621 of target nucleic acid strand 614. Stacking oligomer 612 has a sequence complementary to core region 601 of probe oligomer 611, and thereby hybridizes adjacent to hybridization region 618. Stacking interaction occur across the nicks 604 and 605. Activity of a nucleic acid ligase enzyme then joins the two nucleic acid strands at nicks 604 and 605, resulting in the covalent attachment of target strand 615, with label moiety 617, to the probe oligomer and of the target strand 614 to stacking oligomer 612. Thereby, the probe oligomers that have recognized single-stranded termini in the nucleic acid sample become labeled with the label moiety on the target nucleic acid. This labeling (termed herein "direct" labeling) by which the probe oligomers attached to the substrate become labeled, is the preferred labeling mode. Following ligation, a very high stringency wash can be employed to remove all nucleic acids other than the covalently attached probes.

An alternative labeling (termed herein "passive" labeling) conjugates label moiety 602 to stacking oligonucleotide 612. Then, upon ligation, ligated strands 614 and 612, which are hybridized to ligated strands 615 and 611, become labeled with moiety 602. Following ligation, a high stringency wash selectively removes mis-hybridized or non-specifically bound nucleic acids from the UDA, while not disturbing hybridized ligated strands 612 and 614 resulting from correctly recognized target nucleic acids.

It is advantageous for the conditions of the hybridization/ligation method (and also for the subsequently described SIL method) to be selected such that the UDA provides a quantitative signal of the amount of each species of target nucleic acid in a sample. To achieve such quantitative results, it is advantageous that the amount of hybridization/ligation product, and thus the detected hybridization, is approximately a linear function of the concentration of the target nucleic acid species, or is at least monotonically dependent upon this concentration.

In order to achieve such a dependence, first, the relative concentrations of probe and target are so adjusted as not to saturate or deplete either species during the hybridizations/ligations (and SIL) reactions. This is achieved by maintaining concentrations of unique probe oligomers in each cell of the array that are significantly higher (preferably 100 to 1000 fold molar excess) than the concentrations of any species of target nucleic acid. In comparison, the relative concentrations of any target species in solution is orders of magnitude lower, particularly in view of the fact that the target sample is a collection of several unique sequences, preferably, between 100–300. For this reason, even at rather high initial concentrations of the target mixture (1 pmol per hybridization/ligation reaction), the projected amount is approximately 10 fmol ("femto-moles") or lower, for a single unique species in the interaction mixture. Further, the target is contained in a solution of 10 $\mu$l (as against the probes that are immobilized) thereby decreasing the effective concentration of the target species that is in the vicinity of a matched probe by a factor of approximately 100–1000.

Second, it is advantageous that the target not become depleted during the hybridization and ligation, which would also hamper linear responsiveness. The hybridization/ligation (and SIL) reaction time is selected in view of such factors as, e.g., ligation efficiency, half life of enzyme activity, diffusion of target, depletion of reagents, etc. even for rare species in the target mixture in order that target species are not depleted during the reaction. In other words, the hybridization time is selected to be no longer than the time that expected target species become depleted by hybridization and ligation. Consequently, the amount of the hybridized and ligated target nucleic acid is approximately proportional to the initial concentration of the target. The less the target becomes depleted the more exact the proportionality. Therefore, the ligation occurs in an approximately linear range (called herein "pseudo-linear"), that in each cell is dependent upon the effective initial concentration of the target whose terminal sequence is complementary to the probe hybridization region. The same considerations apply and concentration ranges are selected for the SIL method, so that it too generates a hybridization signal proportional to the target nucleic acid concentrations. In view of ligation efficiencies, reaction times of the order of 1 to 12 hours (or more) can be appropriate.

In alternative applications, a UDA may be required only to confirm the presence or absence of particular terminal subsequences in a test sample, without indicating their relative abundances. In this case, the hybridization and ligation conditions are preferably chosen so that all available target nucleic acids are observed by the UDA. Therefore, here it is also desirable to have an excess of probe molecules over target nucleic acids (in order to drive hybridization and ligation to substantial completion). However, here, it is desirable to perform the hybridization and ligations reactions until the target nucleic acids are substantially depleted by being bound to the UDA. One of average skill will appreciate how to manipulate the kinetic parameters of the hybridization/ligation reactions to achieve desirable results for yet other applications. The same choices and considerations apply to a similar application of the SIL method.

Finally, FIG. 6B illustrates the method steps of the hybridization/ligation method. Here, exemplary target nucleic acid 610 is shown as containing a 4 base single-stranded 5' terminus with sequence TGTC. During a first hybridization step, target 610 and stacking oligomer 612 anneal with anchored probe oligomer 611 containing the terminal 4 base single-stranded 5' subsequence GACA, which is complementary to TGTC, to form double-stranded nucleic acid structure 625. Typically, hybridization occurs in a total volume of 10 $\mu$l (placed over a UDA of 1.8 cm×1.8 cm size and covered by a cover slip) of a solution containing 1 pM of target nucleic acids, 10% PEG ($M_w$ 6000), 66 mM Tris.Cl, 6.6 mM MgCl2, 10 mM DTT, 1 mM ATP and 40 mM NaCl (pH 7.5) at 25° C. for 80 min. Although nucleic acid 625 has no single-stranded gaps, it has two nicks indicated at arrows 626 and 627, at which stacking interactions occur and which are then ligated simultaneously with hybridization or during a second ligation step. Typically, ligation uses 400 units T4 DNA ligase. Preferably, the ligase is in the above solution and ligation occurs simultaneously with hybridization. A ligase enzyme concentration is chosen so that preferably further increases of enzyme concentration do not cause significantly increased ligation of hybridized target nucleic acids (i e., the amount of hybridized targets reaches a constant plateau as ligase concentration is increased), and most preferably so that at this plateau substantially all (more than 90%) hybridized target is ligated. In a subsequent wash step, stringent wash conditions release the hybridized and ligated stacking oligomer leaving single stranded moiety 629, which is labeled with the label attached to target nucleic acid. Since, preferably, a label is conjugated to the strand of the target nucleic acid now covalently attached to the probe, the stringent wash conditions can be such as are sufficient to denature and release all double-stranded nucleic acids. The detectable label remains.

In the preferred embodiment of direct labeling, UDAs are washed with 2 changes of 10 mM Tris.Cl, 1 mM EDTA (pH 8.0), and 0.1%SDS (TES) at higher than 80° C. and preferably at higher than 90° C. (hereinafter referred to as "very stringent" wash). In the alternative passive labeling method, UDAs are washed by immersing in 0.5×SSPE/0.1%SDS for 15 min at a 50–55° C. (hereinafter referred to as a stringent wash). After washing, the UDA with labeled oligomers is observed according to the methods of Section 5.2.5.

5.2.4 Method of Strand-Invasion Ligation

Another preferred method for using a universal detection array is strand invasion ligation ("SIL"). SIL is capable of recognizing not only single-stranded terminal subsequences of a target nucleic acid, as are recognized by hybridization/ligation, but is also capable of recognizing short double-stranded subsequences adjacent to the single-stranded overhangs. In contrast to h/l, which preferably generates a perfectly double-stranded structure with the target nucleic acid, the probe oligomer, and the stacking oligomer, SIL generates a double-stranded "displacement" structure. In this displacement structure, the hybridization region of the probe oligomer "invades" and hybridizes additionally with a short double-stranded portion of the target nucleic acid, "displacing" the corresponding strand of the target nucleic acid. The stacking oligomer hybridizes adjacent to the other strand of the target nucleic acid and is ligated to it with a ligase (T4 DNA ligase or Ampligase (Epicentre Technologies, Madison, Wis.)). Ligase covalently joins the opposite strand via the 3'-OH of the stacking oligonucleotide and the phosphorylated 5'-single-stranded terminus of the target nucleic acid. In this method, the probe oligonucleotides are not covalently attached to target nucleic acid strands, since the displaced strand of the target nucleic acid cannot ligate to the end of the probe.

FIG. 7A illustrates the displacement structure (a form of a "hybridization structure") created by SIL. The structure of the probe oligomer is described first. In strand invasion ligation, subsequence 718 contains bases that contact not only single-stranded terminus 716 but also additional bases in adjacent double-stranded subsequence 717 of the target nucleic acid. Therefore, the structure of subsequence 718, for the strand invasion implementation of this invention, differs from that for the h/l method in that it preferably contains two contiguous subsequences 719 and 720. Subsequence 719 is designed to hybridize with the double-stranded subsequence 717 of the target. Its length in bases is equal to the number of nucleotides of double-stranded region contained in the target, which is preferably 2–4 nucleotides long. Subsequence 720 is designed to hybridize with single-stranded terminus 716, as with the h/l method.

SIL can be adapted to cases where the sequence of the double-stranded region is either unknown or known. In case the double-stranded region is unknown, both contiguous subsequences 719 and 720 are variable (a complete UDA then including probes with hybridization regions having all subsequences of the length of subsequence 718) in order to recognize the entire unknown terminal subsequence of a nucleic acid. As an example, the overall length of the variable region of the probe, now determined together by the sum of the lengths of subsequences 719 and 720, can be 6 bases if the single-stranded region is 4 nucleotides and the double-stranded region is 2 nucleotides. In this case, a total array size of $4^6$, or 4096, probe oligomers is used for interrogation of DNA bases contained in the target population. Probe arrays of increasing complexities are used for other alternative implementations, where the lengths of the overhangs, and/or double stranded regions are greater than the specific case illustrated here. Simultaneous hybridization with target single-stranded, terminal subsequences as well as with adjacent double-stranded subsequences of target nucleic acids distinguishes the SIL method of this invention from the h/l method, which recognizes only with single-stranded terminal subsequences.

Alternately, the double-stranded region can have an entirely or partially known sequence. Here, probe oligomers are designed to contact not only the variable single-stranded terminal subsequence but also the known nucleotides of the double-stranded subsequence. Recognition of known nucleotides imparts additional hybridization stability to the displacement structure. In this case, more stringent washing conditions can be used to distinguish specific form non-specific hybridization or mis-hybridization. Probe 731 for this embodiment contains an additional constant region 721 that preferably hybridizes to known nucleotides of the double-stranded region. This region is preferably between 2 to 8 bases, and most preferably 5 bases long. The sequence of region 721 is complementary to the known double-stranded sequence. The overall number of the probes comprising an array and the total size of the array is still determined by the sum of the lengths of regions 719 and 720, since the sequence of region 721 is fixed.

FIG. 7A illustrates in more detail the displacement structure, which is created during the hybridization step of the SIL method. This structure includes target nucleic acid 710, probe oligomer 711, and stacking oligomer 712. Target oligomer 710 includes hybridized strands 714 and 715 with single-stranded terminus 716, adjacent double-stranded subsequence 724, and label moiety 717 (in the case of "direct labeling"). Single stranded terminus 716 is complementary to and hybridized with subsequence 720 of hybridization region 718 of probe 711. The probe is anchored to a discrete cell in a UDA by a chemical interaction between a schematically represented, surface derivitization moiety 703 and functional group 719 conjugated to oligomer 711. To permit ligation, target strand 714 used herein has 5'-phosphate 725. Additionally, subsequence 719 of hybridization region 718 of the probe invades into and forms complementary base pairs with the formerly double-stranded subsequence 717 of the target nucleic acid. A displacement structure is thereby created, in which subsequence 723 of strand 715 of target nucleic acid is displaced by invading probe hybridization region 718. Only nick 705 is a ligation site 705, since subsequence 723 is unable to ligate to the end of hybridization region 718. Base stacking interactions occur at nick 705, and also at the end of subsequence 719 of the probe with the junction of displaced subsequence 723 with strand 715 of the target nucleic acid.

A ligase enzyme then ligates the two nucleic acid strands at nick 705, resulting in the covalent attachment of strand 714 of target nucleic acid 710 to stacking oligomer 712, containing label moiety 702 (in the case of "passive labeling"). Thereby, the probe oligomers that have recognized both the single- and the adjacent double-stranded subsequences of the target nucleic acid can become labeled with label moiety 717 on strand 715 of the target nucleic acid ("direct labeling"), or label moiety 702 on the stacking oligomer ("passive labeling"), or with both label moieties. Either one or both labels can be used; the preferred labeling places the label on the most stably hybridized strand. Since strand 715 of the target nucleic acid cannot be hybridized more stably to the probe than the ligated target nucleic acid strand 714 and stacking oligomer 712, which links the former strand to the probe, it is preferred to at least label the stacking oligomer with label moiety 702 (passive labeling). A final washing step, which is to remove mis-hybridized and non-specifically hybridized fragments, is chosen to have a stringency that does not denature the ligated stacking oligomer from the probe. (Mis-hybridizations occurs when hybridization does not produce a complementary structure of form of FIG. 7A).

FIG. 7B illustrates the steps of the SIL method. Exemplary target nucleic acid 710 is illustrated as including 4 nucleotide single-stranded subsequence 716, having the sequence 5'-CGTC, and 4 nucleotide double-stranded subsequence 724, having the sequence 5'-ACCA. During a first hybridization step, target nucleic acid 710 and stacking oligomer 712 with a FAM label anneal with anchored probe 711 containing an 8 nucleotide hybridization region having the sequence 5'-TGGTGACG to form displacement structure 726. The terminal nucleotides 5'-TGGT of probe 711 invade into and base pair with complementary nucleotides ACCA on strand 714, simultaneously displacing the terminal nucleotides 5'-TGGT on the other strand of the target nucleic acid. The displacement structure 726 is then subject to the action of a ligase enzyme in order to link the termini of stacking oligomer 712 and strand 714 of the target nucleic acid, which has the terminal sequence 5'-ACCACTGC. Conditions for the hybridization and ligation reactions can be as described previously for the h/l method. In particular, concentrations and other conditions of the hybridization and the ligation are chosen as described in the previous section so that the hybridization signal is proportional to the initial concentrations of target nucleic acid species.

In the strand invasion ligation method, UDAs are washed twice by immersing in 0.5×SSPE/0.1%SDS for 15 min at 50° C. (hereinafter referred to as "mild" wash). The washing conditions must be sufficiently stringent to denature partial duplexes containing unligated stacking oligomers, but not so stringent that stacking oligomers ligated to target nucleic acids are denatured. After washing, the UDA with labeled oligomers is observed according to the methods of Section 5.2.5.

The SIL method are adaptable to alternate methods for performing ligations. For instance, Ampligase, a thermostable DNA Ligase (Epicentre, Madison, Wis.) catalyzes the NAD-dependent ligation of adjacent 3'-hydroxyl and 5'-phosphate termini in duplex DNA structures at elevated temperatures, at least approximately 45° C. In general, the upper limit on reaction temperatures with Ampligase DNA Ligase is determined by the Tm of the DNA substrate. Under such conditions of maximal hybridization stringency, non-specific ligation is significantly reduced. For these reasons Ampligase is advantageously employed in the present invention for the Strand Invasion ligation implementation by raising the ligation temperature to 45° C. In this system, good discrimination is obtained at mismatched positions further away from the site of ligation as compared to conventional SIL implementation with T4 DNA ligase. Further, the correlation between increase in ligation temperature and discrimination is solely related to hybridization thermodynamics and not enzyme activity. Such higher ligation temperature are less preferable in the h/l method because the shorter region of hybridization (typically 4–5 nucleotides in the case of the h/l method, instead of at least 6–7 nucleotides in the case of the SIL method) is more susceptible to denaturation and these higher temperatures.

5.2.5 Signal Detection and Processing

The final step in utilizing a universal detection array for quantitatively recognizing terminal subsequences in a sample of nucleic acids is detecting the hybridization signals that result from hybridization of a UDA according to the previously described methods. This subsection describes preferred laser-based optical detection methods along with certain, primarily chemical, alternative methods.

After a UDA is exposed to a sample of nucleic acids according to the method of hybridization/ligation or of strand-invasion ligation (thereby becoming a "hybridized UDA"), the location in the array and intensity of hybridization of target nucleic acids with probes of the UDA are detected. The location of hybridization determines the terminal subsequences recognized. Correlation of the location of a cell having a hybridization signal with the layout according to which probes were deposited or synthesized on the array determines the sequence of the hybridization region of the probes in that cell, and consequently, the sequence of complementary terminal subsequences of target nucleic acids hybridizing in that cell.

The intensity of the hybridization signal, preferably, determines the quantitative abundance of that target nucleic acid species. First, the amount of hybridized target nucleic acid depends on the original concentration of that target nucleic acid, because as described with respect to the hybridization methods, the array is preferably hybridized in a pseudo-linear region, which is defined by the intensity of the hybridization signal being proportional to the initial concentrations of the nucleic acid species. Therefore, the intensity of the hybridization signal determines relative quantitative abundances of target nucleic acid species, because additionally detection methods preferably generate a hybridization signal that depends on the amount of hybridized target nucleic acid. Optionally, concentration standards of known sequences can be added to the target sample to provide a reference by which absolute abundance of target nucleic acid species can be determined from the relative abundance signals.

Therefore, the preferred optical signal detection methods determine the location and relative quantitative intensity of hybridization signals from an array. In a preferred embodiment, the optical signals are generated from fluorescent moieties which are conjugated to the target nucleic acid species (in direct labeling embodiments) or to the stacking oligomers (in passive labeling embodiments). Typically, a laser of the appropriate emission wavelength stimulates the fluorescent moieties, and the resulting fluorescence is observed by a microscope. The use of two spectrally distinguishable fluorescent dyes is advantageous for the simultaneous observation of two directly labeled samples of target nucleic acids. Using a different dye on each sample, together with hybridization of a UDA with both samples simultaneously, permits direct comparisons of nucleic acid abundance between the two samples. This is useful for differential gene expression observations, genotype analysis, or diagnostic tests, for example where a patient is compared to a control or to the same patient in a previous state.

A UDA is adaptable to most types of fluorescent dyes that can be conjugated to nucleic acids. Succinimidyl esters of carboxy fluoresceins, such as FAM, are preferred. However, the invention is immediately adaptable to such fluorescent dyes as bimane, ethidium, europium (III) citrate, fluorescein, La Jolla blue (Diatron, Miami, Fla.), methyl-coumarin, nitro-benzofuran, pyrene butyrate, rhodamine, terbium chelate, tetramethyl-rhodamine, acridine, psoralen, and aminocoumarin, as well as more specialized fluorescent dyes listed in Table 12 in Section 6.7. (Both absorption and emission maximums are listed for each dye).

Another class of dyes advantageously used in the present invention are fluorescence resonance energy transfer dyes (hereinafter called "FRET" dyes). FRET dye emission results when a donor fluorophore moiety, excited by a light source, transfers its excitation energy to an acceptor fluorophore moiety, which then emits a visible photon. FRET dyes can be detected by emission of the acceptor moiety, or alternatively, by quenching of the donor moiety. The energy transfer is distance-dependent, and its efficiency decreases with increasing distance (dropping off beyond approximately 10–100 angstroms). Since FRET dyes provide fluorescence emission of intensity comparable to or greater than that of other fluorescent dyes, such dyes can be advantageously used in this invention for any fluorescent labeling moiety. See, e.g., Ju et al., 1996, Nuc. Acids Res. 24:1144–1148. Further, since FRET dyes are advantageous for investigating distance dependent effects in nucleic acids, the donor and acceptor moieties can be placed on different oligomers of this invention to indicate that a fluorescence signal comes from correctly configured nucleic acids. See, e.g., Mergny et al., 1996, Nuc. Acids Res. 22:920–928. For example, a donor can be placed on a probe and an acceptor on a stacking oligomer in order to indicate that a fluorescence signal originates only from correctly and specifically hybridized stacking oligomers. Any pair of FRET dyes suitable to conjugation of oligomers can be adapted to this invention. Many non-FRET dyes can be used in a FRET mode. For example, FAM can act as a donor for such acceptor dyes as FAM, JOE, TAMRA, and ROX. Exemplary FRET dyes are listed in Table 13 in Section 6.7.

Preferably, emission from fluorescent dye labels on a hybridized UDA is stimulated by scanning the UDA with a laser having a wavelength and intensity chosen in view of the properties of the fluorescent dye(s) chosen. In an exemplary embodiment, an argon-krypton laser together with filters for emission at 488, 568, or 647 nm can be used. The filter at 488 nm is employed to detect the preferred fluorophore FAM, which has an absorption maximum at 492 nm and emission maximum at 515 nm (at a pH of approximately 9.0). Alternatively, ROX, with an absorption maximum at 568 nm, or Cy5, with an absorption maximum at 675 nm can be used. Alternatively, an ultraviolet excitation line from a mercury arc lamp with emission at 364 nm can be used together with such fluorescent dyes as acridine, psoralen, or aminocoumarin. Laser intensity is preferably not such that excessive scattered laser light is detected. Optionally, narrow-band rejection filters can be used. UDA conditions during laser scanning are optimized for the particular dyes used.

Fluorescent signals generated from the hybridized UDA are detected using a microscope, preferably a confocal microscope. An exemplary embodiment uses a Zeiss model LSM 410 confocal microscope (Carl Zeiss Inc., Thornwood, N.Y.), an argon-krypton laser and appropriate emission filters, and a means for recording an image of emission stimulated from a UDA. Image recording can be provided by a transmitted light camera, such as e.g., a Zeiss Axiovert 135, Carl Zeiss Inc., or image-recording electronics, including charge-coupled device (CCD) cameras (Akhavan-Tafti et al., 1994, J. Biolumin. Chemilumin. 9:155–164), cooled CCD cameras (Martin et al., 1994, J. Biolumin. Chemilumin. 9:145–153), image intensifiers coupled to CCD cameras, or a photo-multiplier tube coupled with mechanical raster scanning (Pease et al., 1994, Proc. Natl. Acad. Sci. USA 91(11):5022–5026). Additionally, the same Zeiss LSM 410 system can be used for simultaneous collection of signals from two spectrally distinguishable fluorescence dyes. Spectral information generated in the form of emitted photons is captured, preferably in a linear range, by photo-multiplier tubes (PMT), one PMT being optimized to collect information from each of the excited dyes. The collected information is stored and transferred electronically in the form of images of an appropriate the file format. Alternatively, a Biorad MRC 600 confocal microscope mounted on a Zeiss Axio-skop and equipped with a motorized focus attachment together with an argon laser and appropriate emission filter can be used for detection of signals stimulated from a UDA.

The final detection step involves processing the observed images in order to extract quantitative hybridization information from each cell of the images of the hybridized UDA. Such processing is advantageously performed with computer-implemented image processing software. Film or slide images of the hybridized UDA can be scanned into an image file using readily available computer scanners, such as Alps MD-4000 (Alps Electric, San Jose, Calif.). Images directly captured electronically can be made available in an image file format by the electronic camera software. Preferred image file formats include the RAW, TIFF, PICT, or BMP formats. In an optional first processing step, images are standardized into a specified file format, such as TIFF using the Adobe Photoshop 4.0 program (Adobe Systems Incorporated, San Jose, Calif.), or an equivalent image processing program.

In a second processing step, hybridization signals are quantitated from the images by a program capable of normalizing and measuring image characteristics. In particular, integrated signal intensities are individually determined from all cell of the UDA. In view of the preceding method steps, these integrated intensities are preferably substantially proportional to the initial concentrations of the target nucleic acid species. Thereby, the integrated intensity from and the location of the cells allow determination of the relative initial concentrations of the target nucleic acid species as determined by their recognized terminal subsequences.

Preferable facilities for a program adaptable to this second step include image adjustment features such as contrast enhancement, density profiling, smoothing, sharpening, edge detection, median filtering, spatial convolution with user defined kernels, and so forth, image measurement features such as finding image feature area, mean, centroid, perimeter, density, integrated density, and so forth, and calibration capability for size and density. A preferred program for this second step is ImagePC, available from the National Institutes of Health (Bethesda, Md.). In particular detailed information about ImagePC and its applications is available by anonymous FTP from the directory /pub/nih-image/documents at the Internet address zippy.nimh.nih.gov. Preferably, image processing programs have the capability for spectrally resolving colors which have been stored in independent or pseudo-independent color planes recorded from emissions of separate fluorescent dyes. Such color processing abilities include implementations for passing the collimated fluorescence collected from a cell through a multi-element bandpass filter for selection of discrete wavelength regions from the emitted fluorescence (Kostichka et al., 1992, Bio/Technology 10:78–81). The light then passes through a wedge prism, whereby each of the wavelength regions is diverted angularly to a different direction. This diverted light is collected by another camera lens, that produces a single image on the CCD for each of the wavelength regions selected.

Further, the invention is adaptable to the use of other reporter moieties for optical signal generation, such as biotin, digoxigenin, chemiluminescent assay, metal ions, and so forth. These methods are preferred in the case where the UDA is arrayed on other than a planar surface, such as, for example, by being configured in the wells of a microtiter plate. Detection methods for biotin or digoxigenin offer the advantages of amplification of the hybridization signal, and are preferred for the detection of rare species of targets in the subsample. Biotin can be detected by complexing with avidin or streptavidin that is coupled preferably to a fluorescent tag, such as fluorescein isothiocyanate (FITC) or by complexing with enzymes such as horse radish peroxidase or alkaline phosphatase. Such enzymes are visualized by in situ enzymatic assays known in the art. See, e.g., Sambrook et al., *Molecular Cloning B A Laboratory Manual,* Cold Spring Harbor Press, New York (1989). Digoxigenin can be detected by reaction with a suitable antibody that is coupled either to FITC or by conjugation to an enzyme, such as horse radish peroxidase or alkaline phosphatase as just described for biotin. Chemiluminescent labels are attached by incorporation during synthesis and are assayed by enzymatic detection. Metal ions are detected using a wave guide (Stimpson et al., 1995, Proc. Natl. Acad. Sci. USA 92:6379–6383).

6 EXAMPLES

The invention is further described in the following examples which are in no way intended to limit the scope of the invention.

6.1 Preparation of Subsamples

The section sets forth exemplary protocols for preparing subsamples of nucleic acid fragments from an initial sample of nucleic acids such that all fragments in each subsample have selected primary subsequences. Since for many applications of this invention the initial sample of nucleic acids includes cDNAs, the first subsection set forth an exemplary protocol for the synthesis of cDNA from RNA. The second subsection describes preparing fragment subsamples from an initial sample.

6.1.1 cDNA Synthesis

Numerous protocols for mRNA isolation from tissues are widely known in the art, and any such appropriate protocol can be used to prepare an mRNA sample from tissue samples of interest. Similarly, numerous protocols are widely known for the synthesis of cDNA from mRNA. In particular, a preferred protocol for synthesis of de-phosphorylated cDNA starting from 200 ng poly (A)+ RNA is described herein. First, the reagents used in the protocol are listed; second, the protocol steps are listed.

Reagents Used:
1) Random hexamers (50 ng/$\mu$l)
2) 5×First strand buffer (BRL)
3) 10 mM dNTP mix
4) 100 mM DTT
5) SuperScript II reverse transcriptase (BRL) (200 U/$\mu$l)
6) *E. coli* DNA ligase (BRL) 10 U/$\mu$l
7) *E. coli* DNA polymerase (BRL) 10 U/$\mu$l
8) T4 DNA polymerase 2.5 U/$\mu$l
9) *E. coli* RNaseH (BRL) 3.5 U/$\mu$l
10) Arctic Shrimp Alkaline Phosphatase, (SAP; USB), and 10×SAP buffer (USB)
11) 5×Second strand buffer (BRL)
12) 3 M Na-Acetate
13) Phenol:Chloroform (phenol:chloroform:isoamyl alcohol 25:24:1)
14) Chloroform isoamyl alcohol (24:1)
15) Absolute and 75% ethanol
16) 20 $\mu$g/$\mu$l glycogen (Boehringer Mannheim)

cDNA Synthesis Protocol:
1. Mix 0.25–1.0 $\mu$g of poly A+ RNA with 50 ng of random hexamers in 10 $\mu$l of water. Heat the mixture to 70° C. for 10 min. and quick chill in ice-water slurry. Keep on ice for 1–2 min. Spin in microfuge for 10 secs. to collect condensate.

2. Prepare first stand reaction mix with 4 μl 5×First strand buffer, 2 μl 100 mM DTT, 1 μl 10 mM dNTP mix, and 2 μl water. Add this mix to the primer-annealed RNA from step 1. Place mixture at 37° C. for 2 mins. Add 1 μl of Superscript II (BRL) (following manufacturer's recommendations). Incubate at 37° C. for 1 hr.
3. Place tubes on ice, add 30 μl of 5×Second strand buffer, 90 μl of cold water, 3 μl of 10 mM dNTP, 1 μL (10 units) of *E. coli* DNA ligase, 4 μl (40 units) of *E. coli* DNA polymerase, and 1 μl (3.5 units) of *E. coli* RnaseH. Incubate for 2 h. at 16° C.
4. Add 2 μl of T4 DNA polymerase (5 units) and incubate at 16° C. for 5 min.
5. Add 20 μl 10×SAP buffer, 25 μl of water, and 5 μl (5 units) of SAP. Incubate at 37° C. for 30 min.
6. Extract cDNA with phenol-chloroform, chloroform-isoamyl alcohol. To the aqueous layer add Na-acetate to 0.3 M, 20 μg glycogen, and 2 vol of ethanol. Incubate at −20° C. for 10 min., spin at 14,000 g for 10 min. Wash pellet with 75% ethanol. Dissolve pellet in 50 μl TE.
7. Estimate the yield of cDNA using fluorometer.
8. For subsequent processing, transfer 75 ng cDNA to a separate tube, add TE to make the concentration 600 ng/ml and put that tube in the specified box at −20° C. For storage, add Na-acetate to 0.3 M and 2 vol of ethanol to the rest of cDNA and store at −80° C.

Alternative primers known in the art can also be used for first strand synthesis. Such primers include oligo(dT) primers, phasing primers, gene-specific primers, etc.

6.1.2 Subsample Preparation

Subsamples can be prepared from original samples of cDNA or other nucleic acids according to the following preferred protocol. Preferably, protocols for subsample preparation enhance reproducibility and specificity by reducing or eliminating such individual manipulations as buffer changes, precipitations, or organic (phenol/chloroform) extractions.

Initially, a sample of de-phosphorylated cDNA (or other nucleic acid sample) is separated into batches of from 1 ng to at least 50 ng cDNA each. The number of batches is at least equal to the number of fragment subsamples (each deriving from original nucleic acids having different, specified primary subsequences) necessary for the desired degree of coverage. Advantageously, subsample preparation can be duplicated or triplicated for increased confidence, in which case additional batches are needed.

According to the preferred protocol, primary subsequences are recognized as the recognition sites of Type II REs, and RE digestion proceeds simultaneously with adapter ligation. An amount of RE enzyme is specified in the protocols that is sufficient for complete digestion while minimizing other enzymatic exo- or endo-nuclease activity. Preferred and alternate RE combinations can be found in Tables 11 to 14 of PCT Publication WO 97/15690.

Adapters are chosen that are uniquely capable of hybridizing with the single-stranded terminal subsequences ("RE overhang") generated by each RE in a subsample preparation reaction. Adapters are composed of a hybridized linker and primer strands. The linker strand is complementary to one unique RE overhang in a reaction, and the primer strand is at least partially complementary to one linker strand in a reaction. Where a Type IIS restriction endonuclease enzyme participates in recognizing the additional subsequence, one primer has an appropriately placed Type IIS RE recognition site and a label moiety. In this case, the other primer in a subsample reaction has a conjugated capture moiety, such as, e.g., biotin, to provide for purification of Type IIS digested fragments for subsequence UDA hybridization. Exemplary fluorescent label moieties are listed Section 6.11.

In the general case, possible primer, linker, and Type II RE combinations are listed in Table 4 of Section 6.1.3. In the preferred case where additional subsequence recognition depends on digestion by a Type IIS RE, preferred primer-linker combinations are slightly modified from those of Table 4. Exemplary primer-linker combinations are described in Table 7 of Section 6.2.

The preferred protocol for subsample preparation proceeds by first, hybridizing primers and linkers to form adapters, by second, digesting and ligating a batch of the initial sample, and by third, PCR amplifying the digestion/ligation produces.

Primer-excess Adapter Hybridization

Primers and linkers are chosen as described above for the particular Type II REs used to recognized the primary subsequences. Next, linkers and excess primers are hybridized according to the following protocol in order to produce an "adapter set," including sufficient adapters, that is hybridized primers and linkers, for the RE/ligase reaction and also sufficient excess primers for the subsequent PCR amplification. Accordingly, primers do not have to be separately added to the PCR reaction mix.

1. Add to water linker and primer in a 1:20 concentration ratio (12-mer:24-mer) with the primer at a total concentration of 50 pm per μl.
2. Incubate at 50° C. for 10 minutes.
3. Cool slowly to room temperature and store at −20° C.

RE/Ligase & PCR Amplification Protocol

This protocol performs in a single vessel both the RE digestion and ligation reactions and the PCR reactions. Solutions and buffers for both reactions, the PCR solution being termed the "QPCR mix" and the RE/ligation solution being termed the "Qlig mix," are prepared and placed in a single reaction tube separated by a wax layer.

1. Combine the following components for the QPCR mix as shown:

| Reagent | Concentration | 1 rxn | 96 rxns |
| --- | --- | --- | --- |
| 10 × TB 2.0 | 500 mM Tris pH 9.15, 160 mM (NH$_4$)$_2$SO$_4$, 20 mM MgCl$_2$ | 5 μl | 525 μl |
| dNTP (equimolar mixture) | 10 mM | 2 μl | 210 μl |
| Klentaq:PFU (16:1) | 25 U/ml | 0.25 μl | 26.25 μl |
| water | | 32.75 μl | 3438.75 μl |
| wax | 90:10 Paraffin:Chillout ™ 14 | | |

2. Pre-wax PCR tubes by melting the 90:10 Paraffin:Chillout™ 14 wax and adding the melted wax to the tubes in such a way that the wax solidifies on the sides of the upper half of the tubes.
3. Mix solutions by tapping and/or inverting the tubes (do not vortex). Add 40 µl QPCR mix to the pre-waxed PCR tubes. Add the solution one tube at a time carefully avoiding the sides and wax in the tubes. Note that it is important to keep the QPCR and the Qlig mixes separate as any QPCR mix in the ligation and the reaction will not work.
4. The tubes are placed in a thermal cycler without lids and the wax is melted onto the liquid layer by incubating at 75° C. for 2 min, followed by decreasing increments of 5° C. for every 2 min until 25° C. is reached.
5. Combine the following components for the Qlig mix as shown:

| Regent | Concentration | 1 rxn | 24 rxn |
|---|---|---|---|
| RE 1 | depends on RE | 0.2 µl | 5.2 µl |
| RE 2 | depends on RE | 0.2 µl | 5.2 µl |
| Adapter set 1 | 20 pmole/ml for primer | 1 µl | 26 µl |
| Adapter set 2 | 20 pmole/ml for primer | 1 µl | 26 µl |
| ATP | 10 mM | 0.8 µl | 20.8 µl |
| NEB 2 | 10 X | 1 µl | 26 µl |
| Betaine | 5M | 2 µl | 52 µl |
| Ligase | 1 U/ml | 0.2 µl | 5.2 µl |
| H$_2$O | | 2.6 µl | 67.6 µl |

6. After the Qlig mixes are complete for each set of enzymes the mix can be split up into tubes before adding the cDNAs. 24 reactions can be split up into 8 tubes each with 3 reaction volumes (approximately 27 µl).
7. Add the cDNA to the tubes and mix:

| Reagent | Concentration | 1 rxn | 3 rxns |
|---|---|---|---|
| cDNA sample | 1 ng/µl | 1 µl | 3 µl |

The cDNA is pre-diluted to the appropriate concentration of 1 ng/µl.
8. Add 10 µl of the Qlig mix to the top of the wax being careful not to disturb the wax. In the case where 24 Qlig reactions are triplicated, the products can be split into 24 individual QPCR reactions.
9. Gently add the caps to the tubes. Excess pressure can disturb the wax.
10. Place the tubes in a thermal cycler and perform the following thermal protocol.

| Temp (in ° C.) | Time (in min.) | Reaction |
|---|---|---|
| 37 | 30 | Optimal RB digestion temperature |
| Ramp down to 37° C. at −1° C./min. | | |
| 16 | 60 | Optimal ligation temperature |
| 37 | 15 | Optimal RB digestion temperature |
| 72 | 20 | Melt wax; mix solutions in tube; blunt-end chains |

| Temp (in ° C.) | Time (in min.) | Reaction |
|---|---|---|
| Cycle the following steps for the number of PCR cycles, preferably 20 | | |
| 96 | 30 sec. | Denaturing |
| 57 | 1 | Hybridizing |
| 72 | 2 | Chain elongation |
| End of the PCR cycles | | |
| 72 | 10 | |
| 4 | hold | |

11. After program is finished heat the tubes to 75° C. for 5 minutes. Pull out the tubes and immediately turn them upside down till the wax hardens.
12. Place finished reactions in freezer or proceed directly to further processing.

The following are the preferred vendors for the various reagents used in this protocol.

| Reagents | Vendor | Catalog # |
|---|---|---|
| Enzymes | NEB (Beverly, MA) | |
| Adapters | Amitof/NBI (Allston, MA) | (see Table 4 for sequences) |
| Fluorescent Primers | Genosys (The Woodlands, TX) | (see Table 4 for sequences) |
| ATP | Pharmacia (Newark, NJ)) | 27-1006-02 |
| dNTP | Pharmacia | 27-2035-02 |
| Klentaq | Ab peptides (St. Louis, MO) | 1001 |
| PFU | Stratagene (Los Angeles, CA) | 600154 |
| Betaine | Sigma (St. Louis, MO) | B-2754 |
| Paraffin wax | Fluka Chemical, Inc. (Ronkonkoma, N.Y.) | 76243 |
| Chillout ™ 14 liquid wax | MJ Research | |
| Ligase | BRL (Baltimore, MD) | 15224-025 |

Additional protocols for subsample generation are known in the art. See, e.g., Section 6 of PCT Publication PCT/US96/17159, which is hereby incorporated by reference in its entirety. In particular, this latter reference sets forth protocols in which the RE digestion and adapter ligation are performed sequentially, instead of simultaneously. Further, this latter reference describes testing results from applying these protocols with various adapters and Type II RE pairs.

6.1.3 Preferred Adapters

Table 4 lists preferred primer-linker pairs that may be used to form adapters for subsample preparation reactions. The primers-linkers listed are adaptable to possible combinations of approximately 56 available REs generating a 5'4 bp overhang. There are at least 40 such REs available from New England Biolabs. For a subsample preparation reaction, one primer and one linker from the "R" series corresponding to one of the pair of REs and one primer and one linker from the "J" series corresponding to the other of the pair of REs are used together. Two pairs from the same series are not compatible during amplification. Conjugated at the 5'-end of the adapters is a biotin capture moiety or a fluorescent label moiety as needed for the subsequence determination of the available subsequences.

TABLE 4

SAMPLE ADAPTERS

Adapter: Primer (longer strand)
Linker (shorter strand)
Series Notes: 'm' signifies an optional label or capture moiety.    RE

| Series | Sequence | RE |
|---|---|---|
| RA24 | 5'm-AGC ACT CTC CAG CCT CTC ACC GAA 3' (SEQ ID NO:1) | |
| RA1 | 3' AG TGG CTT TTAA (SEQ ID NO:2) | Tsp509I<br>Mfe1<br>EcoRI |
| RA5 | 3' AG TGG CTT GTAC (SEQ ID NO:3) | NcoI<br>BspHI |
| RA6 | 3' AG TGG CTT GGCC (SEQ ID NO:4) | XmaI<br>NgoMI<br>BspEI |
| RA7 | 3' AG TGG CTT GCGC (SEQ ID NO:5) | BssHII<br>AscI |
| RA8 | 3' AG TGG CTT GATC (SEQ ID NO:6) | AvrII<br>NheI<br>XbaI |
| RA9 | 3' AG TGG CTT CTAG (SEQ ID NO:7) | DpnII<br>BamHI<br>BclI |
| RA10 | 3' AG TGG CTT CGCG (SEQ ID NO:8) | KasI |
| RA11 | 3' AG TGG CTT CCGG (SEQ ID NO:9) | EagI<br>Bsp120I<br>NotI EaeI |
| RA12 | 3' AG TGG CTT CATG (SEQ ID NO:10) | BsiWI<br>Acc65I<br>BsrGI |
| RA14 | 3' AG TGG CTT AGCT (SEQ ID NO:11) | XhoI<br>SalI |
| RA15 | 3' AG TGG CTT ACGT (SEQ ID NO:12) | ApaLI |
| RA16 | 3' AG TGG CTT AATT (SEQ ID NO:13) | AflII |
| RA17 | 3' AG TGG CTT AGCA (SEQ ID NO:14) | BssSI |
| RC24 | 5' m-AGC ACT CTC CAG CCT CTC ACC GAC 3' (SEQ ID NO:15) | |
| RC1 | 3' AG TCG CTG TTAA (SEQ ID NO:16) | Tsp509I<br>EcoRI<br>ApoI |
| RC3 | 3' AG TCG CTG TCGA (SEQ ID NO:17) | HindIII |
| RC5 | 3' AG TCG CTG GTAC (SEQ ID NO:18) | BspHI |
| RC6 | 3' AG TCG CTG GGCC (SEQ ID NO:19) | AgeI<br>NgoMI<br>BspEI<br>SgrAI<br>BsrFI<br>BsaWI |
| RC7 | 3' AG TCG CTG GCGC (SEQ ID NO:20) | MluI<br>BssHII<br>AscI |
| RC8 | 3' AG TCG CTG GATC (SEQ ID NO:21) | SpeI<br>NheI<br>XbaI |
| RC9 | 3' AG TCG CTG CTAG (SEQ ID NO:22) | DpnII<br>BglII<br>BamHI<br>BclI<br>BstYJ |
| RC10 | 3' AG TCG CTG CGCG (SEQ ID NO:23) | KasI |
| RC11 | 3' AG TCG CTG CCGG (SEQ ID NO:24) | Bsp120I<br>NotI |
| RC12 | 3' AG TCG CTG CATG (SEQ ID NO:25) | Acc56I<br>BsrGI |
| RC14 | 3' AG TCG CTG AGCT (SEQ ID NO:26) | SalI |
| RC15 | 3' AG TCG CTG ACGT (SEQ ID NO:27) | Ppu10I<br>ApaLI |
| JA24 | 5' m-ACC GAC GTC GAC TAT CCA TGA AGA 3' (SEQ ID NO:28) | |
| JA1 | 3' GT ACT TCT TTAA (SEQ ID NO:29) | Tsp509I<br>Mfe1<br>EcoRI |
| JA5 | 3' GT ACT TCT GTAC (SEQ ID NO:30) | NcoI<br>BspHI |

TABLE 4-continued

SAMPLE ADAPTERS

Adapter: Primer (longer strand)
Linker (shorter strand)

| | | |
|---|---|---|
| JA6 | 3' GT ACT TCT GGCC (SEQ ID NO:31) | XmaI |
| | | NgoMI |
| | | BspEI |
| JA7 | 3' GT ACT TCT GCGC (SEQ ID NO:32) | BssHII |
| | | AscI |
| JA8 | 3' GT ACT TCT GATC (SEQ ID NO:33) | AvrII |
| | | NheI |
| | | XbaI |
| JA9 | 3' GT ACT TCT CTAG (SEQ ID NO:34) | DpnII |
| | | BamHI |
| | | BclI |
| JA10 | 3' GT ACT TCT CGCG (SEQ ID NO:35) | KasI |
| JA11 | 3' GT ACT TCT CCGG (SEQ ID NO:36) | EagI |
| | | Bspl201 |
| | | NotI |
| | | EaeI |
| JA12 | 3' GT ACT TCT CATG (SEQ ID NO:37) | BsiWI |
| | | Acc65I |
| | | BsrGI |
| JA14 | 3' GT ACT TCT AGCT (SEQ ID NO:38) | XhoI |
| | | SalI |
| JA15 | 3' GT ACT TCT ACGT (SEQ ID NO:39) | ApaLI |
| JA16 | 3' GT ACT TCT AATT (SEQ ID NO:40) | AflII |
| JA17 | 3' GT ACT TCT AGCA (SEQ ID NO:41) | BssSI |
| JC24 | 5' m-ACC GAC GTC GAC TAT CCA TGA AGC 3' (SEQ ID NO:42) | |
| JC1 | 3' GT ACT TCG TTAA (SEQ ID NO:43) | Tsp509I |
| | | EcoRI |
| | | ApoI |
| JC3 | 3' GT ACT TCG TCGA (SEQ ID NO:44) | HindIII |
| JC5 | 3' GT ACT TCG GTAC (SEQ ID NO:45) | BspHI |
| JC6 | 3' GT ACT TCG GGCC (SEQ ID NO:46) | AgeI |
| | | NgoMI |
| | | BspBI |
| | | SgrAT |
| | | BsrFI |
| | | BsaWI |
| JC7 | 3' GT ACT TCG GCGC (SEQ ID NO:47) | MluI |
| | | BssHII |
| | | AscI |
| JC8 | 3' GT ACT TCG GTAC (SEQ ID NO:48) | SpeI |
| | | NheI |
| | | XbaI |
| JC9 | 3' GT ACT TCG CTAG (SEQ ID NO:49) | DpnII |
| | | BglII |
| | | BamHI |
| | | BclI |
| | | BstYI |
| JC10 | 3' GT ACT TCG CGCG (SEQ ID NO:50) | KasI |
| JC11 | 3' GT ACT TCG CCGG (SEQ ID NO:51) | Bspl20I |
| | | NotI |
| JC12 | 3' GT ACT TCG CATG (SEQ ID NO:52) | Acc56I |
| | | BsrGI |
| JC14 | 3' GT ACT TCG AGCT (SEQ ID NO:53) | SalI |
| JC15 | 3' GT ACT TCG ACGT (SEQ ID NO:54) | Ppul0I |
| | | ApaLI |

Biotin can be conjugated to primers by using standard phosphoramidite chemistry.

6.2 Generation of Terminal Subsequences

When a UDA is used to recognized the additional subsequence, the nucleic acid fragments need a terminal single-stranded subsequence. The preferred protocol for determining the additional subsequence uses Type-IIS restriction enzymes to generate such single-stranded terminal subsequences. The digestion step uses a fluorescently (e.g., FAM) labelled primer having appropriately placed Type-IIS RE recognition sites. This primer is designed so that cleavage of the amplified products with the Type-IIS enzyme leaves a terminal subsequence, including a 5'-end overhang of 4 or 5 nucleotides. One to three nucleotides of the adjacent double-stranded subsequence can also be recognized by a UDA according to the strand-invasion method. The other primer has a conjugated capture moiety (e.g., biotin) to facilitate purifying the fragments for hybridization with a UDA.

Exemplary Type IIs Restriction Enzymes

Table 5 lists exemplary Type IIS REs adaptable to this embodiment of the instant invention along with certain important characteristics. For each RE, the table lists the recognition sequence on each strand of a dsDNA molecule and the distance in bp from that recognition sequence to the location of strand cutting. Also listed is the length of the overhang generated.

TABLE 5

TYPE IIS REs

| Type IIS RE | Recognition Sequence | Dist. to cutting site (bp) | Over-hang (bp) | Comment |
|---|---|---|---|---|
| FokI | 5'-GGATG | 9 | 4 | |
| | CCTAC | 13 | | |
| HgaI | 5'-GACGC | 5 | 5 | |
| | CTGCG | 10 | | |
| BbvI | 5'-GCAGC | 8 | 4 | |
| | CGTCG | 12 | | |
| BsmFI | 5'-GGGAC | 10 | 4 | Lower recognition site specificity |
| | CCCTG | 14 | | |
| BspMI | 5'-ACCTGC | 4 | 4 | |
| | TGGACG | 8 | | |
| SfaNI | 5'-GCATC | 5 | 4 | |
| | CGTAG | 9 | | |
| Bsp24I | 5'-GACNNNNNNNTGG | 12 | 5 | Degtyarev et al., 1993, Gene 131:93–95 |
| | CTGNNNNNNACC | 7 | | |
| BspLU11 III | 5'-GGGAC | 10 | 4 | Chernov, A.V et al., 1995,Nuc. Acids Res 23:1213–1214 |
| | CCCTG | 14 | | |

The additional restriction endonucleases, BcgI, CjeI, and CjePI listed in Table 6 are also adaptable to this invention. Since they have properties unlike the Type II REs listed in Table 5, they are separately listed in Table 6. In particular, these REs cleave double stranded DNA in both direction from the recognition sequences, so that short fragments are released having single-stranded terminal subsequences on both ends.

TABLE 6

ADDITIONAL TYPE IIS REs

| Type IIS RE | Recognition Sequence | Dist. to cutting site (bp) | Over hang (bp) | Dist. to cutting site (bp) | Over hang (bp) | Ref. |
|---|---|---|---|---|---|---|
| CjeI | 5'-ACN$_6$TGG | 14 | 6 | 9 | 6 | 1 |
| | TGN$_6$ACC | 8 | | 15 | | |
| CjePI | 5'-CCAN$_6$TC | 14 | 6 | 9 | 6 | 1 |
| | GGTN$_6$AC | 8 | | 15 | | |
| Beg I | 5'-CGAN6TGC | 12 | 2 | 12 | 2 | 2 |
| | GCTN6ACG | 10 | | 10 | | |

Reference 1: Vitor et al., 1995, Gene 157:109–110; reference 2: New England Biolabs 96/97 Catalog.
Exemplary Primers for Subsample Preparation Reactions The choice of primers and linkers where Type IIS enzymes are used is similar to the previously described general case. Referring to Table 4, each subsample preparation reaction requires one primer/linker combination from the "R" series appropriate for one of the REs used in the reaction and one primer/linker combination from the "J" series appropriate for the other RE used. However, the R-series primer is modified so that a biotin moiety is conjugated at or near the 5'-end. Importantly, the J-series primer is modified to have an appropriate Type IIS recognition site at an appropriate location. The corresponding linker must be similarly modified to be complementary any overlapping modification to the primer.

Table 7 lists exemplary J-series primers having Type IIS RE recognition sites adaptable to the subsample preparation reactions previously described. They satisfy the requirements on primers previously described in Section 5.1, and are all designed for subsample preparation reactions using Type II REs producing 4 bp single-stranded overhangs. Exemplary linkers and associated Type II REs and included for the primers. In view of these tables, modification of the additional linkers listed in Table 4 to these, and to other primers with recognition sites for different Type IIS enzymes, will be apparent to one of average skill.

TABLE 7

SAMPLE PRIMERS

| Ser. | Primer or Linker Note: 'f 'signifies a FAM label moiety | RE (ds/ss) |
|---|---|---|
| JA24-K | 5' f-ACC GAC GTC GAC TAT GGA TGA AGA (SEQ ID NO:56) | FokI (0/4) |
| JA5-K | 3' CT ACT TCT GTAC (SEQ ID NO:57) | NcoI BspHI |
| JA6-K | 3' CT ACT TCT GGCC (SEQ ID NO:58) | AgeI NgoMI BspEI SgrAI BsrFI BsaWI |

TABLE 7-continued

SAMPLE PRIMERS

| Ser. | Primer or Linker<br>Note: 'f 'signifies a FAM label moiety | RE<br>(ds/ss) |
|---|---|---|
| JA9-K | 3' CT ACT TCT CTAG (SEQ ID NO:59) | DpnII BglII<br>BamHI BclI<br>BstYI |
| JA24-K2 | 5' f-ACC GAC GTC GAC TAT CGG ATG AGA (SEQ ID NO:60) | FokI<br>(1/4) |
| JA5-K2 | 3' CC TAC TCT GTAC (SEQ ID NO:61) | NcoI<br>BspHI |
| JA24-K3 | 5' f-ACC GAC GTC GAC TAT CCG GAT GGA (SEQ ID NO:62) | FokI<br>(2/4) |
| JA5-K3 | 3' GC CTA CCT GTAC (SEQ ID NO:63) | NcoI<br>BspHI |
| JA24-K4 | 5' f-ACC GAC GTC GAC TAT CCA GGA TGA (SEQ ID NO:64) | FokI<br>(3/4) |
| JA5-K4 | 3' GT CCT ACT GTAC (SEQ ID NO:65) | NcoI<br>BspHI |
| JA24-B | 5' f-ACC GAC GTC GAC TAT CGC AGC AGA (SEQ ID NO:66) | BbvI<br>(0/4) |
| BA9 | 3' CG TCG TCT CTAG (SEQ ID NO:67) | DpnII BglII<br>BamHI BclI<br>BstYI |
| BA5 | 3' CG TCG TCT GTAC (SEQ ID NO:68) | NcoJ<br>BspHI |
| JC24-H | 5' f-ACC GAC GTC GAC TAT CCA TGA CGC (SEQ ID NO:69) | HgaI<br>(0/5) |
| JC5-H | 3' GT ACT GCG GTAC (SEQ ID NO:70) | BspHI |

The "Ser." lists the series identification of the primer or linker, with the modification indicated after the "-." The "Primer or Linker" column lists the sequences of the primers and linkers. The Type IIS sites are indicated by bold and underlining; consequence modifications to the linkers are indicated by underlining. The "RE (ds/ss)" column lists either: (i) the Type IIS RE the primer and following linkers are adapted to (in the subsequence Type IIS digestion reaction), (ii) the Type II REs the linkers are adapted to (in the initial subsample preparation reactions), or (iii) the lengths of the components of the terminal subsequence to be recognized by a UDA. "ss" is the length of the terminal single-stranded region, and "ds" is the length of the adjacent double-stranded region. JA24-K has an internal FokI recognition site as indicated and a 5' FAM label moiety. In primers JA24-K2, -K3, and -K4, the FokI sites are sequentially displaced by 1 bp toward the 3'-end in order to produce longer double-stranded regions. Characteristics of the target produced for each of the alternate placements of FokI site is depicted. JA24-B has an internal BbvI recognition site and a 5' FAM label. JC24-H has an internal HgaI recognition site and a 5' FAM label.

Protocols for Type IIS Digestion and Fragment Purification

After the subsample preparation reactions, nucleic acid fragments are first bound to immobilized binding partners for the capture moieties conjugated to the nucleic acid fragments by virtue of the use of primers with such capture moieties. It is preferred that the capture moiety by biotin and that the immobilized binding partner by streptavidin-coated magnetic beads. Next, the bound fragments are digested with a Type IIS Restriction enzyme, which releases the fragments with single-stranded terminal subsequence ready for sequence analysis, by, e.g., hybridization to a UDA.

Protocol for Purification with Streptavidin-coated Beads

1) Prepare streptavidin coated magnetic beads (Dynal Inc., Lake Success, N.Y.) by diluting 5 μl beads in 200 μl of binding buffer (5 M NaCl, TE).
2) Separate the beads and solution on magnet and discard buffer. Repeat washing 2 more times.
3) Re-suspend the beads in 3 original volumes (15 μl) binding buffer.
4) Mix the 15 μl prepared beads with each 50 nanogram nucleic fragment sample. Nucleic acids binds on the streptavidin-coated magnetic beads by virtue of the biotin moiety at one end.
5) Allow to bind for 30 minutes at 25° C.
6) Separate on magnet and remove buffer.
7) Re-suspend in 100 μl TE. Separate on magnet and discard TE. The 50 nanogram fragment subsample is bound on beads and ready for digestion.

Protocol for Type IIS RE Digestion

1) Re-suspend the bead-bound fragments sample in a total of 50 μl solution containing the appropriate 1×restriction buffer (according to manufacturer's recommendations) and 0.5 Units of the appropriate Type-IIS restriction enzyme. (New England Biolabs)
2) Incubate at 37° C. for 30 minutes.
3) Separate the beads and solution on magnet and collect supernatant containing the digested fragments.
4) Purify the digested fragments by ethanol precipitation. Add sodium acetate solution to a final concentration of 0.3 M, 20 μg glycogen, and 100 μl of ethanol. Incubate at −20° C. for 1 hr, spin at 14,000 g for 10 min. Wash pellet with 75% ethanol. Dissolve pellet in 10 μl of 1×ligase buffer.

6.3 Fragment Confirmation by Phasing PCR

This section sets forth an exemplary protocol for the steps of confirmation and/or fragment isolation based on the additional subsequence information determined by, e.g., UDA hybridization. A phasing PCR primer, designed using the additional subsequence information according to the methods of Section 5.3, in combination with the biotin-conjugated adapter primer, which was previously used in the subsample preparation step, is employed for PCR using the fragment sample generated from Type IIS digestion as described in section 6.2.

For example, the specific sequence of an exemplary phasing primer (KAP-502) appropriate for a subsample generated with primer JA24-K (see Table 7) and for confirming an additional subsequence TGGT has the sequence;

5' f-<u>ACC GAC GTC</u> GAC TAT GGA TGA AGA TGG T (SEQ ID NO:71)

This primer is used in combination with a biotin-conjugated "R" series primer for confirmatory PCR.

An exemplary protocol for the PCR steps are described below.

1) Prepare a 50 µl PCR reaction mix consisting of:
   1×TB 2.0 buffer (500 mM Tris pH 9.15, 160 mM $(NH_4)_2SO_4$, 20 mM $MgCl_2$)
   1 µl NEB buffer 2, (New England Biolabs, Beverly, Mass.)
   800 µM ATP,
   1 M Betaine (Sigma, St. Louis, Mo.)
   500 µM dNTPs,
   1 µl of RA24 (with conjugated biotin) or RC24 (with conjugated biotin) (10 pmol)
   1 µl of Phasing primer (10 pmol)
   1 µl of DNA template from subsample mixture
   0.25 µl Klentaq/pfu mix per reaction
2) Amplify in thermal cycler, e.g., PTC 100 (MJ Research, Watertown, Mass.) based on MQ-8 profile:
   1) 72° C. 20 minutes
   2) 96° C. 30 seconds
   3) 57° C. 1 minute
   4) 72° C. 2 minutes
   5) GOTO step 2 10 more times
   6) 72° C. 10 minutes
   7) 4° C.
3) Analyze PCR products
   1) Electrophoresis PCR products on a 1% agarose gel in TAE buffer alongside DNA size markers.
   2) Stain gel with ethidium bromide and photograph under UV.
   3) Calculate the length of the PCR product(s) by comparison with that of the size markers.

6.4 Preparation of a UDA on a Glass Surface

Preparation of a UDA on a planar glass surface involves the steps of derivitizing the glass surface, designing and preparing probes, and depositing the probes on the surface. Exemplary protocols for theses steps are presented in this subsection.

Derivitizing a Glass Surface

The protocols set forth herein describe preferred methods for preparing surfaces suitable for anchoring probe oligomers. The protocols described produce preferred glass surfaces derivitized with covalently bound isothiocyanate groups.

1) Glass slides of 25×75×1 mm (Catalog # 12-552, Fisher Scientific, Pittsburgh, Pa.) were prewashed according to the following protocol.
   a) Slides were placed in a rack and washed with 5–6 changes of distilled water.
   b) Then they were soaked in 1 M NaOH for 4 hrs at room temperature, and rinsed with several changes of distilled water until the pH of the wash was close to 7.0.
   c) Slides were then soaked for 4 hrs to overnight in fuming nitric acid and rinsed again with dH2O until pH of the wash was 7.0.
   d) Slides were then air dried and stored in a vacuum desiccator.
2) The prewashed slides were used for surface modification according to the following steps
   a) Slides were immersed in 1% 3-aminopropyl- trimethoxysilane (Aldrich Chemicals, Milwaukee, Wis.) solution in 95% acetone in water for 2 min.
   b) They were immediately transferred to ajar containing acetone, and washed with 10 changes of 5 min. each.
   c) The slides were then dried for 45 min in an oven set at 110° C.
   d) Slides were next immersed in 0.2% 1,4-phenylene diisothiocyanate ("PDC") solution (Sigma-Aldrich Chemicals, Milwaukee, Wis.) in 10% pyridine/ dimethyl formamide for 2 hr with occasional stirring.
   e) The slides were washed with 3 changes of methanol followed by 3 changes of acetone for 10 min. each.
   f) Slides were air dried and stored in a vacuum desiccator.

Designing and Preparing Probes

Probes were designed according to Section 5.2.1. In the actual examples described below, the following different probes were used.

MP1: 5'-GACA <u>TCC ATA GTC GAC GTC GGT</u>$(T)_5$-$C_{12}$-amino (SEQ ID NO:72)

MP2: 5'-GACA <u>TCC ATA GTC GAC GTC GGT</u>$(T)_{15}$-$C_{12}$-amino (SEQ ID NO:73)

MP3; 5'-GACA <u>TCC ATA GTC GAC GTC GGT</u>-$C_{12}$-amino (SEQ ID NO:74)

AnGn1:5'-GGTA <u>CTG TGC TAT CCG AGG GAA</u>$(T)_5$-$C_{12}$-amino (SEQ ID NO:75)

Additionally, a set of marker probes labeled with FAM were also used for verification and array alignment.

FAM-MP1: 5'-FAM-GACA <u>TCC ATA GTC GAC GTC GGT</u>$(T)_5$-$C_{12}$-amino

FAM-MP2: 5'-FAM-GACA <u>TCC ATA GTC GAC GTC GGT</u>$(T)_{15}$-$C_{12}$-amino

FAM-MP3; 5'-FAM-GACA <u>TCC ATA GTC GAC GTC GGT</u>-$C_{12}$-amino

Here, the hybridization region is the 5'-terminal four nucleotide subsequence. The core region is underlined. The spacer region is either absent, $(T)_5$, or $(T)_{15}$. The linker is $C_{12}$ with an amino functional group.

Probes were synthesized by and purchased from Biosynthesis, Inc., (Lewisville, Tex.) according to the standard synthetic (e.g., phosphoramidite) protocols. The linker with the amino group were introduced at appropriate steps during synthesis according to the manufacturer's protocol (using the reagent N-trifluoroacetyl-6-aminohexyl-2-cyanoethyl N',N'-diisopropyl-phosphoramidite). After synthesis, the probes were purified by polyacrylamide gel electrophoresis, and their concentrations were determined by UV spectrophotometry at 260 nm.

Before deposition, probes were dissolved in 0.1 M sodium carbonate buffer (pH 9.0) at concentrations of 2 µM to 20 mM and arranged in standard 384 well plates.

Depositing the Probes on the Glass Surface

Manual and robotic methods were used to transfer the probe solutions onto the derivitized glass surface. Manual transfer, used preferably when the total array size was small (less than 20–25 cells total) such as for a test grid, was done by touching the surface of the slide either with blunt-ended needle tips or with pipette tips that had been dipped in the appropriate solution of the appropriate probes. A slide to be arrayed was placed on a paper template containing a grid that served as a guide for locating the position of cells. For identification of the coordinates of each cell in the array, additional alignment marker cells were deposited (in both the manual and robotic methods) with the FAM-labeled probes at controlled positions in and around the array.

Robotic methods were used for arrays of greater complexity, such as 256-arrays or higher. These methods used robot means including an X-Y-Z table and a moveable print head. A custom made such robot, obtained from T-Tech, Inc. (Atlanta, Ga.), contained a platform that could move in X and Y directions and a printing head that could move in X, Y, and Z directions, both device capable of micrometer precision. The platform had four work stations: a 384 well sample plate containing probe solutions and marker probe solutions, a washing station with a deionized water reservoir for washing the depositing needles (alternately pins can be used), a drying station with paper tissues to dry the washed needles by physical contact, and a work area that could accommodate up to nine glass slides in a single deposition operation. The printing head consisted of up to 4 depositing needles, 30 gauge size ½ in. large with luer hub, Cat. #NE-301PL, Small Parts, Inc. (Miami Lakes, Fla.), and is adaptable to accommodate more needles. In the examples reported herein, arrays were deposited using blunt-ended hollow stainless steel needles. However, the invention is equally adaptable for using other arraying implements including but not limited to capillary tubes, micro-fabricated needles and pins, piezoelectric printing modes, and so forth.

Before depositing, or arraying, an array, the T-Tech robot was appropriately programmed by a sequence of stored commands to follow a sequence of steps, such as, collecting oligomer solution from a source well, delivering to an appropriate destination position on a glass slide, followed by appropriate number of washing and drying steps before commencing the next iteration of dipping into a different source well.

The protocol for deposition of probes on glass surface using the T-tech machine is set forth below:

1) Before deposition, probes deposition-solution were prepared by diluting or dissolved probes in 0.1 M sodium carbonate buffer (pH 9.0) at concentrations of 2 $\mu$M to 20 mM and arranged in standard 384 well microtiter plates.
2) Needles take up probe solutions by capillary effect upon being dipped into sample solutions stored in a 384 well microtiter plate.
3) Probe solutions are deposited on derivatized glass slides by bringing the tip of the needles into contact with the slide surface. Each needle delivered a drop of oligomer solution of approximately 25 nl volume, creating a cell of approximately 200 $\mu$m diameter.
4) Needles were dipped repeatedly into the same probe well, if more samples of that probe copies are to be deposited on a surface. Otherwise, before being dipped in another probe solution, needles were washed by immersing in a reservoir of deionized water for a few seconds followed by contacting with the tissues on the drying station to absorb the liquid from the needles for drying.

After depositing the probe solutions on a derivatized glass surface, the following processing protocol was performed to cause bonding of the probes to the surface.

1) Arrayed slides were incubated for 1 hr at 37° C. in a petri dish containing a piece of Whatman #1 paper soaked in deionized H$_2$O (not in contact with the arrayed slide). During rehydration, the amino group modification on the probes reacted with the diisothiocyanate groups on modified glass surfaces and formed covalent bonds.
2) The slides were then treated with 1% NH$_4$OH for 2 minutes at room temperature followed by three washes with deionized H$_2$O.
3) Arrayed slides were stored in a vacuum desiccator and kept in dark at room temperature.

This arraying protocol was used to deposit the test arrays described subsequently. This protocol is suitable to construct arrays having up to 4096 probes and having the structure described in Section 5.2.2.

6.5 Hybridization Protocols

UDAs constructed on derivitized glass were used for various hybridization tests described in the this subsection. These included hybridization-based tests of probe deposition, of sequence recognition according to the hybridization/ligation method of Section 5.2.3, and of probe concentration.

Test of Probe Deposition

To determine preferred probe lengths for overcoming stearic hinderance to effective hybridization, and as a quality check for surface anchoring of probe oligomers according to the preceding protocol, hybridizations were performed to a deposited array with a FAM-labeled oligonucleotide at least partially complementary to core region of the probe. Sample probes MP1, MP2, and MP3, with and without FAM labels, were deposited along with the probe RHO1.

RHO1: 5'-TGGT GAT CCT TCA AGG (T)$_5$-C$_6$-amino (SEQ ID NO:76)

The labeled oligonucleotide (JC24 of Table 4) used for hybridization has the sequence:

JC24-F: 5'-Fam-ACC GAC GTC GAC TAT CCA TGA AGC (SEQ ID NO:77)

The underlined 15 nucleotide subsequence is complementary to the core region MP1, MP2, and MP3 but not to any region of RHO1.

The array was prepared according to the protocols described in Section 6.4. Probe concentrations of 20 $\mu$M were used in the deposition solutions. These probes were deposited and conjugated in two quadrants of a derivitized glass slide in the following pattern and with a cell diameter of about 300 $\mu$m and with a spacing between cells of about 750 $\mu$m.

| | | Quadrant 1 | | | |
|---|---|---|---|---|---|
| | AM | | AM | | |
| AM | F-MP1 | F-MP2 | F-MP3 | F-RHO1 | |
| | F-MP1 | F-MP2 | F-MP3 | F-RHO1 | AM |
| | F-MP1 | F-MP2 | F-MP3 | F-RHO1 | AM |
| AM | F-MP1 | F-MP2 | F-MP3 | F-RHO1 | |
| | AM | | AM | | |
| | | Quadrant 2 | | | |
| | AM | | AM | | |
| AM | MP1 | MP2 | MP3 | RHO1 | |
| | MP1 | MP2 | MP3 | RHO1 | AM |
| | MP1 | MP2 | MP3 | RHO1 | AM |
| AM | MP1 | MP2 | MP3 | RHO1 | |
| | AM | | AM | | |

The probes indicated in the following legend were deposited in the cells above.

| | |
|---|---|
| AM-alignment marker, | |
| MP1-5-T spacer, | F-MP1-Fam labeled MP1; |
| MP2-15-T spacer, | F-MP2-Fam labeled MP2; |
| MP3-0-T spacer, | F-MP3-Fam labeled MP3; |
| RHO1-negative control; | F-RHO1-Fam labeled RHO1. |

This array was hybridized with JC24 according to the following hybridization protocol.

1) A hybridization solution was prepared according to the following composition:

2.5 µl 20×SSPE 0.1 µl 10% sodium dodecyl sulfate (SDS)

1.0 µl JC24-Fam (1 pmol/µl)

6.4 µl dH2O

2) The hybridization solution was incubated for 5 min. at 90–95° C. followed by incubation on ice for 5 min.

4) 10 µl of Hybridization solution was applied onto the array area and covered with a 22×22 mm cover slip.

5) The slide assembly was incubated for 3 hrs at 25° C. in a humid chamber.

6) Hybridized slides were washed with 2 changes of 2×SSPE/0.1% SDS for 15 min each, air dried, and viewed in the microscope with laser stimulation of FAM moieties.

This protocol was performed to obtain the following results. Fluorescence signals were observed from MP1, MP2, and MP3 cells, as well as from the alignment markers. No significant fluorescence signals were observed from the negative control cells containing RHO1. Thereby, the selectivity of hybridization was demonstrated.

To compare the direct hybridization efficiency with probes having different spacer poly(T) lengths, the array was imaged using a Biorad confocal microscope, MRC 600, as described in Section 5.2.5. The total fluorescence intensities after background correction from the cells in Quadrant 2 were quantitated using Adobe Photoshop 4.0 and the NIH image program, ImagePC, as described in Section 5.2.5. The results are set forth in Table 8 below.

TABLE 8

DIRECT HYBRIDIZATION EFFICIENCY

| Probe | Length of Spacer | Avg Signal Intensity (rel. units) | Normalized Intensity | Percent Saturation |
|---|---|---|---|---|
| MP1 | 5 T's | 56,388 | 66,547 | 5.25 |
| MP2 | 15 T's | 41,741 | 64,174 | 5.05 |
| MP3 | 0 t's | 73,679 | 73,679 | 5.83 |
| Alignment Cells | N/A (not applicable) | 15,789 | | N/A |

Average hybridized cell intensity (third column) was estimated from 2 or 3 independent measurements of hybridization and normalized in view of the initial concentrations of each anchor oligomer used (between 13 and 20 pmols/µl) in order to obtain values for normalized intensity of hybridized cells (fourth column). The normalized intensities over the range of spacer lengths were comparable, suggesting equivalent hybridization efficiency for each of the oligomers. Under these deposition conditions, approximately 5% of the surface anchored probes were hybridized, which is comparable with values for hybridization efficiency obtained in similar implementations by those skilled in the art.

Test of Sequence Recognition (Direct Hybridization/Ligation)

In this example, synthetic DNA targets were used for hybridization to a test array. These targets resembled the structure of fragment samples prepared according to the methods of Sections 6.1 and 6.2, and were prepared by annealing a pair of complementary oligonucleotides. The complementary oligonucleotides JC24 (Table 4) and pMP6 shown below have a 24-base complementary region (underlined), and a duplex formed from the strands has a 5'-FAM on one strand and a single-stranded 4 base 5'-overhang, TGTC. on the other strand.

JC24: 5' FAM-ACC GAC GTC GAC TAT CCA TGA AGC (SEQ ID NO:77)

pMP6: 5'-p-TGTC GCT TCA TCC ATA GTC GAC GTC GGT-3' (SEQ ID NO:78)

The two strands were annealed according to the following protocol.

1) Mix the following in an eppendorf tube:

5 µl—Target oligomer 1 (JC24) (20 pmol/µl)

5 µl—Target oligomer 2 ( 20 pmol/µl)

10 µl—10×Ligase buffer (NEB)

to 100 µl total—dH20

2) Incubate the mix at 95° C. for 5 min. in a beaker containing 250 ml of water at 90–95° C.

3) Then allow the beaker to slowly cool down to room temperature over a period of 1–2 hr.

4) Remove the eppendorf tube from the beaker and spin briefly in micro-centrifuge.

The array employed for test of direct hybridization/ligation was prepared according to the protocols described in Section 6.4 with a cell diameter of approximately 300 µm and with a spacing between cells of approximately 750 µm in the quadrants illustrated below. Probe concentrations of 20 µM were used in the deposition solutions.

Quadrant 1

|    |    | AM    |       | AM    |        |    |
|----|----|-------|-------|-------|--------|----|
| AM |    | F-MP1 | F-MP2 | F-MP3 | F-RHO1 |    |
|    |    | F-MP1 | F-MP2 | F-MP3 | F-RHO1 | AM |
|    |    | F-MP1 | F-MP2 | F-MP3 | F-RHO1 | AM |
| AM |    | F-MP1 | F-MP2 | F-MP3 | F-RHO1 |    |
|    |    | AM    |       | AM    |        |    |

Quadrant 2

|    |    | AM  |     | AM  |      |    |
|----|----|-----|-----|-----|------|----|
| AM |    | MP1 | MP2 | MP3 | RHO1 |    |
|    |    | MP1 | MP2 | MP3 | RHO1 | AM |
|    |    | MP1 | MP2 | MP3 | RHO1 | AM |
| AM |    | MP1 | MP2 | MP3 | RHO1 |    |
|    |    | AM  |     | AM  |      |    |

Quadrant 4

| F-MP1 | F-MP3 | F-MP1 | F-MP3 |
| F-MP1 | F-MP3 | F-MP1 | F-MP3 |
| F-MP1 | F-MP3 | F-MP1 | F-MP3 |
| F-MP1 | F-MP3 | F-MP1 | F-MP3 |

The probes indicated in the following legend were deposited in the cells above. AM—alignment marker

| MP1-5 T linker, | F-MP1-Fam labeled MP1; |
| MP2-15 T linker, | F-MP2-Fam labeled MP2; |
| MP3-0 T linker, | F-MP3-Fam labeled MP3; |
| RHO1-negative control, | F-RHO1-Fam labeled RHO1. |

The following stacking oligonucleotide, which is complementary to the core region of the probes MP1, MP2, and MP3, was used in the h/l protocol.

MP5: 5'-ACC GAC GTC GAC TAT GGA-3'

An exemplary protocol used to perform h/l is set forth next.

1) Prepare the ligation mix in a total volume of 10 µl:

1 pmol annealed, duplex target 1 pmol stacking primer (MP5)

1×ligase buffer (5×Ligase buffer contains: 50% PEG Mr 6000, 330 mM Tris.HCl, 33 mM MgCl$_2$, 50 mM DTT, 5 mM ATP, and 200 mM NaCl at pH 7.5).

400 units T4 DNA ligase (NEB)
2) The arrayed slide was placed on a paper template to mark the position of the grid and 10 μl of ligation mix was applied. The solution was overlaid with a clean cover-slip without air bubbles.
3) Incubate at 37° C. in a humidified chamber for 70 minutes.
4) Following the incubation, the slides were rinsed with 10 mM Tris.HCl, 1 mM EDTA, (TE at pH 8.0) and washed with 200 ml TE at 90–95° C. for 15 min. (very stringent wash) They were dried in air and viewed in the microscope.

Varying amounts of the annealed duplex target generated using the protocol described above were ligated in separate experiments to the UDA constituted by the anchored probe oligomers, using the Direct ligation implementation of this invention.

To compare the direct hybridization/ligation efficiency with different linker poly(T) length, the slide sample was imaged using a Biorad confocal microscope, MRC 600. The total fluorescence intensities after background correction from the cells were quantitated using Adobe Photoshop 4.0 and the NIH image program, ImagePC, as previously described.

Fluorescence signals due to ligated target were observed from MP1, MP2, and MP3 cells, as well as from the alignment markers. No significant fluorescence signals were observed from the negative controls, RHO 1, showing the selectivity of stacking-ligation.

The results of these hybridization/ligation experiments using 1 pmol of the duplex target KC 24/pMP6 are set forth in Table 9 below.

TABLE 9

HYBRIDIZATION/LIGATION RESULTS (1 PMOL)

| Probe | Length of Spacer | Average Signal Intensity (relative units) | Hybridization (%) |
|---|---|---|---|
| MP1 | 5 T's | 135,879 | 0.017 |
| MP2 | 15 T's | 82,934 | 0.011 |
| MP3 | 0 t's | 114,250 | 0.015 |
| Alignment Cells | N/A | 195,946 | N/A |
| RHO1 | Negative control | 0 | 0.0 |

These results showed that, first, hybridization signals were obtained only from probes having a hybridization region complementary to the single-stranded terminal subsequence of the target nucleic acid. No signal was obtained from probe RHO1. Second, as observed for direct hybridization, the ligation efficiencies did not significantly vary with the length of the spacer alone. Accordingly, interactions of the probe and the target during ligation are less constrained by stearic effects due to probe length. The probe is more accessible to the DNA ligase enzyme than it is for direct hybridizations, which requires a more extensive interaction along the full length of the oligomer portion of the anchored probe.

These conclusion are confirmed by additional results for hybridization/ligation performed according to the above protocol but with 100 fmol of target nucleic acids and stacking oligomers. (Again, probe concentrations of 20 μM were used in the deposition solutions.) Results for these concentration are set forth in Table 10.

TABLE 10

HYBRIDIZATION/LIGATION RESULTS (100 FMOL)

| Probe | Length of Spacer | Average Signal Intensity (relative units) | Hybridization (%) |
|---|---|---|---|
| MP1 | 5 T's | 12,820 | 0.021 |
| MP2 | 15 T's | 17,077 | 0.029 |
| MP3 | 0 t's | 17,780 | 0.030 |
| Alignment Cells | N/A | 148,585 | N/A |

The average ligation efficiency using 100 fmol target again did not vary significantly over the range of spacer lengths employed.

On the other hand, ligation efficiencies varied with target concentration with 1 pmol or 100 fmol target and spacer length. Preferable results were found for the probe MP1 (having 5 T nucleotides). The ratio of average cell hybridization intensity for ligations with MP1 using a 10-fold range of (1 pmol:100 fmol) target concentrations was 10.76. Thereby, among these three probes tested, MP1 is preferred for obtaining the most pseudo-linear hybridization signal response in this range of target concentrations.

Test of Probe Concentration

The effects of probe concentration in the probe deposition solution was tested by preparing an detection array from solutions of varying probe concentration. This array was then hybridized with target nucleic acids and the fluorescence signal intensity was observed. Solutions with probe concentrations varying over a 10,000 fold range, from 2 μM to 20 mM, each increment being 10 fold concentration change, were tested.

Oligomer solutions representing an incremental range of initial concentrations were deposited and anchored on derivatized slides as described in Section 6.5, Probe Deposition Test.

In more detail, the array employed for the probe concentration test was prepared according to the protocols described in Section 6.4 with a cell diameter of approximately 300 μm and with a spacing between cells of approximately 750 μm in the four quadrants illustrated below (only quadrant 3 was of interest for this test).

Quadrant 1

|    | AM    |       | AM    |        |    |
|----|-------|-------|-------|--------|----|
| AM | F-MP1 | F-MP2 | F-MP3 | F-RHO1 |    |
|    | F-MP1 | F-MP2 | F-MP3 | F-RHO1 | AM |
|    | F-MP1 | F-MP2 | F-MP3 | F-RHO1 | AM |
| AM | F-MP1 | F-MP2 | F-MP3 | F-RHO1 |    |
|    | AM    |       | AM    |        |    |

Quadrant 2

|    | AM  |     | AM  |      |    |
|----|-----|-----|-----|------|----|
| AM | MP1 | MP2 | MP3 | RHO1 |    |
|    | MP1 | MP2 | MP3 | RHO1 | AM |
|    | MP1 | MP2 | MP3 | RHO1 | AM |
| AM | MP1 | MP2 | MP3 | RHO1 |    |
|    | AM  |     | AM  |      |    |

Quadrant 3

|    | AM |   | AM |   |   |    |
|----|----|---|----|---|---|----|
| AM | A  | B | C  | D | E | AM |
|    | A  | B | C  | D | E | AM |
| AM | A  | B | C  | D | E |    |
|    | A  | B | C  | D | E |    |
|    | AM |   | AM |   |   |    |

-continued

| | | | Quadrant 4 | | | |
|---|---|---|---|---|---|---|
| | AM | | AM | | | |
| AM | A | B | C | D | F | AM |
| | A | B | C | D | F | AM |
| AM | A | B | C | D | F | |
| | A | B | C | D | F | |
| | AM | | AM | | | |

The probes indicated in the following legend were deposited in the cells above. AM—alignment marker
A—probe AcGn-1 deposited from a solution of 2 μM
B—probe AcGn-1 deposited from a solution of 20 μM
C—probe AcGn-1 deposited from a solution of 200 μM
D—probe AcGn-1 deposited from a solution of 2 mM
E—probe AcGn-1 deposited from a solution of 20 mM
F—probe MP1-Fam deposited from a solution of 200 pM
The sequence of the AcGn-1 probe oligomer follows:
AcGn-1: 5'-GGTA CTG TGC TAT CCG AGG GAA $(T)_5$-$C_6$-amino-3' (SEQ ID NO:75)

Target nucleic acids for the h/l method were prepared by hybridizing oligomers TaGn-1 and TGn-1-F according to the protocol previously described in the subsection "Sequence Recognition Test." Sequences of these oligomers follow:
TaGn-1: 5'-TAC CAC CGG GCT TCA TCC ATA GTC GAC GTC GGT-3' (SEQ ID NO:79)
TGn-1-F: 5' Fam-ACC GAC GTC GAC TAT GGA TGA AGC CCG GT-3' (SEQ ID NO:80)
The sequence of the stacking oligomer, StGn-1, follows:
StGn-1: 5'-TTC CCT CGG ATA GCA CAG-3' (SEQ ID NO:81)

The prepared UDA slide was used in the h/l method according to the protocol described previously in the subsection "Sequence Recognition Test" The hybridized slide samples were imaged using a Biorad confocal microscope, MRC 600 and total fluorescence intensities after background correction from the cells were quantitated, also as previously described. Observations were made from the 4 distinct probe cells, derived from probe solution of the indicated concentrations, and averaged.

The results of the probe concentration test are set forth in Table 11.

TABLE 11

HYBRIDIZATION/LIGATION RESULTS (1 PMOL)

| Probe Deposition Conc. | Average Signal Intensity (relative units) | Standard Deviation of Intensity |
|---|---|---|
| 2 μm | 398,329 | 30,620 |
| 20 μm | 271,731 | 24,618 |
| 200 μm | 202,893 | 13,591 |
| 2 mM | 346,184 | 31,319 |
| 20 mM | 903,944 | 68,438 |

FIG. 10 illustrates a graph of these results. One axis records the average hybridization signal intensity from probe cells (in relative units). The other axis records the probe deposition-solution concentration on a base 10 logarithm scale.

In general, these results indicate that the intensities of hybridization signals observed from probe cells deposited with probe solution concentrations of 2 μM are comparable to the intensities observed from cells deposited with probe solution concentrations of 20 mM (which the prior art teaches as approximately optimal). Signal intensity at 20 mM is only a little more than 2-fold greater than at 2 μm. In detail, there was a 2-fold decrease in the signal intensity as probe deposition-solution concentration increased from 2 μM to 200 μM (100-fold increase), followed by a 4.5-fold increase as probe deposition-solution concentration increased from 200 μM to 20 mM (another 100-fold increase).

In summary, the use of probe deposition-solution concentrations of approximately 2 μM, or of approximately between 2 μM and 200 μM, gives adequate hybridization signal intensity and requires considerably less probe than the use of probe deposition-solution concentrations above 200 μM and up to 20 mM (as taught in the prior art).

The inventors believe that these results are explained either by stearic effects, which hinder hybridization as probe densities increase, or by small changes in ligation efficiency accompanying varying probe concentrations. The latter effects have been demonstrated for ligations of foreign DNA to linearized plasmid DNA (see, e.g., Sambrook et al., 1989, *Molecular Cloning B A Laboratory Manual*, Cold Spring Harbor Press, New York).

6.6 Strand-Invasion Protocols

A protocol for stand-invasion ligation is set forth below.
1) Prepare the ligation mixture containing:
   2 to 20 pmol of duplex target nucleic acids
   2 to 20 pmol of stacking oligonucleotide (1:1 molar ratio with target)
   1×Ligase buffer (NEB)
   400 U T4 DNA Ligase (NEB)
3) Incubate at 37° C. in a humidified chamber for 2 hrs.
4) Wash the slides by immersing in 0.5×SSPE/0.1% SDS at 25–30° C. for 15–30 min. They were dried in air and viewed in the microscope.

An alternative protocol for the strand-invasion method uses Ampligase:
1) Prepare the ligation mixture containing:
   2 to 20 pmol of duplex target nucleic acids
   2 to 20 pmol of stacking oligonucleotide (1:1 molar ratio with target)
   1×Ampligase buffer (Epicentre)
   100 U T4 DNA Ligase (Epicentre)
3) Incubate at 45° C. in a humidified chamber for 2 hrs.
4) Wash the slides by immersing in 0.5×SSPE/0.1% SDS at 45–50° C. for 15–30 min. Dry slides in air and view in the microscope.

A test target nucleic acid can be constructed by annealing strands of the following sequences.
RHO3: 5'-pGATC ACCA GTA TGG TGG CCA GCG GC-3' (SEQ ID NO:82)
RHO3COMP: 3'-TGGT CAT ACC ACC GGT CGC CG-5' (SEQ ID NO:83)

A stacking oligomer suitable for stand invasion has the following sequence.
RHO1 5'-TGGT GAC GCT TCA AGG $(T)_5$-$C_6$-amino-3' (SEQ ID NO:84)

6.7 Fluorescent Labels

Table 12 lists various fluorescent labels that can be used in this invention where fluorescent labels have been specified.

TABLE 12

FLORESCENT LABELS

| Fluorochrome | Vendor | Absorption Maximum | Emission Maximum |
|---|---|---|---|
| Bodipy 493/503 | Molecular Probes | 493 | 503 |
| Cy2 | BDS | 489 | 505 |
| Bodipy FL | Molecular Probes | 508 | 516 |
| FTC | Molecular Probes | 494 | 518 |
| FluorX | BDS | 494 | 520 |
| FAM | Perkin-Elmer | 495 | 535 |
| Carboxy-rhodamine | Molecular Probes | 519 | 543 |
| EITC | Molecular Probes | 522 | 543 |
| Bodipy 530/550 | Molecular Probes | 530 | 550 |
| JOE | Perkin-Elmer | 525 | 557 |
| HEX | Perkin-Elmer | 529 | 560 |
| Bodipy 542/563 | Molecular Probes | 542 | 563 |
| Cy3 | BDS | 552 | 565 |
| TRITC | Molecular Probes | 547 | 572 |
| LRB | Molecular Probes | 556 | 576 |
| Bodipy LMR | Molecular Probes | 545 | 577 |
| Tamra | Perkin-Elmer | 552 | 580 |
| Bodipy 576/589 | Molecular Probes | 576 | 589 |
| Bodipy 581/591 | Molecular Probes | 581 | 591 |
| Cy3.5 | BDS | 581 | 596 |
| XRITC | Molecular Probes | 570 | 596 |
| ROX | Perkin-Elmer | 550 | 610 |
| Texas Red | Molecular Probes | 589 | 615 |
| Bodipy TR (618?) | Molecular Probes | 596 | 625 |
| Cy5 | BDS | 650 | 667 |
| Cy5.5 | BDS | 678 | 703 |
| DdCy5 | Beckman | 680 | 710 |
| Cy7 | BDS | 443 | 767 |
| DbCy7 | Beckman | 790 | 820 |

The suppliers listed in Table 12 are Molecular Probes (Eugene, Oreg.), Biological Detection Systems ("BDS") (Pittsburgh, Pa.) and Perkin-Elmer (Norwalk, Conn.).

Means of utilizing these fluorochromes by attaching them to particular nucleotide groups are described in Kricka et al., 1995, Molecular Probing, Blotting, and Sequencing, chap. 1, Academic Press, New York. Preferred methods of attachment are by an amino linker or phosophoramidite chemistry.

Table 13 lists various pairs of fluorescent transfer dyes that can be used in this invention where labels have been specified.

TABLE 13

FLORESCENT ENERGY-TRANSFER LABELS

| Donor Fluorochrome | Acceptor Fluorochrome | Vendor |
|---|---|---|
| 3-(epsilon-carboxy-pentyl)-3'ethyl-5,5'-dimethyloxacarbocyanine (CYA) | FAM, R6G, TAMRA, or ROX | 1, 2 |
| 6-carboxyfluorescein (FAM) | 6-carboxy-4',5'-dichloro-2',7'-dimethoxy-fluorescein (JOE); 5- or 6-carboxy-rhodamine-6G. | 1 |
| 5- or 6-carboxy 4'-aminomethylfluorescein | 4,7-dichloro-substituted rhodamine | 3 |
| Orange-thiazole-indolenine (butylTOTIN) | Orange-thiazole blue (pentylTOTAB) | 4 |
| 5-iodoacetamidofluorescein | 5-iodoacetamido-fluorescein | 1 |
| Bis(phenanthroline)(dipyridophenazine)ruthenium(II) [Ru(phen)2dppz2+] | Bis(9,10-phenanthrenequinone diimine)(phenanthroline)rhodium(III) [Rh(phi)2phen3+] | 5 |
| Coumarin | Ethidium | 1 |
| 2-methoxy-6-chloro-9-amino-acridine | Ethidium | 1 |

TABLE 13-continued

FLORESCENT ENERGY-TRANSFER LABELS

| Donor Fluorochrome | Acceptor Fluorochrome | Vendor |
|---|---|---|
| 5-(dimethylamino)-1-naphthalenesulfonyl group (DNS) | 7-amino-4-methyl-coumarin-3-acetyl (AMCA) | 1 |
| N-(p-(2-benzoxazolyl)phenyl)-maleimide (BMI) | Fluram | 6 |

The vendor or reference numbers are as follows: number 1 is Molecular Probes, Eugene, Oreg.; number 2 is Hung et al. (1996) Anal. Biochem. 243(1):15–27; number 3 is Hung et al. (1996) Anal. Biochem. 238(2):165–170; number 4 is Zeng et al. (1995) Anal. Biochem. 231(1):256–260; number 5 is Murphy et al. (1994) Proc. Natl. Acad. Sci. U S A 91:5315–5319; number 6 is Fuchs et al. (1997) Gen. Physiol. Biophys. 16:15–28.

6.8 Coverage with Type II Restriction Endonucleases

An exemplary search was performed of sequence databases in order to find cDNAs containing pairs of primary subsequences, which were selected from the recognition sequences of Type II REs. As additional pairs of REs were selected, additional cDNAs were found. The cumulative percentage of found cDNAs versus the number of pairs of REs is illustrated in FIG. 8. This figure represents the percent coverage of a sample of nucleic acids derived from cDNAs that can be expected from the indicated number of subsamples produced by the selected REs according to the protocols of Section 6.1.2.

These searches were performed by software according to the methods described in Section 5.1.3. The database used for human cDNA was the TIGR (The Institute for Genome Research). GenBank (National Institute of Health) was used for mouse, rat, yeast, and corn sequences. The search was performed of the most recent database release as of the date of the search. Only sequences longer than 1000 bp in the database were included in the search.

The pairs of Type II restriction endonucleases are set forth in Table 14.

TABLE 14

RE PAIRS SEARCHED

RE PAIRS SEARCHED

| | | | |
|---|---|---|---|
| BclI/Acc65I | BamHI/BspHI | MfeI/HindIII | BglII/XhoI |
| BglII/Acc65I | XbaI/BsrGI | EcoRI/HindIII | EcoRI/Bsp120I |
| BglII/EagI | BamHI/HindIII | HindIII/BclI | EcoRI/NheI |
| ApoI/SpeI | BclI/EcoRI | NcoI/NheI | NheI/ApaLI |
| BglII/EcoRI | BglII/BspEI | NheI/BclI | BsrFI/BglII |
| BspHI/EcoRI | BglII/BspHI | NheI/BglII | ApoI/BstYI |
| BspHI/NgoMI | BglII/BsrGI | SpeI/BclI | AvrII/BamHI |
| BspEI/BclI | BglII/HindIII | SpeI/BglII | AvrII/BclI |
| BsaWI/HindIII | BspEI/BspHI | ApoI/NgoMI | AvrII/BsrGI |
| ApoI/BamHI | BspEI/BsrGI | BsrGI/HindIII | BclI/ApaLI |
| AvrII/BglII | BspEI/NcoI | BstYI/XhoI | BclI/BsrGI |
| XbaI/BglII | MfeI/BsrGI | ApoI/BspEI | BglII/KasI |

7 Specific Embodiments, Citation of References

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for identifying nucleic acids in a sample of nucleic acids comprising:

(a) observing subsequence sets present in said sample of nucleic acids, wherein a subsequence set comprises at least a first primary nucleotide subsequence, a second primary nucleotide subsequence, and an additional nucleotide subsequence, and wherein said additional nucleotide subsequence is spaced apart from said first primary nucleotide subsequence by a fixed distance of zero or more nucleotides which is the same in all subsequence sets and said second primary nucleotide subsequence is not adjacent to either said additional nucleotide subsequence or said first primary subsequence and wherein said second primary nucleotide subsequence is spaced apart from said additional nucleotide subsequence by one or more nucleotides; and wherein said step of observing comprises the steps of:

(i) providing at least one subsample of one or more species of first nucleic acid fragments, said species of first nucleic acid fragments in said subsample being derived from those nucleic acids in said sample, selected sequences for said first primary nucleotide subsequences and said second primary nucleotide subsequences having been chosen for said sample; and (ii) determining the sequence of said additional nucleotide subsequence in each said species of first nucleic acid fragments of said subsample; and (b) searching a database of nucleic acid sequences in order to locate database sequences having said observed subsequence sets or to determine that no such database sequences exist, said database of nucleic acid sequences comprising nucleic acid sequences that might be present in said sample; wherein a database sequence has a particular observed subsequence set (i) if it has the first primary nucleotide subsequence, the second primary nucleotide subsequence, and the additional nucleotide subsequence of the particular observed subsequence set, (ii) if the additional nucleotide subsequence is spaced apart from the first primary nucleotide subsequence by the same fixed distance as in the particular observed subsequence set, and (iii) if said second primary nucleotide subsequence is spaced apart from said additional nucleotide subsequence by one or more nucleotides;

thereby identifying said located database sequences as sequences of nucleic acids present in said sample.

2. The method of claim 1 wherein said fixed distance is zero nucleotides.

3. The method of claim 1 wherein the length of said first primary nucleotide subsequence is at least six nucleotides, the length of said second primary nucleotide subsequence is at least six nucleotides, and the length of said additional nucleotide subsequence is at least four nucleotides.

4. The method of claim 1 wherein the length of said first primary nucleotide subsequence is six nucleotides, the length of said second primary nucleotide subsequence is six nucleotides, and the length of said additional nucleotide subsequence is at least six nucleotides.

5. The method of claim 1 wherein the length of said first primary nucleotide sequence, the length of said second primary nucleotide sequence, and the length of said additional nucleotide sequence are chosen such that on average a particular subsequence set occurs in less than approximately 10 sequences in said sequence database.

6. The method of claim 1 wherein the length of said first primary nucleotide sequence, the length of said second primary nucleotide sequence, and the length of said additional nucleotide sequence are chosen such that on average a particular subsequence set occurs in less than approximately 5 sequences in said sequence database.

7. The method of claim 1 wherein said providing step provides a plurality of subsamples, each subsample having different selected sequences for said first primary nucleotide subsequence or said second primary nucleotide subsequence.

8. The method of claim 1 wherein the length of said first primary nucleotide sequence, the length of said second primary nucleotide sequence, and the length of said additional nucleotide sequence are chosen such that on average the number of species of first nucleic acid fragments in said subsample is less than the number of possible sequences for said additional nucleotide subsequences.

9. The method of claim 1 wherein said first and said second primary nucleotide subsequences are sequences of recognition sites of restriction endonucleases of a type that cuts nucleic acids within their recognition sites, and wherein said providing step comprises digesting said sample with restriction endonucleases whose recognition sites have the sequences selected for said first and second primary nucleotide subsequences.

10. A The method of claim 9 wherein said providing step further comprises, after said digesting, the steps of (i) hybridizing digested nucleic acids with adapter nucleic acids, said adapter nucleic acids being partially double-stranded, each said adapter nucleic acid being complementary to an end of a nucleic acid digested by one of said restriction endonucleases, and (ii) ligating said hybridized nucleic acids and adapter nucleic acids.

11. A method for identifying nucleic acids in a sample of nucleic acids comprising:
(a) observing subsequence sets present in said sample of nucleic acids, wherein a subsequence set comprises at least a first primary nucleotide subsequence, a second primary nucleotide subsequence, and an additional nucleotide subsequence, and wherein said additional nucleotide subsequence is spaced apart from said first primary nucleotide subsequence by a fixed distance of zero or more nucleotides which is the same in all subsequence sets and said second primary nucleotide subsequence is not adjacent to either said additional nucleotide subsequence or said first primary subsequence and wherein said second primary nucleotide subsequence is spaced apart from said additional nucleotide subsequence by one or more nucleotides; and wherein said step of observing comprises the steps of:
(i) providing at least one subsample of one or more species of first nucleic acid fragments, said species of first nucleic acid fragments in said subsample being derived from those nucleic acids in said sample, selected sequences for said first primary nucleotide subsequences and said second primary nucleotide subsequences having been chosen for said sample; and
(ii) determining the sequence of said additional nucleotide subsequence in each said species of first nucleic acid fragments of said subsample; wherein said determining step comprises:
(A) producing second nucleic acid fragments from said first nucleic acid fragments of said subsample, wherein said second nucleic acid fragments have a single-stranded terminal nucleotide subsequence, and wherein said additional nucleotide subsequence comprises said single-stranded terminal nucleotide subsequence;
(B) hybridizing a plurality of species of probe molecules with said second nucleic acid fragments, probe molecules of each of said species of probe molecules capable of hybridizing with said second nucleic acid fragments having a particular sequence for said additional nucleotide subsequence; and (C) detecting which of said species of probe molecules has hybridized with said second nucleic acid fragments;
whereby the sequences of said additional nucleotide sequences are determined; and
(b) searching a database of nucleic acid sequences in order to locate database sequences having said observed subsequence sets or to determine that no such database sequences exist, said database of nucleic acid sequences comprising nucleic acid sequences that might be present in said sample; wherein a database sequence has a particular observed subsequence set (i) if it has the first primary nucleotide subsequence, the second primary nucleotide subsequence, and the additional nucleotide subsequence of the particular observed subsequence set, (ii) if the additional nucleotide subsequence is spaced apart from the first primary nucleotide subsequence by the same fixed distance as in the particular observed subsequence set, and (iii) if said second primary nucleotide subsequence is spaced apart from said additional nucleotide subsequence by one or more nucleotides;
thereby identifying said located database sequences as sequences of nucleic acids present in said sample.

12. The method of claim 11 wherein said species of probe molecules are fixed on a surface in an arrangement such that each species of probe molecule occupies a discrete observational region of said surface separate from regions occupied by other species of probe molecules.

13. The method of claim 11 further comprising, before said detecting step, a step of washing said probe molecules hybridized with said second nucleic acid fragments at a stringency to remove mis-hybridized or non-specifically bound second nucleic acid fragments.

14. The method of claim 11 wherein said second fragments are labeled with a detectable moiety.

15. The method of claim 14 wherein said detectable moiety is a fluorescent moiety or a moiety recognizable by an antibody conjugated to a detectable moiety.

16. The method of claim 11 wherein said producing step comprises digesting said fragments in said subsample with a restriction endonuclease of a type that cuts nucleic acids outside of its recognition site.

17. The method of claim 11 wherein said probe molecules comprise a peptido-nucleic acid subsequence, such that for each species of said probe molecule the sequence of said peptido-nucleic acid subsequence is complementary to the sequence of said additional subsequence hybridizable to said species of probe molecules.

18. The method of claim 11 wherein each of said probe molecules comprises a nucleotide sequence, which in turn comprises a hybridization region nucleotide subsequence and a core nucleotide subsequence, the sequence of said hybridization region nucleotide subsequence being complementary to the sequence of said additional subsequence hybridizable to said species of probe molecules, said core nucleotide subsequence being adjacent to said hybridization region nucleotide subsequence, and wherein said step of hybridizing comprises:
(a) hybridizing a plurality of species of probe molecules with said second nucleic acid fragments and with stacking oligomers to form a hybridization structure, the sequence of said stacking oligomers being complementary to a hybridizable portion of the sequence of said core nucleotide subsequence of said probe molecules, said hybridizable portion being adjacent to said hybridization region nucleotide subsequence; and (b) ligating nicks in said hybridization structure.

19. The method of claim 18 wherein said additional nucleotide subsequence consists of said single-stranded terminal nucleotide subsequence of said second nucleic acid fragments.

20. The method of claim 18 wherein said additional nucleotide subsequence comprises said single-stranded terminal nucleotide subsequence of said second nucleic acid fragments and a double-stranded nucleotide subsequence of said second nucleic acid fragments, said double-stranded terminal nucleotide subsequence being adjacent to said single-stranded nucleotide subsequence.

21. The method of claim 18 wherein said stacking oligomers are labeled with a detectable moiety.

22. The method of claim 21 wherein said detectable moiety comprises a fluorescent energy transfer dye.

23. The method of claim 22 wherein said fluorescent energy transfer dye comprises a donor moiety and an acceptor moiety, and wherein one of said donor or said acceptor moieties is not conjugated to said stacking oligomer.

24. The method of claim 18 wherein said second nucleic acid fragments are labeled with a detectable moiety.

25. The method of claim 24 wherein said detectable moiety comprises a fluorescent energy transfer dye, wherein said fluorescent energy transfer dye comprises a donor moiety and an acceptor moiety, and wherein one of said donor or said acceptor moieties is not conjugated to said second nucleic acid fragments.

26. The method of claim 18 wherein said hybridizing and said ligating steps are (i) performed under conditions such that the concentration of said second nucleic acid fragments is less than concentrations of said probe molecules, and (ii) stopped before said second nucleic acid fragments become depleted.

27. The method of claim 11 wherein said detecting step additionally detects the amount of said second nucleic acid fragments hybridized with said species of probe molecule.

28. The method of claim 1 further comprising, after said determining step, a step of amplifying one or more species of first nucleic acid fragments in said subsample by contacting said subsample with a nucleic acid polymerase and one or more primers, at least one primer being a phasing primer which comprises a subsequence with the same sequence as one of said determined additional subsequences.

29. The method of claim 28 further comprising, after said amplifying step, a step of sequencing at least a portion of one or more nucleic acid products of said amplifying step.

30. The method of claim 29 wherein said determined sequences are compared with said located database sequences that contain a sequence set comprising said selected first primary nucleotide sequence, said selected first primary nucleotide sequences, and said determined additional subsequence.

31. The method of claim 30 further comprising, after said amplifying and searching steps, storing the results of said amplifying in a permanent storage.

32. The method of claim 1 wherein said searching step further comprises examining individually and sequentially each sequence in the sequence database for the presence of a sequence set.

33. The method of claim 1 wherein said searching step comprises representing a sequence set as a regular expression in order to search sequences in the sequence database.

34. The method of claim 1 further comprising, prior to said searching step, a step of constructing an index of subsequences present in the sequences of said sequence database, and wherein said searching step consults said index of subsequences.

35. The method of claim 1 further comprising, after said searching step, a step of storing said located sequences in a permanent computer-readable storage.

36. The method of claim 35 where said step of storing stores along with said located sequences additional information describing said sample of nucleic acids.

37. The method of claim 35 wherein said step of observing further observes the amount of nucleic acids in said sample having said observed subsequence sets, and wherein said step of storing stores along with said located sequences said observed amount.

38. A method for identifying and quantifying nucleic acids in a sample of nucleic acids comprising:
(a) providing at least one subsample of first nucleic acid fragments, said first nucleic acid fragments in said subsample being derived from those nucleic acids in said sample in which a first primary nucleotide subsequence and a second primary nucleotide subsequence have selected sequences, wherein said first and said second primary nucleotide subsequences are not contiguous in said nucleic acids;
(b) producing second nucleic acid fragments having a single-stranded terminal nucleotide subsequence from said subsample of first nucleic acid fragments;
(c) determining a sequence for an additional nucleotide subsequence of said second nucleic acid fragments, said additional nucleotide subsequence comprising said single-stranded terminal nucleotide subsequence, and wherein said single-stranded nucleotide subsequence is spaced apart from said first primary nucleotide subsequence by a distance of zero or more nucleotides which is the same in all second nucleic acid fragments, said determining by:
(i) hybridizing a plurality of species of probe molecules with said second nucleic acid fragments, each of said species of probe molecules capable of hybridizing with said second nucleic acid fragments having a particular sequence for said additional nucleotide subsequence, and
(ii) detecting which of said species of probe molecules has hybridized with said second nucleic acid fragments, and the amount of said second nucleic acid fragments hybridized with said species of probe molecule;
(d) searching a database of nucleic acid sequences in order to locate database sequences having said selected first primary subsequence, said selected second primary subsequence, and said determined additional subsequence or to determine that no such database sequences exist, said database of nucleic acid sequences comprising nucleic acid sequences that might be present in said sample; wherein a database sequence has a particular observed subsequence set (i) if it has the first primary nucleotide subsequence, the second primary nucleotide subsequence, and the additional nucleotide subsequence of the particular observed subsequence set, (ii) if the additional nucleotide subsequence is spaced apart from the first primary nucleotide subsequence by the same fixed distance as in the particular observed subsequence set, and (iii) if said second primary nucleotide subsequence is spaced apart from said additional nucleotide subsequence by one or more nucleotides;
thereby identifying said located database sequences as sequences of nucleic acids present in said sample.

39. The method of claim 38 wherein said probe molecules comprise a nucleotide sequence, which in turn comprises a hybridization region nucleotide subsequence and a core nucleotide subsequence, the sequence of said hybridization region nucleotide subsequence being complementary to the sequence of said additional subsequence hybridizable to said species of probe molecules, said core nucleotide subsequence being adjacent to said hybridization region nucleotide subsequence, and wherein said step of hybridizing comprises:

(a) hybridizing a plurality of species of probe molecules with said second nucleic acid fragments and with stacking oligomers to form a hybridization structure, the sequence of said stacking oligomers being complementary to a hybridizable portion of the sequence of said core nucleotide subsequence of said probe molecules, said hybridizable portion being adjacent to said hybridization region nucleotide subsequence; and (b) ligating nicks in said hybridization structure.

40. The method of claim 38 wherein said additional nucleotide subsequence consists of said single-stranded terminal nucleotide subsequence of said second nucleic acid fragments.

41. The method of claim 38 wherein said additional nucleotide subsequence comprises said single-stranded terminal nucleotide subsequence of said second nucleic acid fragments and a double-stranded nucleotide subsequence of said second nucleic acid fragments, said double-stranded terminal nucleotide subsequence being adjacent to said single-stranded nucleotide subsequence.

42. A method for differential gene expression analysis comprising:

(a) applying the method of claim 1 to a nucleic acid sample derived from a first tissue;

(b) applying the method of claim 1 to a nucleic acid sample derived from a second tissue; and (c) comparing the nucleic acids identified in step (a) with the nucleic acids identified in step (b).

43. The method of claim 42 wherein said first tissue comprises a particular tissue in a first state, and wherein said second tissue comprises said particular tissue in a second state.

44. The method of claim 12 wherein said species of probe molecules are in a detection array, said array comprising:

(a) one or more surfaces; and (b) a plurality of discrete observational cells arranged on said surfaces in which are bound probe molecules, each probe molecule being a member of one of a plurality of species of probe molecules, wherein each discrete observational cell has bound probe molecules of at most one species, and wherein said probe molecules comprise:

(i) a hybridization region, wherein said hybridization region of said probe molecules of one species of probe molecule are capable of hybridizing with said terminal subsequences of said target nucleic acids having a single nucleotide sequence, (ii) a core region adjacent to and conjugated with said hybridization region, and (iii) an attachment means for binding said hybridization region and said core region to said surfaces.

45. The method of claim 44 wherein said array further comprises a plurality of discrete error-checking cells to which are bound probe molecules, wherein to each discrete error-checking cell are bound probe molecules of a plurality of species, such that each species of probe molecule is bound to one discrete observational cell and to at least one discrete error-checking cell.

* * * * *

SEQUENCE LISTING

<160> NUMBER OF SEQ ID NOS: 88

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agcactctcc agcctctcac cgaa                                              24

<210> SEQ ID NO 2
<211> LENGTH: 12
<212> TYPE: DNA
<213> ORGANISM: Artificial Sequence
<220> FEATURE:
<223> OTHER INFORMATION: Primer

<400> SEQUENCE: 2
agtggctttt aa                                                           12

<210> SEQ ID NO 3
<211> LENGTH: 12
<212> TYPE: DNA
<213> ORGANISM: Artificial Sequence
<220> FEATURE:
<223> OTHER INFORMATION: Primer

<400> SEQUENCE: 3
agtggcttgt ac                                                           12

<210> SEQ ID NO 4
<211> LENGTH: 12
<212> TYPE: DNA
<213> ORGANISM: Artificial Sequence
<220> FEATURE:
<223> OTHER INFORMATION: Primer

<400> SEQUENCE: 4
agtggcttgg cc                                                           12

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
agcactctcc agcctctcac cgaa                                              24

<210> SEQ ID NO 6
<211> LENGTH: 12
<212> TYPE: DNA
<213> ORGANISM: Artificial Sequence
<220> FEATURE:
<223> OTHER INFORMATION: Primer

<400> SEQUENCE: 6
agtggctttt aa                                                           12

<210> SEQ ID NO 7
<211> LENGTH: 12

```
<212> TYPE: DNA
<213> ORGANISM: Artificial Sequence
<220> FEATURE:
<223> OTHER INFORMATION: Primer

<400> SEQUENCE: 7
agtggcttgt ac                                                              12

<210> SEQ ID NO 8
<211> LENGTH: 12
<212> TYPE: DNA
<213> ORGANISM: Artificial Sequence
<220> FEATURE:
<223> OTHER INFORMATION: Primer

<400> SEQUENCE: 8
agtggcttgg cc                                                              12

<210> SEQ ID NO 9
<211> LENGTH: 12
<212> TYPE: DNA
<213> ORGANISM: Artificial Sequence
<220> FEATURE:
<223> OTHER INFORMATION: Primer

<400> SEQUENCE: 9
agtggcttgc gc                                                              12

<210> SEQ ID NO 10
<211> LENGTH: 12
<212> TYPE: DNA
<213> ORGANISM: Artificial Sequence
<220> FEATURE:
<223> OTHER INFORMATION: Primer

<400> SEQUENCE: 10
agtggcttga tc                                                              12

<210> SEQ ID NO 11
<211> LENGTH: 12
<212> TYPE: DNA
<213> ORGANISM: Artificial Sequence
<220> FEATURE:
<223> OTHER INFORMATION: Primer

<400> SEQUENCE: 11
agtggcttct ag                                                              12

<210> SEQ ID NO 12
<211> LENGTH: 12
<212> TYPE: DNA
<213> ORGANISM: Artificial Sequence
<220> FEATURE:
<223> OTHER INFORMATION: Primer

<400> SEQUENCE: 12
agtggcttcg cg                                                              12

<210> SEQ ID NO 13
<211> LENGTH: 12
<212> TYPE: DNA
<213> ORGANISM: Artificial Sequence
<220> FEATURE:
<223> OTHER INFORMATION: Primer

<400> SEQUENCE: 13
```
agtggcttcc gg                                                       12

<210> SEQ ID NO 14
<211> LENGTH: 12
<212> TYPE: DNA
<213> ORGANISM: Artificial Sequence
<220> FEATURE:
<223> OTHER INFORMATION: Primer

<400> SEQUENCE: 14
agtggcttca tg                                                       12

<210> SEQ ID NO 15
<211> LENGTH: 12
<212> TYPE: DNA
<213> ORGANISM: Artificial Sequence
<220> FEATURE:
<223> OTHER INFORMATION: Primer

<400> SEQUENCE: 15
agtggcttag ct                                                       12

<210> SEQ ID NO 16
<211> LENGTH: 12
<212> TYPE: DNA
<213> ORGANISM: Artificial Sequence
<220> FEATURE:
<223> OTHER INFORMATION: Primer

<400> SEQUENCE: 16
agtggcttac gt                                                       12

<210> SEQ ID NO 17
<211> LENGTH: 12
<212> TYPE: DNA
<213> ORGANISM: Artificial Sequence
<220> FEATURE:
<223> OTHER INFORMATION: Primer

<400> SEQUENCE: 17
agtggcttaa tt                                                       12

<210> SEQ ID NO 18
<211> LENGTH: 12
<212> TYPE: DNA
<213> ORGANISM: Artificial Sequence
<220> FEATURE:
<223> OTHER INFORMATION: Primer

<400> SEQUENCE: 18
agtggcttag ca                                                       12

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
agcactctcc agcctctcac cgac                                          24

<210> SEQ ID NO 20
<211> LENGTH: 12
<212> TYPE: DNA
<213> ORGANISM: Artificial Sequence

```
<220> FEATURE:
<223> OTHER INFORMATION: Primer

<400> SEQUENCE: 20
agtcgctgtt aa                                                                 12

<210> SEQ ID NO 21
<211> LENGTH: 12
<212> TYPE: DNA
<213> ORGANISM: Artificial Sequence
<220> FEATURE:
<223> OTHER INFORMATION: Primer

<400> SEQUENCE: 21
agtcgctgtc ga                                                                 12

<210> SEQ ID NO 22
<211> LENGTH: 12
<212> TYPE: DNA
<213> ORGANISM: Artificial Sequence
<220> FEATURE:
<223> OTHER INFORMATION: Primer

<400> SEQUENCE: 22
agtcgctggt ac                                                                 12

<210> SEQ ID NO 23
<211> LENGTH: 12
<212> TYPE: DNA
<213> ORGANISM: Artificial Sequence
<220> FEATURE:
<223> OTHER INFORMATION: Primer

<400> SEQUENCE: 23
agtcgctggg cc                                                                 12

<210> SEQ ID NO 24
<211> LENGTH: 12
<212> TYPE: DNA
<213> ORGANISM: Artificial Sequence
<220> FEATURE:
<223> OTHER INFORMATION: Primer

<400> SEQUENCE: 24
agtcgctggc gc                                                                 12

<210> SEQ ID NO 25
<211> LENGTH: 12
<212> TYPE: DNA
<213> ORGANISM: Artificial Sequence
<220> FEATURE:
<223> OTHER INFORMATION: Primer

<400> SEQUENCE: 25
agtcgctgga tc                                                                 12

<210> SEQ ID NO 26
<211> LENGTH: 12
<212> TYPE: DNA
<213> ORGANISM: Artificial Sequence
<220> FEATURE:
<223> OTHER INFORMATION: Primer

<400> SEQUENCE: 26
agtcgctgct ag                                                                 12
```

```
<210> SEQ ID NO 27
<211> LENGTH: 12
<212> TYPE: DNA
<213> ORGANISM: Artificial Sequence
<220> FEATURE:
<223> OTHER INFORMATION: Primer

<400> SEQUENCE: 27
agtcgctgcg cg                                                              12

<210> SEQ ID NO 28
<211> LENGTH: 12
<212> TYPE: DNA
<213> ORGANISM: Artificial Sequence
<220> FEATURE:
<223> OTHER INFORMATION: Primer

<400> SEQUENCE: 28
agtcgctgcc gg                                                              12

<210> SEQ ID NO 29
<211> LENGTH: 12
<212> TYPE: DNA
<213> ORGANISM: Artificial Sequence
<220> FEATURE:
<223> OTHER INFORMATION: Primer

<400> SEQUENCE: 29
agtcgctgca tg                                                              12

<210> SEQ ID NO 30
<211> LENGTH: 12
<212> TYPE: DNA
<213> ORGANISM: Artificial Sequence
<220> FEATURE:
<223> OTHER INFORMATION: Primer

<400> SEQUENCE: 30
agtcgctgag ct                                                              12

<210> SEQ ID NO 31
<211> LENGTH: 12
<212> TYPE: DNA
<213> ORGANISM: Artificial Sequence
<220> FEATURE:
<223> OTHER INFORMATION: Primer

<400> SEQUENCE: 31
agtcgctgac gt                                                              12

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
accgacgtcg actatccatg aaga                                                 24

<210> SEQ ID NO 33
<211> LENGTH: 12
<212> TYPE: DNA
<213> ORGANISM: Artificial Sequence
<220> FEATURE:
<223> OTHER INFORMATION: Primer
```

<400> SEQUENCE: 33
gtacttcttt aa                                                          12

<210> SEQ ID NO 34
<211> LENGTH: 12
<212> TYPE: DNA
<213> ORGANISM: Artificial Sequence
<220> FEATURE:
<223> OTHER INFORMATION: Primer

<400> SEQUENCE: 34
gtacttctgt ac                                                          12

<210> SEQ ID NO 35
<211> LENGTH: 12
<212> TYPE: DNA
<213> ORGANISM: Artificial Sequence
<220> FEATURE:
<223> OTHER INFORMATION: Primer

<400> SEQUENCE: 35
gtacttctgg cc                                                          12

<210> SEQ ID NO 36
<211> LENGTH: 12
<212> TYPE: DNA
<213> ORGANISM: Artificial Sequence
<220> FEATURE:
<223> OTHER INFORMATION: Primer

<400> SEQUENCE: 36
gtacttctgc gc                                                          12

<210> SEQ ID NO 37
<211> LENGTH: 12
<212> TYPE: DNA
<213> ORGANISM: Artificial Sequence
<220> FEATURE:
<223> OTHER INFORMATION: Primer

<400> SEQUENCE: 37
gtacttctga tc                                                          12

<210> SEQ ID NO 38
<211> LENGTH: 12
<212> TYPE: DNA
<213> ORGANISM: Artificial Sequence
<220> FEATURE:
<223> OTHER INFORMATION: Primer

<400> SEQUENCE: 38
gtacttctct ag                                                          12

<210> SEQ ID NO 39
<211> LENGTH: 12
<212> TYPE: DNA
<213> ORGANISM: Artificial Sequence
<220> FEATURE:
<223> OTHER INFORMATION: Primer

<400> SEQUENCE: 39
gtacttctcg cg                                                          12

<210> SEQ ID NO 40

```
<211> LENGTH: 12
<212> TYPE: DNA
<213> ORGANISM: Artificial Sequence
<220> FEATURE:
<223> OTHER INFORMATION: Primer

<400> SEQUENCE: 40
gtacttctcc gg                                                           12

<210> SEQ ID NO 41
<211> LENGTH: 12
<212> TYPE: DNA
<213> ORGANISM: Artificial Sequence
<220> FEATURE:
<223> OTHER INFORMATION: Primer

<400> SEQUENCE: 41
gtacttctca tg                                                           12

<210> SEQ ID NO 42
<211> LENGTH: 12
<212> TYPE: DNA
<213> ORGANISM: Artificial Sequence
<220> FEATURE:
<223> OTHER INFORMATION: Primer

<400> SEQUENCE: 42
gtacttctag ct                                                           12

<210> SEQ ID NO 43
<211> LENGTH: 12
<212> TYPE: DNA
<213> ORGANISM: Artificial Sequence
<220> FEATURE:
<223> OTHER INFORMATION: Primer

<400> SEQUENCE: 43
gtacttctac gt                                                           12

<210> SEQ ID NO 44
<211> LENGTH: 12
<212> TYPE: DNA
<213> ORGANISM: Artificial Sequence
<220> FEATURE:
<223> OTHER INFORMATION: Primer

<400> SEQUENCE: 44
gtacttctaa tt                                                           12

<210> SEQ ID NO 45
<211> LENGTH: 12
<212> TYPE: DNA
<213> ORGANISM: Artificial Sequence
<220> FEATURE:
<223> OTHER INFORMATION: Primer

<400> SEQUENCE: 45
gtacttctag ca                                                           12

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
```

```
accgacgtcg actatccatg aagc                                          24

<210> SEQ ID NO 47
<211> LENGTH: 12
<212> TYPE: DNA
<213> ORGANISM: Artificial Sequence
<220> FEATURE:
<223> OTHER INFORMATION: Primer

<400> SEQUENCE: 47
gtacttcgtt aa                                                       12

<210> SEQ ID NO 48
<211> LENGTH: 12
<212> TYPE: DNA
<213> ORGANISM: Artificial Sequence
<220> FEATURE:
<223> OTHER INFORMATION: Primer

<400> SEQUENCE: 48
gtacttcgtc ga                                                       12

<210> SEQ ID NO 49
<211> LENGTH: 12
<212> TYPE: DNA
<213> ORGANISM: Artificial Sequence
<220> FEATURE:
<223> OTHER INFORMATION: Primer

<400> SEQUENCE: 49
gtacttcggt ac                                                       12

<210> SEQ ID NO 50
<211> LENGTH: 12
<212> TYPE: DNA
<213> ORGANISM: Artificial Sequence
<220> FEATURE:
<223> OTHER INFORMATION: Primer

<400> SEQUENCE: 50
gtacttcggg cc                                                       12

<210> SEQ ID NO 51
<211> LENGTH: 12
<212> TYPE: DNA
<213> ORGANISM: Artificial Sequence
<220> FEATURE:
<223> OTHER INFORMATION: Primer

<400> SEQUENCE: 51
gtacttcggc gc                                                       12

<210> SEQ ID NO 52
<211> LENGTH: 12
<212> TYPE: DNA
<213> ORGANISM: Artificial Sequence
<220> FEATURE:
<223> OTHER INFORMATION: Primer

<400> SEQUENCE: 52
gtacttcggt ac                                                       12

<210> SEQ ID NO 53
<211> LENGTH: 12
<212> TYPE: DNA
```

```
<213> ORGANISM: Artificial Sequence
<220> FEATURE:
<223> OTHER INFORMATION: Primer

<400> SEQUENCE: 53
gtacttcgct ag                                                      12

<210> SEQ ID NO 54
<211> LENGTH: 12
<212> TYPE: DNA
<213> ORGANISM: Artificial Sequence
<220> FEATURE:
<223> OTHER INFORMATION: Primer

<400> SEQUENCE: 54
gtacttcgcg cg                                                      12

<210> SEQ ID NO 55
<211> LENGTH: 12
<212> TYPE: DNA
<213> ORGANISM: Artificial Sequence
<220> FEATURE:
<223> OTHER INFORMATION: Primer

<400> SEQUENCE: 55
gtacttcgcc gg                                                      12

<210> SEQ ID NO 56
<211> LENGTH: 12
<212> TYPE: DNA
<213> ORGANISM: Artificial Sequence
<220> FEATURE:
<223> OTHER INFORMATION: Primer

<400> SEQUENCE: 56
gtacttcgca tg                                                      12

<210> SEQ ID NO 57
<211> LENGTH: 12
<212> TYPE: DNA
<213> ORGANISM: Artificial Sequence
<220> FEATURE:
<223> OTHER INFORMATION: Primer

<400> SEQUENCE: 57
gtacttcgag ct                                                      12

<210> SEQ ID NO 58
<211> LENGTH: 12
<212> TYPE: DNA
<213> ORGANISM: Artificial Sequence
<220> FEATURE:
<223> OTHER INFORMATION: Primer

<400> SEQUENCE: 58
gtacttcgac gt                                                      12

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
accgacgtcg actatgga                                                18
```

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
accgacgtcg actatggatg aaga              24

<210> SEQ ID NO 61
<211> LENGTH: 12
<212> TYPE: DNA
<213> ORGANISM: Artificial Sequence
<220> FEATURE:
<223> OTHER INFORMATION: Primer

<400> SEQUENCE: 61
ctacttctgt ac              12

<210> SEQ ID NO 62
<211> LENGTH: 12
<212> TYPE: DNA
<213> ORGANISM: Artificial Sequence
<220> FEATURE:
<223> OTHER INFORMATION: Primer

<400> SEQUENCE: 62
ctacttctgg cc              12

<210> SEQ ID NO 63
<211> LENGTH: 12
<212> TYPE: DNA
<213> ORGANISM: Artificial Sequence
<220> FEATURE:
<223> OTHER INFORMATION: Primer

<400> SEQUENCE: 63
ctacttctct ag              12

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
accgacgtcg actatcggat gaga              24

<210> SEQ ID NO 65
<211> LENGTH: 12
<212> TYPE: DNA
<213> ORGANISM: Artificial Sequence
<220> FEATURE:
<223> OTHER INFORMATION: Primer

<400> SEQUENCE: 65
cctactctgt ac              12

<210> SEQ ID NO 66
<211> LENGTH: 24
<212> TYPE: DNA
<213> ORGANISM: Artificial Sequence
<220> FEATURE:

-continued

<223> OTHER INFORMATION: Primer

<400> SEQUENCE: 66
accgacgtcg actatccgga tgga                                   24

<210> SEQ ID NO 67
<211> LENGTH: 12
<212> TYPE: DNA
<213> ORGANISM: Artificial Sequence
<220> FEATURE:
<223> OTHER INFORMATION: Primer

<400> SEQUENCE: 67
gcctacctgt ac                                                12

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
accgacgtcg actatccagg atga                                   24

<210> SEQ ID NO 69
<211> LENGTH: 12
<212> TYPE: DNA
<213> ORGANISM: Artificial Sequence
<220> FEATURE:
<223> OTHER INFORMATION: Primer

<400> SEQUENCE: 69
gtcctactgt ac                                                12

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
accgacgtcg actatcgcag caga                                   24

<210> SEQ ID NO 71
<211> LENGTH: 12
<212> TYPE: DNA
<213> ORGANISM: Artificial Sequence
<220> FEATURE:
<223> OTHER INFORMATION: Primer

<400> SEQUENCE: 71
cgtcgtctct ag                                                12

<210> SEQ ID NO 72
<211> LENGTH: 12
<212> TYPE: DNA
<213> ORGANISM: Artificial Sequence
<220> FEATURE:
<223> OTHER INFORMATION: Primer

<400> SEQUENCE: 72
cgtcgtctgt ac                                                12

```
<210> SEQ ID NO 73
<211> LENGTH: 24
<212> TYPE: DNA
<213> ORGANISM: Artificial Sequence
<220> FEATURE:
<223> OTHER INFORMATION: Primer

<400> SEQUENCE: 73
accgacgtcg actatccatg acgc                                              24

<210> SEQ ID NO 74
<211> LENGTH: 12
<212> TYPE: DNA
<213> ORGANISM: Artificial Sequence
<220> FEATURE:
<223> OTHER INFORMATION: Primer

<400> SEQUENCE: 74
gtactgcggt ac                                                           12

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
accgacgtcg actatggatg aagatggt                                          28

<210> SEQ ID NO 76
<211> LENGTH: 39
<212> TYPE: DNA
<213> ORGANISM: Artificial Sequence
<220> FEATURE:
<223> OTHER INFORMATION: Primer

<400> SEQUENCE: 76
gacatccata gtcgacgtcg gttttttccc cccccccc                               39

<210> SEQ ID NO 77
<211> LENGTH: 49
<212> TYPE: DNA
<213> ORGANISM: Artificial Sequence
<220> FEATURE:
<223> OTHER INFORMATION: Primer

<400> SEQUENCE: 77
gacatccata gtcgacgtcg gttttttttt ttttttccc cccccccc                     49

<210> SEQ ID NO 78
<211> LENGTH: 34
<212> TYPE: DNA
<213> ORGANISM: Artificial Sequence
<220> FEATURE:
<223> OTHER INFORMATION: Primer

<400> SEQUENCE: 78
gacatccata gtcgacgtcg gtcccccccc cccc                                   34

<210> SEQ ID NO 79
<211> LENGTH: 39
<212> TYPE: DNA
<213> ORGANISM: Artificial Sequence
<220> FEATURE:
<223> OTHER INFORMATION: Primer
```

<400> SEQUENCE: 79
ggtactgtgc tatccgaggg aatttttccc cccccccc        39

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
tggtgatcct tcaaggtttt tcccccc        27

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
accgacgtcg actatccatg aagc        24

<210> SEQ ID NO 82
<211> LENGTH: 28
<212> TYPE: DNA
<213> ORGANISM: Artificial Sequence
<220> FEATURE:
<223> OTHER INFORMATION: Primer

<400> SEQUENCE: 82
tgtcgcttca tccatagtcg acgtcggt        28

<210> SEQ ID NO 83
<211> LENGTH: 33
<212> TYPE: DNA
<213> ORGANISM: Artificial Sequence
<220> FEATURE:
<223> OTHER INFORMATION: Primer

<400> SEQUENCE: 83
taccaccggg cttcatccat agtcgacgtc ggt        33

<210> SEQ ID NO 84
<211> LENGTH: 29
<212> TYPE: DNA
<213> ORGANISM: Artificial Sequence
<220> FEATURE:
<223> OTHER INFORMATION: Primer

<400> SEQUENCE: 84
accgacgtcg actatggatg aagcccggt        29

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
ttccctcgga tagcacag        18

<210> SEQ ID NO 86
<211> LENGTH: 25

```
<212> TYPE: DNA
<213> ORGANISM: Artificial Sequence
<220> FEATURE:
<223> OTHER INFORMATION: Primer

<400> SEQUENCE: 86
gatcaccagt atggtggcca gcggc                                    25

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
tggtcatacc accggtcgcc g                                        21

<210> SEQ ID NO 88
<211> LENGTH: 27
<212> TYPE: DNA
<213> ORGANISM: Artificial Sequence
<220> FEATURE:
<223> OTHER INFORMATION: Primer

<400> SEQUENCE: 88
tggtgacgct tcaaggtttt tcccccc                                  27
```